(12) United States Patent
Coull et al.

(10) Patent No.: US 6,361,942 B1
(45) Date of Patent: Mar. 26, 2002

(54) METHOD, KITS AND COMPOSITIONS PERTAINING TO DETECTION COMPLEXES

(75) Inventors: James M. Coull, Westford; Brian D. Gildea, Billerica; Jens J. Hyldig-Nielsen, Holliston, all of MA (US)

(73) Assignee: Boston Probes, Inc., Bedford, MA (US)

( * ) Notice: Subject to any disclaimer, the term of this patent is extended or adjusted under 35 U.S.C. 154(b) by 0 days.

(21) Appl. No.: 09/275,848

(22) Filed: Mar. 24, 1999

Related U.S. Application Data

(60) Provisional application No. 60/079,211, filed on Mar. 24, 1998.

(51) Int. Cl.[7] .................... C12Q 1/68; G01N 33/53; G01N 15/00; A61K 38/00; C07H 21/00

(52) U.S. Cl. .................... 435/6; 435/7.1; 530/300; 536/22.1; 536/24.1; 422/50; 422/68.1

(58) Field of Search ................... 435/6, 7.1, 7.2; 530/300, 350; 536/22.1, 23.1, 24.1, 24.3–24.33; 422/50, 68.1

(56) References Cited

U.S. PATENT DOCUMENTS

| | | | |
|---|---|---|---|
| 4,174,384 A | 11/1979 | Ullman et al. ............... | 424/8 |
| 4,261,968 A | 4/1981 | Ullman et al. ............... | 424/8 |
| 4,542,104 A | 9/1985 | Stryer et al. ............... | 436/536 |

(List continued on next page.)

FOREIGN PATENT DOCUMENTS

| | | | |
|---|---|---|---|
| EP | 0853129 A2 | | 7/1998 |
| EP | 0909823 | | 4/1999 |
| WO | 92/20702 | * | 11/1992 |
| WO | WO95/13399 | | 5/1995 |
| WO | WO97/14026 | | 4/1997 |
| WO | WO97/18325 | | 5/1997 |
| WO | WO97/39008 | | 10/1997 |
| WO | WO97/46711 | | 12/1997 |
| WO | WO97/46714 | | 12/1997 |
| WO | WO98/10096 | | 3/1998 |
| WO | WO98/14612 | | 4/1998 |
| WO | WO98/18965 | | 5/1998 |
| WO | WO98/24933 | | 6/1998 |
| WO | WO98/26093 | | 6/1998 |
| WO | WO98/29568 | | 7/1998 |
| WO | WO98/30883 | | 7/1998 |
| WO | WO98/37232 | | 8/1998 |
| WO | WO99/21881 | | 5/1999 |
| WO | WO99/22018 | | 5/1999 |
| WO | WO99/23250 | | 5/1999 |

OTHER PUBLICATIONS

Uhlmann et al., Chemical Reviews, vol. 90, No. 4, pp. 543–584, 1990.*

Orum et al., Nucleic Acids Research, vol. 21, No. 23, pp. 5332–5336, 1993.*

Nazarenko et al., Nucleic Acids Research, vol. 25, No. 12, pp. 2516–2521, 1997.*

(List continued on next page.)

*Primary Examiner*—Ardin H. Marschel
(74) *Attorney, Agent, or Firm*—Brian D. Gildea

(57) ABSTRACT

This invention is directed to methods, kits and compositions which utilize Detection Complexes to detect or identify the presence, absence or quantity of a target molecule in a sample of interest. A Detection Complex comprises at least two component polymers and at least one set of donor and accepter moieties. To each of at least two component polymers is linked at least one moiety of a set of donor and accepter moieties, such that formation of the complex facilitates transfer of energy between donor and acceptor moieties of each set in a manner which, in an assay, produces changes in detectable signal which can be correlated with the presence absence of quantity of target sequence and/or target molecule of interest in the sample.

102 Claims, 20 Drawing Sheets

U.S. PATENT DOCUMENTS

| | | | | |
|---|---|---|---|---|
| 4,666,862 A | | 5/1987 | Chan | 436/501 |
| 4,683,195 A | * | 7/1987 | Mullis et al. | 435/6 |
| 4,725,536 A | | 2/1988 | Fritsch et al. | 435/6 |
| 4,725,537 A | | 2/1988 | Fritsch et al. | 435/6 |
| 4,766,062 A | | 8/1988 | Diamond et al. | 435/6 |
| 4,820,630 A | * | 4/1989 | Taub | 435/5 |
| 4,822,733 A | | 4/1989 | Morrison | 435/6 |
| 4,868,103 A | | 9/1989 | Stavrianopoulos et al. | 435/5 |
| 4,996,143 A | * | 2/1991 | Heller et al. | 435/6 |
| 5,118,801 A | | 6/1992 | Lizardi et al. | 536/27 |
| 5,210,015 A | | 5/1993 | Gelfand et al. | 435/6 |
| 5,237,515 A | | 8/1993 | Herron et al. | 364/498 |
| 5,288,611 A | | 2/1994 | Kohne | 435/6 |
| 5,312,728 A | | 5/1994 | LIzardi et al. | 435/6 |
| 5,348,853 A | | 9/1994 | Wang et al. | 435/6 |
| 5,439,793 A | | 8/1995 | Rose et al. | 435/6 |
| 5,439,797 A | | 8/1995 | Tsien et al. | 435/7.21 |
| 5,491,063 A | | 2/1996 | Fisher et al. | 435/6 |
| 5,503,980 A | | 4/1996 | Cantor | 435/6 |
| 5,510,270 A | * | 4/1996 | Fodor et al. | 436/518 |
| 5,514,546 A | | 5/1996 | Kool | 435/6 |
| 5,527,675 A | | 6/1996 | Coull et al. | 435/6 |
| 5,538,848 A | | 7/1996 | Livak et al. | 435/5 |
| 5,539,082 A | | 7/1996 | Nielsen et al. | 530/300 |
| 5,573,906 A | | 11/1996 | Bannwarth et al. | 435/6 |
| 5,601,984 A | | 2/1997 | Kohne | 435/6 |
| 5,607,834 A | | 3/1997 | Bagwell | 435/6 |
| 5,612,183 A | | 3/1997 | Kohne | 435/6 |
| 5,623,049 A | | 4/1997 | Lobberding et al. | 530/300 |
| 5,631,169 A | | 5/1997 | Lakowicz et al. | 436/537 |
| 5,641,631 A | | 6/1997 | Kohne | 435/6 |
| 5,643,762 A | | 7/1997 | Ohshima et al. | 435/91.1 |
| 5,675,517 A | | 10/1997 | Stokdijk | 364/571.01 |
| 5,691,145 A | | 11/1997 | Pitner et al. | 435/6 |
| 5,691,146 A | | 11/1997 | Mayrand | 435/6 |
| 5,705,346 A | | 1/1998 | Okamoto et al. | 435/6 |
| 5,707,804 A | | 1/1998 | Mathies et al. | 435/6 |
| 5,714,331 A | | 2/1998 | Buchardt et al. | 435/6 |
| 5,723,294 A | | 3/1998 | Glass et al. | 435/6 |
| 5,728,526 A | | 3/1998 | George, Jr. et al. | 435/6 |
| 5,731,148 A | | 3/1998 | Becker et al. | 435/6 |
| 5,736,336 A | | 4/1998 | Buchardt et al. | 435/6 |
| 5,763,167 A | | 6/1998 | Conrad | 435/6 |
| 5,770,365 A | | 6/1998 | Lane et al. | 435/6 |
| 5,773,571 A | | 6/1998 | Nielsen et al. | 530/300 |
| 5,780,233 A | | 7/1998 | Guo et al. | 435/6 |
| 5,786,461 A | | 7/1998 | Buchardt et al. | 536/18.7 |
| 5,787,032 A | | 7/1998 | Heller et al. | 365/151 |
| 5,800,995 A | * | 9/1998 | Lee et al. | 435/6 |
| 5,804,836 A | | 9/1998 | Ju | 435/6 |
| 5,814,492 A | | 9/1998 | Carrino et al. | 435/91.2 |
| 5,827,660 A | | 10/1998 | Singer et al. | 435/6 |
| 5,831,014 A | | 11/1998 | Cook et al. | 530/350 |
| 5,846,729 A | | 12/1998 | Wu et al. | 435/6 |
| 5,866,336 A | | 2/1999 | Nazarenko et al. | 435/6 |
| 5,925,517 A | | 7/1999 | Tyagi et al. | 435/6 |
| 5,928,869 A | | 7/1999 | Nadeau et al. | 435/6 |
| 5,958,700 A | | 9/1999 | Nadeau et al. | 435/6 |
| 5,985,563 A | | 11/1999 | Hyldig-Nielsen et al. | 435/6 |
| 6,020,126 A | * | 2/2000 | Carlsson et al. | 435/6 |
| 6,110,676 A | | 8/2000 | Coull et al. | 435/6 |

OTHER PUBLICATIONS

Armitage, B. et al, Hairpin–forming peptide nucleic acid oligomers. Biochem. 37, 9417–9425 (1998).

Bagwell, C.B. et al, A new homogeneous assay system for specific nucleic acid sequences: poly–dA and poly–A detection. Nucleic Acids Res. 22, 2424–2425 (1994).

Blok, H.J. et al, Amplifiable hybridization probes containing a molecular switch. Molecular and Cellular Probes 11, 187–194 (1997).

Cardullo, R.A. et al, Detection of nucleic acid hybridization by nonradiative fluorescence resonance energy transfer. Proc. Natl. Acad. Sci. USA 85, 8790–8794 (1988).

Carmel, A. et al, Intramolecularly–quenched fluorescent peptides as fluorogenic substrates of leucine aminopeptidase and inhibitors of clostridial aminopeptidase. Eur. J. Biochem. 73, 617–625 (1977).

Chen, X. et al, A homogeneous ligase–mediated DNA diagonstic test. Genome Res 8, 549–556 (1998).

Clegg, R.M., Fluorescence Resonance Energy Transfer and Nucleic Acids. Methods in Enzymology 211, 353–388 (1992).

Corey, D.R. 48000–fold Acceleration of Hybridization by Chemically Modified Oligonucleotides. J. Am. Chem. Soc. 117, 9373–9374 (1995).

Diederichsen, U. et al, Self–Pairing PNA with alternating alanyl/homoalanyl backbone. Tett. Lett. 37, 475–478 (1996).

Dueholm, K.L. et al, Chemistry, properties and applications of PNA (Peptide Nucleic Acid). New J. Chem. 21, 19–31 (1977).

Egholm, M. et al, PNA hybridizes to complementary oligonucleotides obeying the Watson–Crick hydrogen–binding rules. Nature 365, 566–568 (1993).

Ferguson, J.A. et al, A fiber–optic DNA biosensor microarray for the analysis of gene expression. Nature Biotech. 14, 1681–1684 (1996).

Fujii, M. et al, Nucleic acid analog peptide (NAAP)2, syntheses and properties of novel DNA analog peptides containing nucleobase linked β–aminoalanine. Bioorg. & Med. Chem. Lett. 7, 637–640 (Mar. 1997).

Guo, Z. et al, Direct fluorescence analysis of genetic polymorphisms by hybridization with oligonucleotide arrays on glass supports. Nucleic Acids Res. 22, 5456–5465 (1994).

Guo, Z. et al, Enhanced discrimination of single nucleotide polymorphisms by artificial mismatch hybridization. Nature Biotech. 15, 331–335 (1997).

Haasnoot, C.A.G. et al, Structure, kinetics and thermodynamics of DNA hairpin fragments in solution. J. Biomolecular Structure and Dynamics 1, 115–129 (1983).

Holland, P.M. et al, Detection of specific polymerase chain reaction product by utilizing the 5'→3' exonuclease activity of *Thermus aquaticus* DNA polymerase. Proc. Natl. Acad. Sci. USA 88, 7276–7280 (1991).

Hung, S.–C. et al, Comparison of fluorescence energy transfer primers with different donor–acceptor dye combinations. Analy. Biochem. 255, 32–38 (1998).

Hyldig–Nielsen, J.J. et al, Advances in the use of PNA probes for diaganostic testing. IBC's 3rd Annual International Symposium on Diagnostic Gene Detection and Quantification Technologies for Infectious Agents and Human Genetic Diseases. Feb. 25–27, 1998, Lake Tahoe, NV.

Hyrup, B. et al, Peptide Nucleic Acids (PNA): Synthesis, Properties and Potential Applications. Bioorg. & Med. Chem. 4, 5–23 (1996).

Iyer, M. et al, Accelerated Hybridization of Oligonucleotides to Duplex DNA. The J. of Biol. Chem. 270, 14712–14717 (1995).

Jordan, S. et al, New hetero–oligomeric peptide nucleic acids with improved binding properties to complementary DNA. Bioorg. & Med. Chem. Lett. 7, 687–690 (1997).

Jordan, S. et al, Synthesis of new building blocks for peptide nucleic acids containing monomers with variations in the backbone. Bioorg & Med. Chem. lett. 7, 681–686 (1997).

Ju, J. et al, Fluorescence energy transfer dye–labeled primers for DNA sequencing and analysis. Proc. Natl. Acad. Sci. USA 92, 4347–4351 (1995).

Kostrikis, L.G. et al, Spectral genotyping of human alleles. Science 279, 1228–1229 (1998).

Krotz, A.H. et al, Synthesis of "Retro–inverso" Peptide Nucleic Acids: 2. Oligomerization and stability, Tett. Lett. 36, 6941–6944 (1995).

Lagriffoul, P.–H. et al, The synthesis, co–oligermization and hybridization of a thymine–thymine heterodimer containing PNA. Bioorg. & Med. Chem. Lett. 4, 1081–1082 (1994).

Larin, Z. et al, Fluorescence in situ hybridisation of multiple probes on a single microscope slide. Nucleic Acids Res. 22, 3689–3692 (1994).

Lee, L.G. et al, Allelic discrimination by nick–translation PCR with fluorogenic probes. Nucleic Acids Res. 21, 3761–3766 (1993).

Leone, G. et al, Molecular beacon probes combined with amplification by NASBA enable homogeneous, real–time detection of RNA. Nucl. Acids Res. 26, 2150–2155 (1998).

Lester, A. et al, PNA array technology. Presented at Biochip Technologies Conference in Annapolis (Oct. 1997).

Lewis, R. Oncor and Chiron Offer Improvements & Alternatives in Gene Amplification. Gen. Eng. News. 17, 3 & 36 (Jun. 1, 1997).

Livak, K.J. et al, Oligonucleotides with Fluorescent Dyes at Opposite Ends Provide a Quenched Probe System useful for Detecting PCR Product and Nucleic Acid Hybridization. PCR Methods and Applic. 4, 357–362 (1995).

Lowe, G. et al, Amino acids bearing nucleobases for the synthesis of novel peptide nucleic acids. J. Chem. Soc., Perkin Trans. 1, 4, 539–546 (1997).

Lowe, G. et al, Dipeptides bearing nucleobases for the synthesis of novel peptide nucleic acids. J. Chem. Soc. Perkin Trans. 1, 4, 547–554 (1997).

Lowe, G. et al, Solid–phase synthesis of novel peptide nucleic acids. J. Chem. Soc., Perkin Trans. 1, 4, 555–560 (1997).

Lutz, M.J. et al, Recognition of Uncharged Polyamide–Linked Nucleic Acid Analogs by DNA Polymerases and Reverse Transcriptases. J. Am. Chem. Soc. 119, 3177–3178 (1997).

Lyamichev, V. et al, Structure–Specific Endonucleolytic Cleavage of Nucleic Acids by Eubacterial DNA Polymerases. Science 260, 778–783 (1993).

Matray, T.J. et al, Selective and stable DNA base pairing without hydrogen bonds. J. Am. Chem. Soc. 120, 6191–6192 (1998).

Meldal, M. et al, Anthranilamide and Nitrotyrosine as a Donor–Acceptor Pair in Internally Quenched Fluorescent Substrates for Endopeptidases: Multicolumn Peptide Synthesis of Enzyme Substrates for Subtilisin Carlsberg and Pepsin. Anal. Biochem. 195, 141–147 (1991).

Mergny, J.–L. et al, Fluorescence Energy Transfer between Two Triple Helix–Forming Oligonucleotides Bound to Duplex DNA. Biochem. 33, 15321–15328 (1994).

Nazarenko, I.A., A Closed–Tube Format for Amplification and Detection of Nucleic Acids Based on Energy Transfer. Fifth Annual Advances in Nucleic Acid Amplification and Detection, San Francisco, CA (Jun. 16–17, 1997).

Ng, M. et al, A Fluorescent Oligopeptide Energy Transfer Assay with Broad Applications for Neutral Proteases. Anal. Biochem. 183, 50–56 (1989).

Nielsen, P.E. et al, Peptide Nucleic Acid (PNA). A DNA Mimic with a Peptide Backbone. Biocon. Chem. 5, 3–7 (1994).

Nielsen, P.E. et al, Peptide nucleic acids (PNAs): Potential Antisense and Anti–gene Agents. Anti–Cancer Drug Design 8, 53–63 (1993).

Oncor, Inc. Press Release Apr. 14, 1997.

Paris, P.L. et al, Probing DNA sequences in solution with a monomer–excimer fluorescence color change. Nucl. Acids Res. 26, 3789–3793 (1998).

Parkhurst, K.M. et al, Kinetic Studies by Fluorescence Resonance Energy Transfer Employing a Double–Labeled Oligonucleotide: Hybridization to the Oligonucleotide Complement and to Single–Stranded DNA. Biochem. 34, 285–292 (1995).

PerSeptive Biosystems Promotional Literature. Bio ConSepts. vol. 4, No. 3, Publication #NL612 (1996).

PerSeptive Biosystems Promotional Literature. Practical PNA, Review. Peptide Nucleic Acids (PNA): Expanding the role of synthetic DNA analogs. publication #PN001 (1995).

PerSeptive Biosystems Promotional Literature. Peptide Nucleic Acids (PNA): Probing the improbable. Publication #PNA001.00 (1997).

PerSeptive Biosystems Promotional Literature. Practical PNA. vol. 1, Iss. 2. PNA Oligomers as hybridization probes. Publication #PN003 (1995).

Petersen, K.H. et al, Synthesis and oligomerization of $N^\delta$–Boc–$N^\alpha$–(thymin–1–ylacetyl)ornithin. Bioorg. & Med. Chem. Lett. 6, 793–796 (1996).

Piatek, A.S. et al, Molecular beacon sequence analysis for detecting drug resistance in *mycobacterium tuberculosis*. Nature Biotech. 16, 359–363 (1998).

Promisel Cooper, J. et al, Analysis of Fluoroescence Energy Transfer in Duplex and Branched DNA Molecules. Biochem. 29, 9261–9268 (1990).

Ratilainen, T. et al, Hybridization of peptide nucleic acid. Biochem. 37, 12331–12342 (1998).

Rye, H.S. et al, Stable fluorescent complexes of double–stranded DNA with bis–intercalating asymmetri cyanine dyes: properties and applications. Nucleic Acids Res. 20, 2803–2812 (1992).

Scheffler, I.E. et al. Helix formation by dAT oligomers. I. Hairpin and straight–chain helices. J. Mol. Biol. 36, 291–304 (1968).

Selvin, P.R., Fluorescence Resonance Energy Transfer. Methods in Enzymology 246, 300–334 (1995).

Singh, D. et al, Oligonucleotides, part 5+: synthesis and fluorescence studies of DNA oligomers $d(AT)_5$ containing adenines covalently linked at C–8 with dansyl fluorophore. Nucleic Acids Res. 18, 3339–3345 (1990).

Sixou, S. et al, Intracellular oligonucleotide hybridization detected by fluorescence resonance energy transfer (FRET). Nucleic Acids Res. 22, 662–668 (1994).

Sosnowski, R.G. et al, Rapid determination of single base mismatch mutations in DNA hybrids by direct electric field control. Proc. Natl. Acad. Sci. USA 94, 1119–1123 (1997).

Thisted, M. et al, Detection of immunoglobulin kappa light chain mRNA in paraffin sections by in situ hybridization using peptide nucleic acid probes. Cell Vision 3, 358–363 (1996).

Thornton, N.B. et al, Chromophore–quencher probes for DNA. New J. Chem. 20, 791–800 (1996).

Tomac, S. et al, Ionic effects on the stability and conformation of Peptide Nucleic Acid Complexes. J. Am. Chem. Soc. 118, 5544–5552 (1996).

Tyagi, S. et al, Molecular Beacons; Probes that fluoresce upon Hybridization. Nature Biotech. 14, 303–308 (1996).

Tygai, S. et al, Multicolor molecular beacons for allele discrimination. Nature Biotech. 16, 49–53 (1998).

van Gemen, B. et al, Qualitative and quantitative detection of HIV–1 RNA by nucleic acid sequence–based amplification. AIDS 7, S107–S110 (1993).

Vaughan, W.M. et al, Oxygen quenching of pyrenebutyric acid fluorescence in water. A dynamic probe of the microenvironment. Biochem. 9, 464–473 (1970).

Wang, G.T. et al, Design and Synthesis of New Fluorogenic HIV Protease Substrates Based on Resonance Energy Transfer. Tett. Lett. 31, 6493–6496 (1990).

Wang, J. et al, Peptide nucleic acid probes for sequence–specific DNA biosensors. J. Amer. Chem. Soc. 118, 7667–7670 (1996).

Weber, P.J.A. et al, A fast and inexpensive method for N–terminal fluoresein–labeling of peptides. Bioorg & Med. Chem. Lett. 8, 597–600 (1998).

Weiler, J. et al, Hybridisation based DNA screening on peptide nucleic acid (PNA) oligomer arrays. Nucl. Acids Res. 25, 2792–2799 (1997).

Wittung, P. et al, Induced Chirality in PNA–DNA Duplexes. J. Am. Chem. Soc. 117, 10167–10173 (1995).

Yamamoto, N. et al, A rpaid detection of PCR amplification product using a new fluorescent intercalator; the pyrylium dye, P2. Nucleic Acids Res. 23, 1445–1446 (1995).

Yang, M. et al, A DNA assay based on fluorescence resonance energy transfer and DNA triplex formation. Analy. Biochem. 259, 272–274 (1998)

Yaron, A. et al, Intramolecularly quenched fluorogenic substrates for hydrolytic enzymes. Analy. Biochem. 95, 228–235 (1979).

Zimmerman, M. et al, A New Fluorogenic Substrate for Chymotrypsin. Anal. Biochem. 70, 258–62 (1976).

Ortiz, E. et al, PNA molecular beacons for rapid detection of PCR. Mol. Cell. Probes 12(4), 219–226 (1998).

Schmitt, E. et al, Bax–α promotes apoptosis Induced by cancer chemotherapy and accelerate the activation of caspase 3–like cysteine proteases In p53 double mutant B lymphoma Namalwa cells, Cell Death Differ. 5(6), 506–516 (1998).

Corey, D.R., Peptide nucleic acids: expanding the scope of nucleic acid recognition. TIBTECH 15, 224–229 (1997).

Ishiguro, T. et al, Fluorescence detection of specific sequence of nucleic acids by oxazole yellow–linked oligonucleotides. Homogeneous quantitative monitoring of In vitro transcription, Nucleic Acids Research 24(24), 4992–4997 (1996).

Morrison, L.E. et al, Sensitive Fluorescence–Based Thermodynamic and Kinetic Measurements of DNA Hybridization In Solution, Biochemistry 32, 3095–3104 (1993).

Morrison, L.E. et al, Solution–Phase Detection of Polynucleotides Using Interacting Fluorescent Labels and Competitive Hybridization, Analytical Biochemistry 183, 231–244 (1989).

Yamana, K et al, Enhanced fluorescence In the binding of oligonucleotides with a pyrene group In the sugar fragment to complementary polynucleotides, Nucleosides & Nucleotides 11(2–4), 383–390 (1992).

\* cited by examiner

Figure 1
A
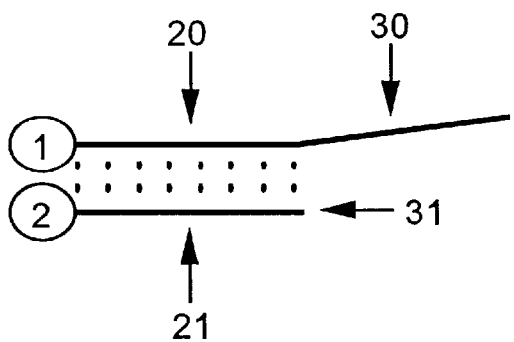
B
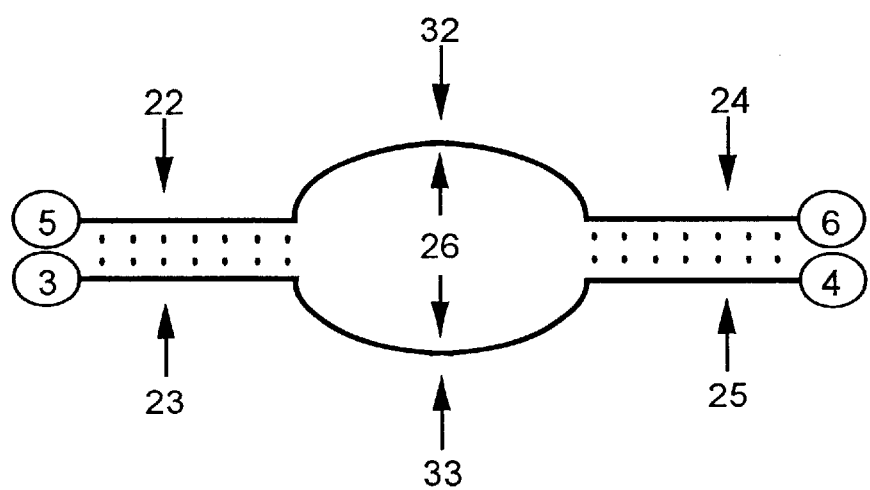
C
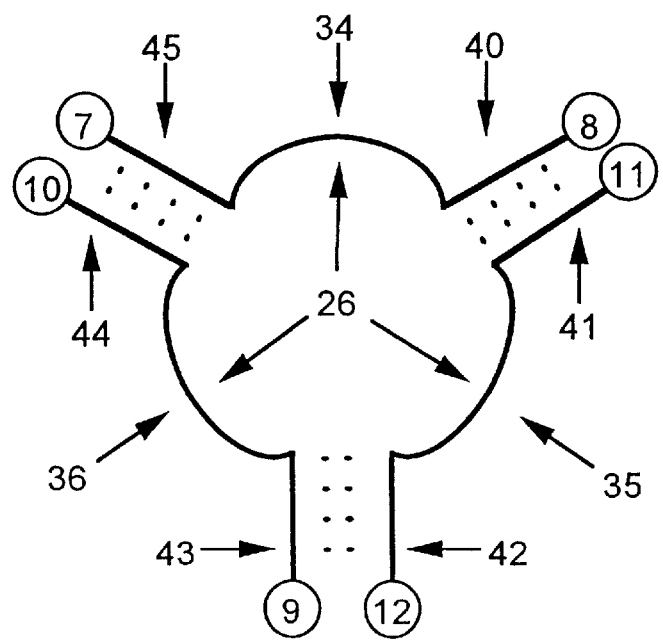

Round 1 of PCR

Round 2 of PCR

Final PCR Product

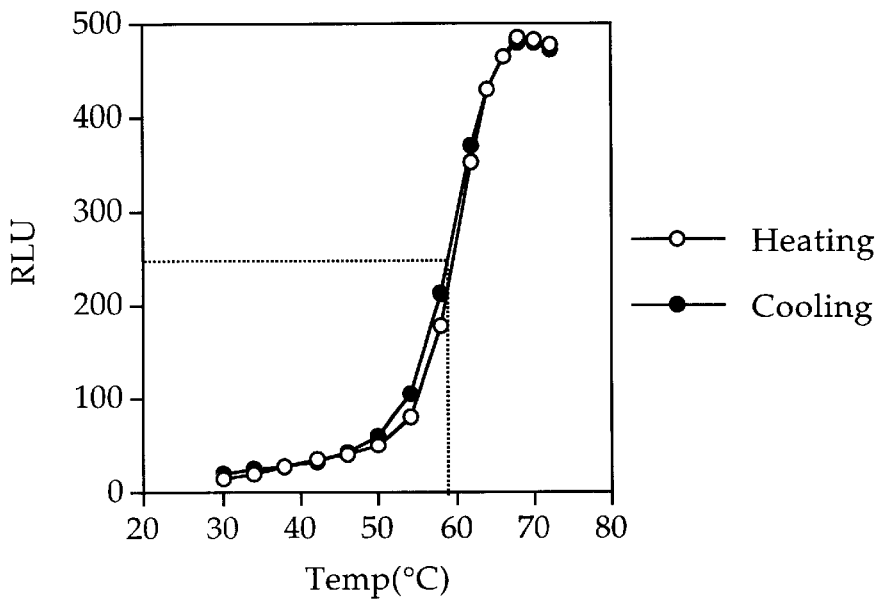
Thermal Profile of the Complex Formed from the 3' DNA Primer and the PNA Quencher (1:2 ratio).
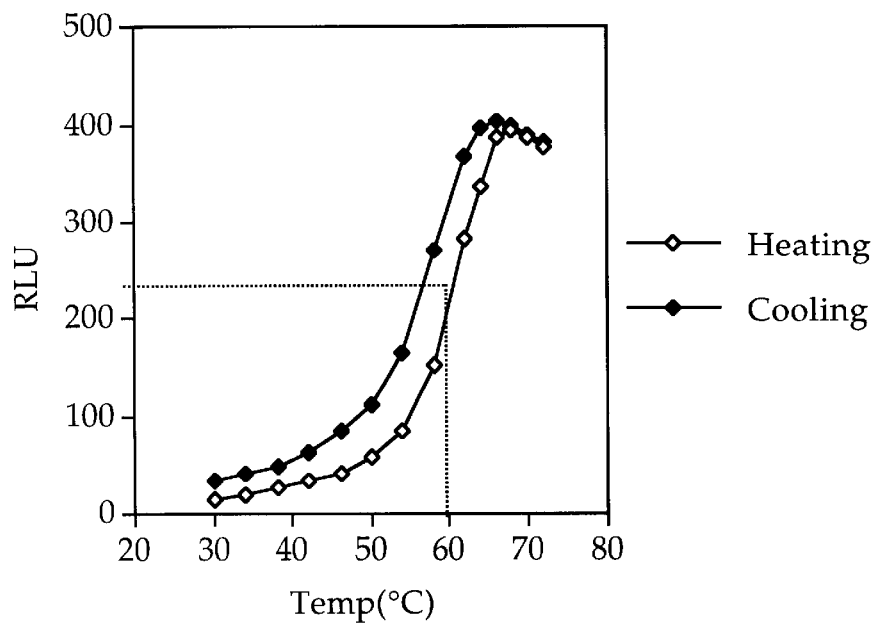
Thermal Profile of the Complex Formed from the 5' DNA Primer and the PNA Quencher (1:2 ratio).

Figure 19
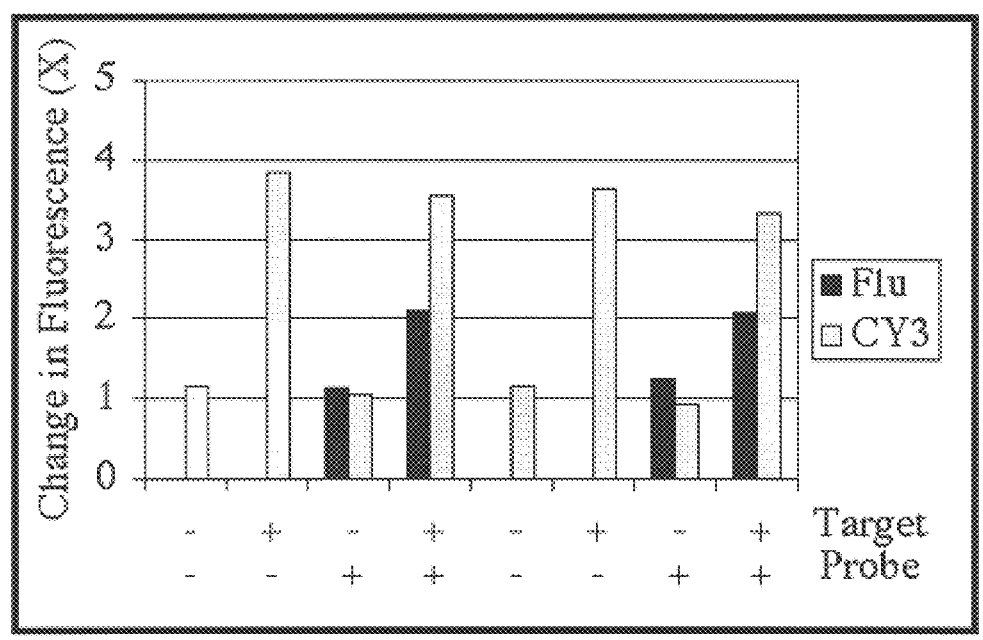
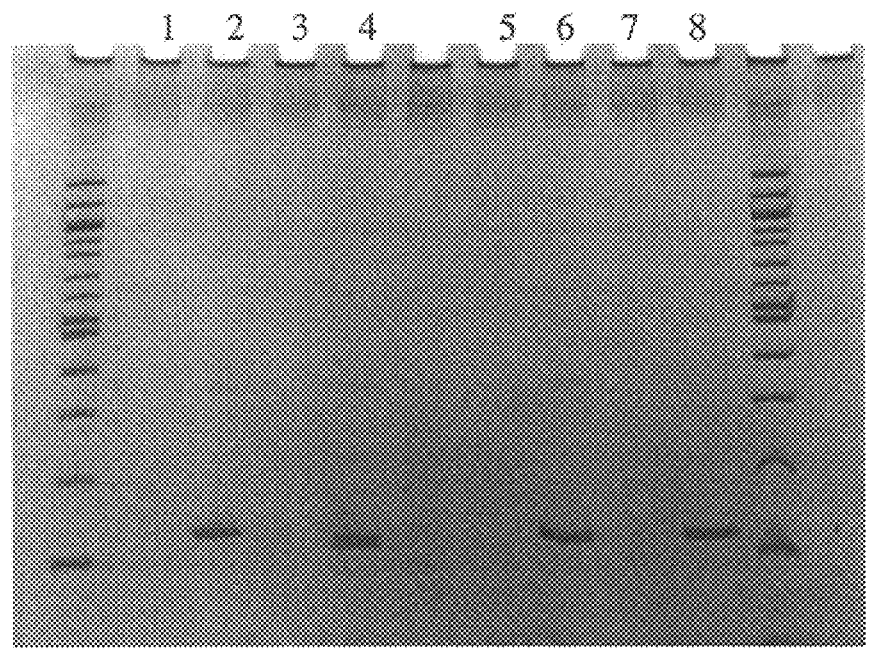

Figure 20
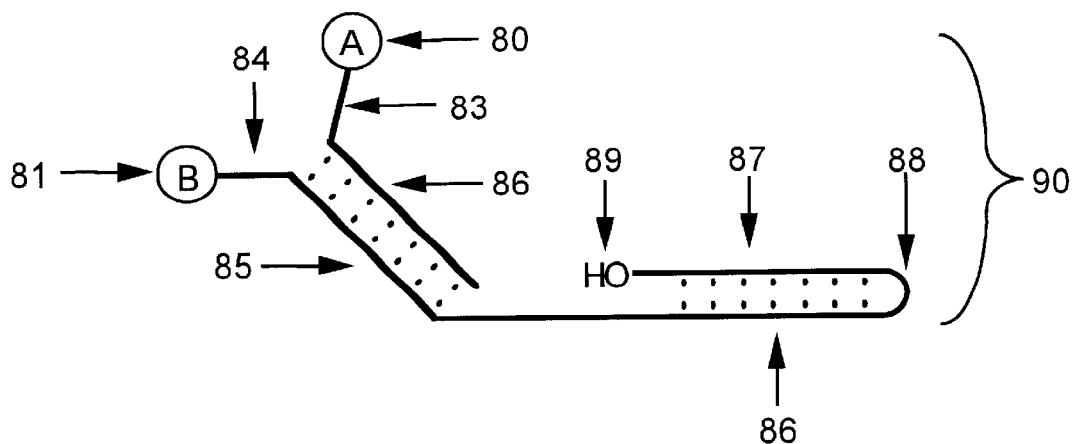
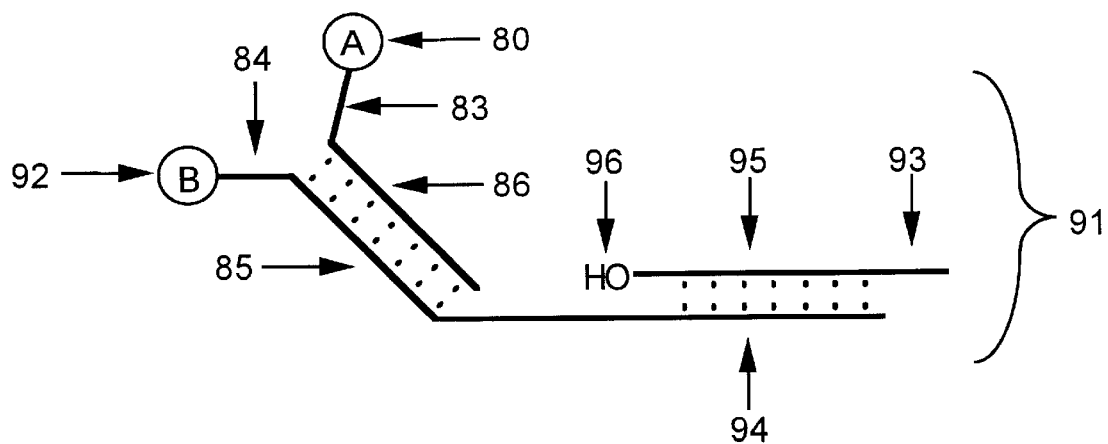

SEQUENCE LISTING

<160> NUMBER OF SEQ ID NOS: 16

<210> SEQ ID NO 1
<211> LENGTH: 24
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-Biotin
<220> FEATURE:
<223> OTHER INFORMATION: Description of Artificial Sequence:PCR Primer

<400> SEQUENCE: 1
gtggtagttg gagctggtgg cgta                                          24

<210> SEQ ID NO 2
<211> LENGTH: 33
<212> TYPE: DNA
<213> ORGANISM: Artificial Sequence
<220> FEATURE:
<221> NAME/KEY: misc_feature
<222> LOCATION: (1)
<223> OTHER INFORMATION: 5' - Fluorescein
<220> FEATURE:
<223> OTHER INFORMATION: Description of Artificial Sequence:PCR Primer

<400> SEQUENCE: 2
tcattcgcaa tcaatgactg aatataaact tgt                                33

<210> SEQ ID NO 3
<211> LENGTH: 33
<212> TYPE: DNA
<213> ORGANISM: Artificial Sequence
<220> FEATURE:
<221> NAME/KEY: misc_feature
<222> LOCATION: (1)
<223> OTHER INFORMATION: 5' -fluoreseein
<220> FEATURE:
<223> OTHER INFORMATION: Description of Artificial Sequence:PCR Primer

<400> SEQUENCE: 3
tcattcgcaa tcactctatt gttggatcat att                                33

```
<210> SEQ ID NO 4
<211> LENGTH: 111
<212> TYPE: DNA
<213> ORGANISM: Artificial Sequence
<220> FEATURE:
<221> NAME/KEY: misc_feature
<222> LOCATION: (1)..(111)
<223> OTHER INFORMATION: amplified region of k-ras plasmid
<220> FEATURE:
<223> OTHER INFORMATION: Description of Artificial Sequence:PCR Amplicon

<400> SEQUENCE: 4
atgactgaat ataaacttgt ggtagttgga gctggtggcg taggcaagag tgccttgacg      60
attcagctaa ttcagaatca ttttgtggac gaatatgatc caacaataga g              111

<210> SEQ ID NO 5
<211> LENGTH: 111
<212> TYPE: DNA
<213> ORGANISM: Artificial Sequence
<220> FEATURE:
<221> NAME/KEY: misc_feature
<222> LOCATION: (1)..(111)
<223> OTHER INFORMATION: amplified region only
<220> FEATURE:
<223> OTHER INFORMATION: Description of Artificial Sequence:PCR Amplicon

<400> SEQUENCE: 5
ctctattgtt ggatcatatt cgtccacaaa atgattctga attagctgta tcgtcaaggc      60
actcttgcct acgccaccag ctccaactac acaagtttta tattcagtca t              111

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:PCR Primer

<400> SEQUENCE: 6
atgactgaat ataaacttgt                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:PCR Primer

<400> SEQUENCE: 7
cactatcgac tacgcgatca                                                  20

<210> SEQ ID NO 8
<211> LENGTH: 33
<212> TYPE: DNA
<213> ORGANISM: Artificial Sequence
<220> FEATURE:
<221> NAME/KEY: misc_feature
<222> LOCATION: (1)
<223> OTHER INFORMATION: 5' Rhodamine
<220> FEATURE:
<223> OTHER INFORMATION: Description of Artificial Sequence:PCR Primer

<400> SEQUENCE: 8
tcattcgcaa tcataggtta gggccgttga gca                                   33

<210> SEQ ID NO 9
<211> LENGTH: 274
<212> TYPE: DNA
```

<210> SEQ ID NO 9
<211> LENGTH: 274
<212> TYPE: DNA
<213> ORGANISM: Artificial Sequence
<220> FEATURE:
<221> NAME/KEY: misc_feature
<222> LOCATION: (1)..(274)
<223> OTHER INFORMATION: amplified region of plasmid
<220> FEATURE:
<223> OTHER INFORMATION: Description of Artificial Sequence:PCR Amplicon

<400> SEQUENCE: 9

```
cactatcgac tacgcgatca tggcgaccac acccgtcctg tggatcctct acgccggacg      60
catctgggcc ggcatcaccg gcgccacagg tgcggttgct ggcgcctata tcgccgacat     120
caccgatggg gaagatcggg ctgcccactt cgggctcatg agcgcttgtt tcggcgtggg     180
tatggtggca ggccccgtgg ccgggggact gttgggcgcc atctccttgc atgcaccatt     240
ccttgaggcg gcggtgctca acggcctcaa ccta                                  274
```

<210> SEQ ID NO 10
<211> LENGTH: 274
<212> TYPE: DNA
<213> ORGANISM: Artificial Sequence
<220> FEATURE:
<221> NAME/KEY: misc_feature
<222> LOCATION: (1)..(274)
<223> OTHER INFORMATION: amplified region of plasmid
<220> FEATURE:
<223> OTHER INFORMATION: Description of Artificial Sequence:PCR Amplicon

<400> SEQUENCE: 10

```
taggttgagg ccgttgagca ccgccgccgc aaggaatggt gcatgcaagg agatggcgcc      60
caacagtccc ccggccacgg ggcctgccac catacccacg ccgaaacaag cgctcatgag     120
cccgaagtgg cgagcccgat cttccccatc ggtgatgtcg gcgataggg cgccagcaac     180 cgcacctgtg gcgccggtga tgccggccac gatgcgtccg gcgtagagga tccacaggac     240
gggtgtggtc gccatgatcg cgtagtcgat agtg                                  274
```

<210> SEQ ID NO 11
<211> LENGTH: 28
<212> TYPE: DNA
<213> ORGANISM: Artificial Sequence
<220> FEATURE:
<221> NAME/KEY: misc_feature
<222> LOCATION: (1)
<223> OTHER INFORMATION: 5' - Fluorescein
<220> FEATURE:
<223> OTHER INFORMATION: Description of Artificial Sequence:PCR Primer

<400> SEQUENCE: 11

```
tcattcgcaa tcaacgccac cagctcca                                         28
```

<210> SEQ ID NO 12
<211> LENGTH: 28
<212> TYPE: DNA
<213> ORGANISM: Artificial Sequence
<220> FEATURE:
<221> NAME/KEY: misc_feature
<222> LOCATION: (1)
<223> OTHER INFORMATION: 5'- fluorescein
<220> FEATURE:
<223> OTHER INFORMATION: Description of Artificial Sequence:PCR Primer

<400> SEQUENCE: 12

```
tcattcgcaa tcaacgccac aagctcaa                                         28
```

<210> SEQ ID NO 13
<211> LENGTH: 17

```
<212> TYPE: DNA
<213> ORGANISM: Artificial Sequence
<220> FEATURE:
<223> OTHER INFORMATION: Description of Artificial Sequence:PCR Primer

<400> SEQUENCE: 13
gttttcccag tcacgac                                                17

<210> SEQ ID NO 14
<211> LENGTH: 170
<212> TYPE: DNA
<213> ORGANISM: Artificial Sequence
<220> FEATURE:
<221> NAME/KEY: misc_feature
<222> LOCATION: (1)..(170)
<223> OTHER INFORMATION: amplified region of plasmid
<220> FEATURE:
<223> OTHER INFORMATION: Description of Artificial Sequence:PCR Amplicon

<400> SEQUENCE: 14
acgccaccag ctccaactac cacaagttta tattcagtca tttcgaattc tgcagatatc    60
catcacactg gcggccgctc gagcatgcat ctagagggcc caattcgccc tatagtgagt   120
cgtattacaa ttcactggcc gtcgttttac aacgtcgtga ctgggaaaac               170

<210> SEQ ID NO 15
<211> LENGTH: 170
<212> TYPE: DNA
<213> ORGANISM: Artificial Sequence
<220> FEATURE:
<221> NAME/KEY: misc_feature
<222> LOCATION: (1)..(170)
<223> OTHER INFORMATION: amplified region of plasmid
<220> FEATURE:
<223> OTHER INFORMATION: Description of Artificial Sequence:PCR Amplicon

<400> SEQUENCE: 15
gttttcccag tgacgacgtt gtaaaacgac ggccagtgaa ttgtaatacg actcactata    60
gggcgaattg ggccctctag atgcatgctc gagcggccgc cagtgtgatg gatatctgca   120
gaattcgaaa tgactgaata taaacttgtg gtagttggag ctggtggcgt               170

<210> SEQ ID NO 16
<211> LENGTH: 33
<212> TYPE: DNA
<213> ORGANISM: Artificial Sequence
<220> FEATURE:
<221> NAME/KEY: misc_feature
<222> LOCATION: (1)
<223> OTHER INFORMATION: 5'-dabcyl
<220> FEATURE:
<223> OTHER INFORMATION: Description of Artificial Sequence:PCR Primer

<400> SEQUENCE: 16
tcattcgcaa tcactctatt gttggatcat att                                33
```

METHOD, KITS AND COMPOSITIONS PERTAINING TO DETECTION COMPLEXES

CROSS REFERENCE TO RELATED APPLICATIONS

This application claims the benefit of U.S. Provisional Application No. 60/079,211 filed on Mar. 24, 1998.

BACKGROUND OF THE INVENTION

1. Field of the Invention

This invention is related to the field of probe-based or primer-based target sequence detection, analysis and quantitation. More specifically, this invention relates to novel methods, kits and compositions pertaining to Detection Complexes wherein said methods, kits and compositions are used to generate detectable signal which is indicative of the presence, absence or quantity of one or more target sequences or target molecules of interest in a sample.

2. Description of the Related Art

Quenching of fluorescence signal can occur by either Fluorescence Resonance Energy Transfer "FRET" (also known as non-radiative energy transfer: See: Yaron et al., *Analytical Biochemistry* 95: 228–235 (1979) at p. 232, col. 1, lns. 32–39) or by non-FRET interactions (also known as radiationless energy transfer; See: Yaron et al., *Analytical Biochemistry*, 95 at p. 229, col. 2, lns. 7–13). The critical distinguishing factor between FRET and non-FRET quenching is that non-FRET quenching requires short range interaction by "collision" or "contact" and therefore requires no spectral overlap between the moieties of the donor and acceptor pair (See: Yaron et al., *Analytical Biochemistry* 95 at p. 229, col. 1, lns. 22–42). Conversely, FRET quenching requires spectral overlap between the donor and acceptor moieties and the efficiency of quenching is directly proportional to the distance between the donor and acceptor moieties of the FRET pair (See: Yaron et al., *Analytical Biochemistry*, 95 at p. 232, col. 1, ln. 46 to col. 2, ln. 29). Extensive reviews of the FRET phenomenon are described in Clegg, R. M., *Methods Enzymol.*, 221: 353–388 (1992) and Selvin, P. R., *Methods Enzymol.*, 246: 300–334 (1995). Yaron et al. also suggested that the principles described therein might be applied to the hydrolysis of oligonucleotides (See: Yaron et al., *Analytical Biochemistry*, 95 at p. 234, col. 2, lns. 14–18).

The FRET phenomenon has been utilized for the direct detection of nucleic acid target sequences without the requirement that labeled nucleic acid hybridization probes or primers be separated from the hybridization complex prior to detection (See: Livak et al., U.S. Pat. No. 5,538,848). One method utilizing FRET to analyze Polymerase Chain Reaction (PCR) amplified nucleic acid in a closed tube format is commercially available from Perkin Elmer. The TaqMan™ assay utilizes a nucleic acid hybridization probe which is labeled with a fluorescent reporter and a quencher moiety in a configuration which results in quenching of fluorescence in the intact probe. During the PCR amplification, the probe sequence specifically hybridizes to the amplified nucleic acid. When hybridized, the exonuclease activity of the Taq polymerase degrades the probe thereby eliminating the intramolecular quenching maintained by the intact probe. Because the probe is designed to hybridize specifically to the amplified nucleic acid, the increase in fluorescence intensity of the sample, caused by enzymatic degradation of the probe, can be correlated with the activity of the amplification process.

Nonetheless, this method preferably requires that each of the fluorophore and quencher moieties be located on the 3' and 5' termini of the probe so that the optimal signal to noise ratio is achieved (See: Nazarenko et al., *Nucl. Acids Res.*, 25: 2516–2521 (1997) at p. 2516, col. 2, lns. 27–35). However, this orientation necessarily results in less than optimal fluorescence quenching because the fluorophore and quencher moieties are separated in space and the transfer of energy is most efficient when they are close. Consequently, the background emission from unhybridized probe can be quite high in the TaqMan™ assay (See: Nazarenko et al., *Nucl. Acids Res.*, 25: at p. 2516, col. 2, lns. 36–40).

The nucleic acid Molecular Beacon is another construct which utilizes the FRET phenomenon to detect target nucleic acid sequences (See: Tyagi et al., *Nature Biotechnology*, 14: 303–308 (1996)). A nucleic acid Molecular Beacon comprises a probing sequence embedded within two complementary arm sequences (See: Tyagi et al., *Nature Biotechnology*, 14: at p. 303, col. 1, lns. 22–30). To each termini of the probing sequence is attached one of either a fluorophore or quencher moiety. In the absence of the nucleic acid target, the arm sequences anneal to each other to thereby form a loop and hairpin stem structure which brings the fluorophore and quencher together (See: Tyagi et al., *Nature Biotechnology*, 14: at p. 304, col. 2, lns. 14–25). When contacted with target nucleic acid, the complementary probing sequence and target sequence will hybridize. Because the hairpin stem cannot coexist with the rigid double helix that is formed upon hybridization, the resulting conformational change forces the arm sequences apart and causes the fluorophore and quencher to be separated (See: Tyagi et al., *Nature Biotechnology*, 14: at p. 303, col. 2, lns. 1–17). When the fluorophore and quencher are separated, energy of the donor fluorophore does not transfer to the acceptor moiety and the fluorescent signal is then detectable. Since unhybridized "Molecular Beacons" are non-fluorescent, it is not necessary that any excess probe be removed from an assay. Consequently, Tyagi et al. state that Molecular Beacons can be used for the detection of target nucleic acids in a homogeneous assay and in living cells. (See: Tyagi et al., *Nature Biotechnology*, 14: at p. 303, col. 2; lns. 15–77).

The arm sequences of the disclosed nucleic acid Molecular Beacon constructs are unrelated to the probing sequence (See: Tyagi et al., *Nature Biotechnology*, 14: at p. 303, col. 1; ln. 30). Because the Tyagi et al. Molecular Beacons comprise nucleic acid molecules, proper stem formation and stability is dependent upon the length of the stem, the G:C content of the arm sequences, the concentration of salt in which it is dissolved and the presence or absence of magnesium in which the probe is dissolved (See: Tyagi et al., *Nature Biotechnology*, 14: at p. 305, col. 1; lns. 1–16). Furthermore, the Tyagi et al. nucleic acid Molecular Beacons are susceptible to degradation by endonucleases and exonucleases.

Upon probe degradation, background fluorescent signal will increase since the donor and acceptor moieties are no longer held in close proximity. Therefore, assays utilizing enzymes known to have nuclease activity, will exhibit a continuous increase in background fluorescence as the nucleic acid Molecular Beacon is degraded (See: FIG. 7 in Tyagi et al: the data associated with (○) and (□) demonstrates that the fluorescent background, presumably caused by probe degradation, increases with each amplification cycle.) Additionally, nucleic acid Molecular Beacons will also, at least partially, be degraded in living cells because cells contain active nuclease activity.

The constructs described by Tyagi et al. are more broadly described in WO95/13399 (hereinafter referred to as "Tyagi2 et al.") except that Tyagi2 et al. also discloses that the nucleic acid Molecular Beacon may also be bimolecular wherein they define bimolecular as being unitary probes of the invention comprising two molecules (e.g. oligonucleotides) wherein half, or roughly half, of the target complement sequence, one member of the affinity pair and one member of the label pair are present in each molecule (See: Tyagi2 et al., p. 8, ln. 25 to p. 9, ln. 3). However, Tyagi2 et al. specifically states that in designing a unitary probe for use in a PCR reaction, one would naturally choose a target complement sequence that is not complementary to one of the PCR primers (See: Tyagi2 et al., p. 41, ln. 27). Assays of the invention include real-time and end-point detection of specific single-stranded or double stranded products of nucleic acid synthesis reactions, provided however that if unitary probes will be subjected to melting or other denaturation, the probes must be unimolecular (See: Tyagi2 et al., p. 37, lns. 1–9). Furthermore, Tyagi2 et al. stipulate that although the unitary probes of the invention may be used with amplification or other nucleic acid synthesis reactions, bimolecular probes (as defined in Tyagi2 et al.) are not suitable for use in any reaction (e.g. PCR) wherein the affinity pair would be separated in a target-independent manner (See: Tyagi2 et al., p. 13, lns. 9–12). Neither Tyagi et al. nor Tyagi2 et al. disclose, suggest or teach anything about PNA.

In a more recent disclosure, modified hairpin constructs which are similar to the Tyagi et al. nucleic acid Molecular Beacons, but which are suitable as primers for polymerase extension, have been disclosed (See: Nazarenko et al., *Nucleic Acids Res.*, 25: 2516–2521(1997)). A method suitable for the direct detection of PCR-amplified DNA in a closed system is also disclosed. According to the method, the Nazarenko et al. primer constructs are, by operation of the PCR process, incorporated into the amplification product. Incorporation into a PCR amplified product results in a change in configuration which separates the donor and acceptor moieties. Consequently, increases in the intensity of the fluorescent signal in the assay can be directly correlated with the amount of primer incorporated into the PCR amplified product. The authors conclude, this method is particularly well suited to the analysis of PCR amplified nucleic acid in a closed tube format.

Because they are nucleic acids, the Nazarenko et al. primer constructs are admittedly subject to nuclease digestion thereby causing an increase in background signal during the PCR process (See: Nazarenko et al., *Nucleic Acids Res.*, 25: at p. 2519, col. 1; lns. 28–39). An additional disadvantage of this method is that the Molecular Beacon like primer constructs must be linearized during amplification (See: Nazarenko et al., *Nucleic Acids Res.*, 25: at p. 2519, col. 1, lns. 7–8). Consequently, the polymerase must read through and dissociate the stem of the hairpin modified Molecular Beacon like primer construct if fluorescent signal is to be generated. Therefore, the stem must be designed so that its stability does not inhibit the polymerase activity. Nazarenko et al. does not suggest, teach or disclose anything about PNA.

In still another application of FRET to target nucleic acid sequence detection, doubly labeled fluorescent oligonucleotide probes which have been rendered impervious to exonuclease digestion have also been used to detect target nucleic acid sequences in PCR reactions and in-situ PCR (See: Mayrand, U.S. Pat. No. 5,691,146). The oligonucleotide probes of Mayrand comprise a fluorescer (reporter) molecule attached to a first end of the oligonucleotide and a quencher molecule attached to the opposite end of the oligonucleotide (See: Mayrand, Abstract). Mayrand suggests that the prior art teaches that the distance between the fluorophore and quencher is an important feature which must be minimized and consequently the preferred spacing between the reporter and quencher moieties of a DNA probe should be 6–16 nucleotides (See: col. 7, lns. 8–24). Mayrand, however teaches that the reporter molecule and quencher moieties are preferably located at a distance of 18 nucleotides (See: col. 3, lns 35–36) or 20 bases (See: col. 7, lns. 25–46) to achieve the optimal signal to noise ratio. Consequently, both Mayrand and the prior art cited therein teach that the detectable properties of nucleic acid probes (DNA or RNA) comprising a fluorophore and quencher exhibit a strong dependence on probe length.

Resistance to nuclease digestion is also an important aspect of the invention (See: U.S. Pat. No. 5,691,146 at col. 6, lns. 42–64) and therefore, Mayrand suggests that the 5' end of the oligonucleotide may be rendered impervious to nuclease digestion by including one or more modified intemucleotide linkages (See: U.S. Pat. No. 5,691,146 at col. 6, lns. 45–50). Furthermore, Mayrand suggests that a polyamide nucleic acid (PNA) or peptide can be used as a nuclease resistant linkage to thereby modify the 5' end of the oligonucleotide probe of the invention and render it impervious to nuclease digestion (See: U.S. Pat. No. 5,691,146 at col. 6, lns. 53–64). Mayrand does not however, disclose, suggest or teach that a PNA probe construct might be a suitable substitute for the practice of the invention despite having obvious knowledge of its existence. Furthermore, Mayrand does not teach one of skill in the art how to prepare and/or label a PNA with the fluorescer or quencher moieties.

The efficiency of energy transfer between donor and acceptor moieties as they can be influenced by oligonucleotide length (distance) has been further examined and particularly applied to fluorescent nucleic acid sequencing applications (See: Mathies et al., U.S. Pat. No. 5,707,804). Mathies et al. states that two fluorophores will be joined by a backbone or chain where the distance between the two fluorophores may be varied (See: U.S. Pat. No. 5,707,804 at col. 4, lns. 1–3). Thus, the distance must be chosen to provide energy transfer from the donor to the acceptor through the well-known Foerster mechanism (See: U.S. Pat. No. 5,707,804 at col. 4, lns. 7–9). Preferably about 3–10 nucleosides separate the fluorophores of a single stranded nucleic acid (See: U.S. Pat. No. 5,707,804 at col. 7, lns. 21–25). Mathies et al. does not suggest, teach or disclose anything about PNA.

From the analysis of DNA duplexes is has been observed that: 1: the efficiency of FET (or FRET as defined herein) appears to depend somehow on the nucleobase sequence of the oligonucleotide; 2: donor fluorescence changes in a manner which suggests that dye-DNA interactions affect the efficiency of FET; and 3: the Forster equation does not quantitatively account for observed energy transfer and therefore the length between donor and acceptor moieties attached to oligonucleotides cannot be quantitated, though it can be used qualitatively (See: Promisel et al., *Biochemistry*, 29: 9261–9268 (1990). Promisel et al. suggest that non-Forster effects may account for some of their observed but otherwise unexplainable results (See: Promisel et al., *Biochemistry*, 29: at p. 9267, col. 1, ln. 43 to p. 9268, col. 1, ln. 13). The result et al. suggest that the FRET phenomena when utilized in nucleic acids is not entirely predictable or well understood. Promisel et al. does not suggest, teach or disclose anything about PNA and, in fact, the manuscript predates the invention of PNA.

The background art thus far discussed does not disclose, suggest or teach anything about PNA oligomers to which are directly attached a pair of donor and acceptor moieties. In fact, the FRET phenomenon as applied to the detection of nucleic acids, appears to be confined to the preparation of constructs in which the portion of the probe which is complementary to the target nucleic acid sequence is itself comprised solely of nucleic acid.

FRET has also been utilized within the field of peptides. (See: Yaron et al. *Analytical Biochemistry* 95 at p. 232, col. 2, ln. 30 to p. 234, col. 1, ln. 30). Indeed, the use of suitably peptides as enzyme substrates appears to be the primary utility for peptides which are labeled with donor and acceptor pairs (See: Zimmerman et al., *Analytical Biochemistry*, 70: 258–262 (1976), Carmel et al., *Eur. J. Biochem.*, 73: 617–625 (1977), Ng et al., *Analytical Biochemistry*, 183: 50–56 (1989), Wang et al., *Tett. Lett.*, 31: 6493–6496 (1990) and Meldal et al., *Analytical Biochemistry*, 195: 141–147 (1991). Early work suggested that quenching efficiency of the donor and acceptor pair was dependent on peptide length (See: Yaron et al., *Analytical Biochemistry* 95 at p. 233, col. 2, lns. 36–40). However, the later work has suggested that efficient quenching was not so dependent on peptide length (See: Ng et al., *Analytical Biochemistry*, 183: at p. 54, col. 2, ln 23 to p. 55, col. 1, ln. 12; Wang et al., *Tett. Lett.*, 31 wherein the peptide is eight amino acids in length; and Meldal et al. *Analytical Biochemistry*, 195 at p. 144, col. 1, lns. 33–37). It was suggested by Ng et al. that the observed quenching in long peptides might occur by an as yet undetermined mechanism (See: Ng et al., *Analytical Biochemistry* 183 at p. 55, col. 1, ln 13 to col. 2, ln 7.)

Despite its name, peptide nucleic acid (PNA) is neither a peptide, a nucleic acid nor is it even an acid. Peptide Nucleic Acid (PNA) is a non-naturally occurring polyamide (pseudopeptide) which can hybridize to nucleic acid (DNA and RNA) with sequence specificity (See U.S. Pat. Nos. 5,539,082, 5,527,675, 5,623,049, 5,714,331, 5,736,336, 5,773,571, 5,786,461 and Egholm et al., *Nature* 365: 566–568 (1993)). PNAs are synthesized by adaptation of standard peptide synthesis procedures in a format which is now commercially available. (For a general review of the preparation of PNA monomers and oligomers please see: Dueholm et al., *New J. Chem.*, 21: 19–31 (1997) or Hyrup et. al., *Bioorganic & Med. Chem.* 4: 5–23 (1996)). Alternatively, labeled and unlabeled PNA oligomers can be purchased (See: PerSeptive Biosystems Promotional Literature: BioConcepts, Publication No. NL612, Practical PNA, Review and Practical PNA, Vol. 1, Iss. 2).

Being non-naturally occurring molecules, unmodified PNAs are not known to be substrates for the enzymes which are known to degrade peptides or nucleic acids. Therefore, unmodified PNAs should be stable in biological samples, as well as have a long shelf-life. Likewise, when complexed to a nucleic acid, PNAs shield the nucleic acid from degradation (See: WIPO patent application: Stanley et al., WO95/15974). Unlike nucleic acid hybridization which is very dependent on ionic strength, the hybridization of a PNA with a nucleic acid is fairly independent of ionic strength and is favored at low ionic strength, conditions which strongly disfavor the hybridization of nucleic acid to nucleic acid (Egholm et al., *Nature*, at p. 567). The effect of ionic strength on the stability and conformation of PNA complexes has been extensively investigated (Tomac et al., *J. Am. Chem. Soc.*, 118: 5544–5552 (1996)). Sequence discrimination is more efficient for PNA recognizing DNA than for DNA recognizing DNA (Egholm et al., *Nature*, at p. 566). However, the advantages in point mutation discrimination with PNA probes, as compared with DNA probes, in a hybridization assay appears to be somewhat sequence dependent (Nielsen et al., *Anti-Cancer Drug Design* 8: 53–65, (1993) and Weiler et al., *Nucl. Acids Res.* 25: 2792–2799 (1997)). As an additional advantage, PNAs hybridize to nucleic acid in both a parallel and antiparallel orientation, though the antiparallel orientation is preferred (See: Egholm et al., *Nature* at p. 566).

Despite the ability to hybridize to nucleic acid in a sequence specific manner, there are many differences between PNA probes and standard nucleic acid probes. These differences can be conveniently broken down into biological, structural, and physico-chemical differences. As discussed in more detail below, these biological, structural, and physico-chemical differences may lead to unpredictable results when attempting to use PNA probes in applications where were nucleic acids have typically been employed. This non-equivalency of differing compositions is often observed in the chemical arts.

With regard to biological differences, nucleic acids, are biological materials that play a central role in the life of living species as agents of genetic transmission and expression. Their in vivo properties are fairly well understood. PNA, on the other hand is recently developed totally artificial molecule, conceived in the minds of chemists and made using synthetic organic chemistry. PNA has no known biological function and native (unmodified) PNA is not known to be a substrate for any polymerase, ligase, nuclease or protease.

Structurally, PNA also differs dramatically from nucleic acid. Although both can employ common nucleobases (A, C, G, T, and U), the backbones of these molecules are structurally diverse. The backbones of RNA and DNA are composed of repeating phosphodiester ribose and 2-deoxyribose units. In contrast, the backbones of the most common PNAs are composed of N-[2-(arninoethyl)]glycine subunits. Additionally, in PNA the nucleobases are connected to the backbone by an additional methylene carbonyl moiety.

PNA is not an acid and therefore contains no charged acidic groups such as those present in DNA and RNA. Because they lack formal charge, PNAs are generally more hydrophobic than their equivalent nucleic acid molecules. The hydrophobic character of PNA allows for the possibility of non-specific (hydrophobic/hydrophobic interactions) interactions not observed with nucleic acids. Further, PNA is achiral, providing it with the capability of adopting structural conformations the equivalent of which do not exist in the RNA/DNA realm.

The unique structural features of PNA result in a polymer which is highly organized in solution, particularly for purine rich polymers (See: Dueholm et al., *New J. Chem.*, 21: 19–31 (1997) at p. 27, col. 2 lns. 6–30). Conversely, a single stranded nucleic acid is a random coil which exhibits very little secondary structure. Because PNA is highly organized, PNA should be more resistant to adopting alternative secondary structures (e.g. a hairpin stem and/or loop).

The physico/chemical differences between PNA and DNA or RNA are also substantial. PNA binds to its complementary nucleic acid more rapidly than nucleic acid probes bind to the same target sequence. This behavior is believed to be, at least partially, due to the fact that PNA lacks charge on its backbone. Additionally, recent publications demonstrate that the incorporation of positively charged groups into PNAs will improve the kinetics of hybridization (See: Iyer et al., *J. Biol. Chem.* 270: 14712–14717 (1995)). Because it lacks charge on the backbone, the stability of the PNA/nucleic acid complex is higher than that of an analogous DNA/DNA or RNA/DNA complex. In certain situations, PNA will form highly stable triple helical complexes through a process called "strand displacement". No equivalent strand displacement processes or structures are known in the DNA/RNA world.

Recently, the "Hybridization based screening on peptide nucleic acid (PNA) oligomer arrays" has been described wherein arrays of some 1000 PNA oligomers of individual sequence were synthesized on polymer membranes (See: Weiler et al., *Nucl. Acids Res.*, 25: 2792–2799(1997)). Arrays are generally used, in a single assay, to generate affinity binding (hybridization) information about a specific sequence or sample to numerous probes of defined composition. Thus, PNA arrays may be useful in diagnostic applications or for screening libraries of compounds for leads which might exhibit therapeutic utility. However, Weiler et al. note that the affinity and specificity of DNA hybridization to immobilized PNA oligomers depended on hybridization conditions more than was expected. Moreover, there was a tendency toward non-specific binding at lower ionic strength. Furthermore, certain very strong binding mismatches were identified which could not be eliminated by more stringent washing conditions. These unexpected results are illustrative of the lack of complete understanding of these newly discovered molecules (i.e. PNA).

In summary, because PNAs hybridize to nucleic acids with sequence specificity, PNAs are useful candidates for investigation as substitute probes when developing probe-based hybridization assays. However, PNA probes are not the equivalent of nucleic acid probes in both structure or function. Consequently, the unique biological, structural, and physico-chemical properties of PNA requires that experimentation be performed to thereby examine whether PNAs are suitable in applications where nucleic acid probes are commonly utilized.

SUMMARY OF THE INVENTION

This invention is directed to methods, kits and compositions which are used to detect the presence, absence or quantity of a target sequence and/or target molecule in a sample of interest. The preferred compositions of the invention are Detection Complexes, PCR Detection Complexes and Substrate Detection Complexes which are hybrids of at least two component polymers. At least two of the component polymers of the Detection Complex comprise at least one moiety from a set of donor and acceptor moieties, though the Detection Complex may comprise more than one set of donor and acceptor moieties and/or more than two component polymers. Component polymers are designed to form the Detection Complex by the interaction of interacting groups. Additionally, the Detection Complex may comprise one or more linkers and/or one or more spacer moieties as may be useful to construct a Detection Complex suitable for a particular application.

When the Detection Complex, PCR Detection Complex or Substrate Detection Complex is formed, at least one donor moiety of one component polymer is brought sufficiently close in space to at least one acceptor moiety of a second component polymer. Since the donor and acceptor moieties of the set of the assembled Detection Complex are closely situated in space, transfer of energy occurs between moieties of the set. When the Detection Complex dissociates, the donor and acceptor moieties do not interact sufficiently to cause substantial transfer of energy from the donor and acceptor moieties of the set. Consequently, Detection Complex formation/dissociation can be determined by measuring at least one physical property of at least one member of the set which is detectably different when the complex is formed as compared with when the component polymers of the Detection Complex, PCR Detection Complex or Substrate Detection Complex exist independently and unassociated.

The Detection Complexes and PCR Detection Complexes of this invention are primarily designed to dissociate as a direct or indirect consequence of the hybridization of one or more segments of a component polymer to a target sequence of a target molecule. Consequently, the Detection Complexes and PCR Detection Complexes can be used to detect the presence, absence or quantity of a target molecule of interest, which may be present in a sample of interest. The presence, absence or quantity of target molecule can then be determined by directly or indirectly correlating the dissociation of Detection Complex or PCR Detection Complex with the hybridization of a component polymer to the target sequence or priming site. Because the component polymers of a Detection Complex will preferably dissociate, the attached donor and acceptor moieties, which are independently attached to different polymers, can become far more separated in space as compared with unimolecular "Beacon" probes such as Molecular Beacons (PNA or nucleic acid) or Linear Beacons. As a consequence, the efficiency of energy transfer, which is proportional to the distance between the donor and acceptor moieties, will be far more substantially altered as compared with unimolecular probes wherein the donor and acceptor moieties are linked to the same polymer and therefore cannot be infinitely separated in space. Thus, the Detection Complexes and PCR Detection Complexes of this invention possess a substantial comparative advantage over unimolecular "Beacon" probes.

Though primarily designed to dissociate, the distance between donor and acceptor moieties may change merely because the probing segment of a probing polymer of a Detection Complex hybridizes to a target sequence whether or not the Detection Complex dissociates. Consequently, the energy transfer between donor and acceptor moieties of a set may be affected even though the Detection Complex does not dissociate provided there is a detectable change in at least one physical property of at least one member of a set which is detectably different in the native Detection Complex as compared with when the still intact Detection Complex is further complexed to a target sequence of a target molecule. Thus, the Detection Complexes of this invention may also be used to determine the presence absence or quantity of a target sequence or target molecule in a sample even though the Detection Complex does not dissociate.

Thus, in one embodiment, this invention is directed to Detection Complexes suitable for detecting or identifying the presence, absence or quantity of a target sequence and/or target molecule of interest in an assay. A Detection Complex comprises at least one probing polymer wherein the probing polymer has a probing segment which hybridizes to the target sequence, under suitable hybridization conditions, whether or not the Detection Complex dissociates. The probing polymer also has one or more interacting groups suitable for the formation of a complex with at least one other component polymer. The Detection Complex also comprises at least one annealing polymer which, at a minimum, has one or more interacting groups wherein the interaction of the interacting groups of the two or more component polymers form and stabilize the complex. The Detection Complex also comprises at least one set of donor and acceptor moieties. To each of at least two component polymers is linked at least one donor and one acceptor moiety such that formation of the complex facilitates transfer of energy between donor and acceptor moieties of each set in a manner which is detectably different from when the component polymers exist independently or unassociated or when the complex is free in solution as compared to when it is further complexed to a target sequence of a target molecule of interest. At least one of the component polymers of the Detection Complex is a non-nucleic acid polymer. The Detection Complex may exist in solution, may be immobilized to a support or may be one of two or more Detection Complexes arranged in an array.

In still another embodiment, this invention is directed to non-nucleic acid polymers which are labeled with only a quencher but not a donor moiety. Preferably, the quencher is dabcyl. In preferred embodiments the non-nucleic acid polymer is terminally labeled with the quencher and most preferably the non-nucleic acid polymer is C-terminally labeled with dabcyl. Non-limiting, examples of several C-terminally dabcyl labeled PNAs are found in Table 1. For the examples listed in Table 1, the dabcyl moiety is conveniently linked to the N-$\epsilon$-amino group of the C-terminal lysine amino acid though this is not a limitation since other methods of terminal attachment exist.

In still another embodiment, this invention is directed to Substrate Detection Complexes. Substrate Detection Complexes operate as a substrate for an enzyme to thereby generate changes in detectable signal in a target independent manner. A Substrate Detection Complex is very similar to the Detection Complexes hereinbefore described except the Substrate Detection Complex differs from a Detection Complex or PCR Detection Complex in that it does not contain a probing segment which hybridizes to a target sequence or priming site of a target molecule of interest. Thus, the Substrate Detection Complex does not directly interact with the target sequence or target molecule of interest. However, a Substrate Detection Complex, at a minimum, comprises at least two annealing polymers wherein at least one of the annealing polymers can interact with itself, another annealing polymer or another molecule in the assay to thereby form a substrate for an enzyme. The two or more annealing polymers further comprise interacting groups which form and stabilize the Substrate Detection Complex as well as linked donor and acceptor moieties.

The Detection Complexes, PCR Detection Complexes and Substrate Detection Complexes of this invention are suitable for detecting or identifying the presence, absence or quantity of a target sequence of a target molecule. Consequently, this invention is also directed to methods for the detection, identification or quantitation of a target sequence and/or target molecule in a sample.

In one embodiment, the method comprises contacting the sample with a Detection Complex or PCR Detection Complex and then detecting or identifying changes in detectable signal attributable to the transfer of energy between the donor and acceptor moieties of a Beacon Set upon hybridization or the probing segment of the probing polymer to the target sequence or upon direct or indirect dissociation of the complex. The signal detected can then be correlated with the presence, absence or quantity of the target sequence and/or target molecule in the sample. Generally, quantitation will involve comparison of the signal to a standard curve generated using a standardized assay and known quantities of target sequence and/or target molecule in representative samples.

In another embodiment, the method comprises forming the Detection Complex after the probing polymer or probing polymers have been allowed to interact with the target sequence or target molecule of interest. In this embodiment, the extent of formation of the Detection Complex can be measured by the change in detectable signal of at least one member of the Beacon Set before and after the formation of the Detection Complex. Since the amount of probing polymer or polymers and annealing polymer or polymers added to the sample can be controlled and calculated, the extent of formation of the Detection Complex, and the measurable change in detectable signal derived therefrom, can be used to determine the presence absence or quantity of a target sequence or target molecule in a sample of interest.

In still another embodiment, the Detection Complex is a substrate for an enzyme wherein the target molecule of interest is detected because the activity of the enzyme on the Substrate Detection Complex generates detectable signal in the presence of, or in proportion to, the presence or quantity of target molecule in the sample. The method comprises contacting the sample with probes and enzyme configured to generate target dependent enzyme activity. Generally, the assay is designed as a probe-based assay wherein at least one of the probes which complex with the target molecule is a probe-enzyme conjugate. The sample is then contacted with a Substrate Detection Complex and the changes in detectable signal attributable to the transfer of energy between the donor and acceptor moieties of a Beacon Set resulting from enzyme catalyzed dissociation of the complex are then measured. Generally, quantitation will involve comparison of the signal to a standard curve generated using a standardized assay and known quantities of target sequence and/or target molecule in representative samples.

In yet another embodiment, this invention is directed to a method for the formation of a Detection Complex, PCR Detection Complex or Substrate Detection Complex. Detection Complexes, PCR Detection Complexes and Substrate Detection Complexes are formed by mixing the two or more component polymers under conditions suitable for their interaction and assembly.

In still another embodiment, this invention is directed to kits which facilitate the useful practice of this invention. Thus, the preferred kits of this invention comprise one or more component polymers of a Detection Complex, PCR Detection Complex or Substrate Detection Complex and optionally other reagents useful for the practice of a method of this invention. Consequently, kits of this invention are suitable for detecting or identifying the presence, absence or quantity of a target sequence or target molecule which may be present in a sample of interest. As received by the end-user, the Detection Complex, PCR Detection Complex or Substrate Detection Complex may be preassembled or alternatively, the end-user may mix two or more of the component polymers to thereby generate the complex to be used with the kit.

In yet another embodiment, this invention is directed to a method for regenerating a support bound Detection Complex or an array of two or more support bound Detection Complexes. The method of regeneration comprises removing any hybridized target molecules from the surface and then contacting the surface with a quantity of at least one common labeled component polymer as is necessary to regenerate the one or many different Detection Complexes of the support or the array.

BRIEF DESCRIPTION OF THE DRAWINGS

FIGS. 1A–1C illustrate several different embodiments of Detection Complexes.

FIGS. 10A and 10B are graphical illustrations of fluorescence vs. temperature thermal profiles for Detection Complexes assembled from a PNA and a DNA oligomer wherein the Detection Complexes operated as the forward and reverse primers in a PCR reaction.

FIG. 19A is a graphic illustration of tabular data obtained for a multiplex PCR assay.

FIG. 19B is an electronic composite negative of the image of a photograph of an ethidium bromide stained gel.

FIGS. 20A and 20B illustrate two different embodiments of a Substrate Detection Complex.

DESCRIPTION OF THE PREFERRED EMBODIMENTS

Figure 2:
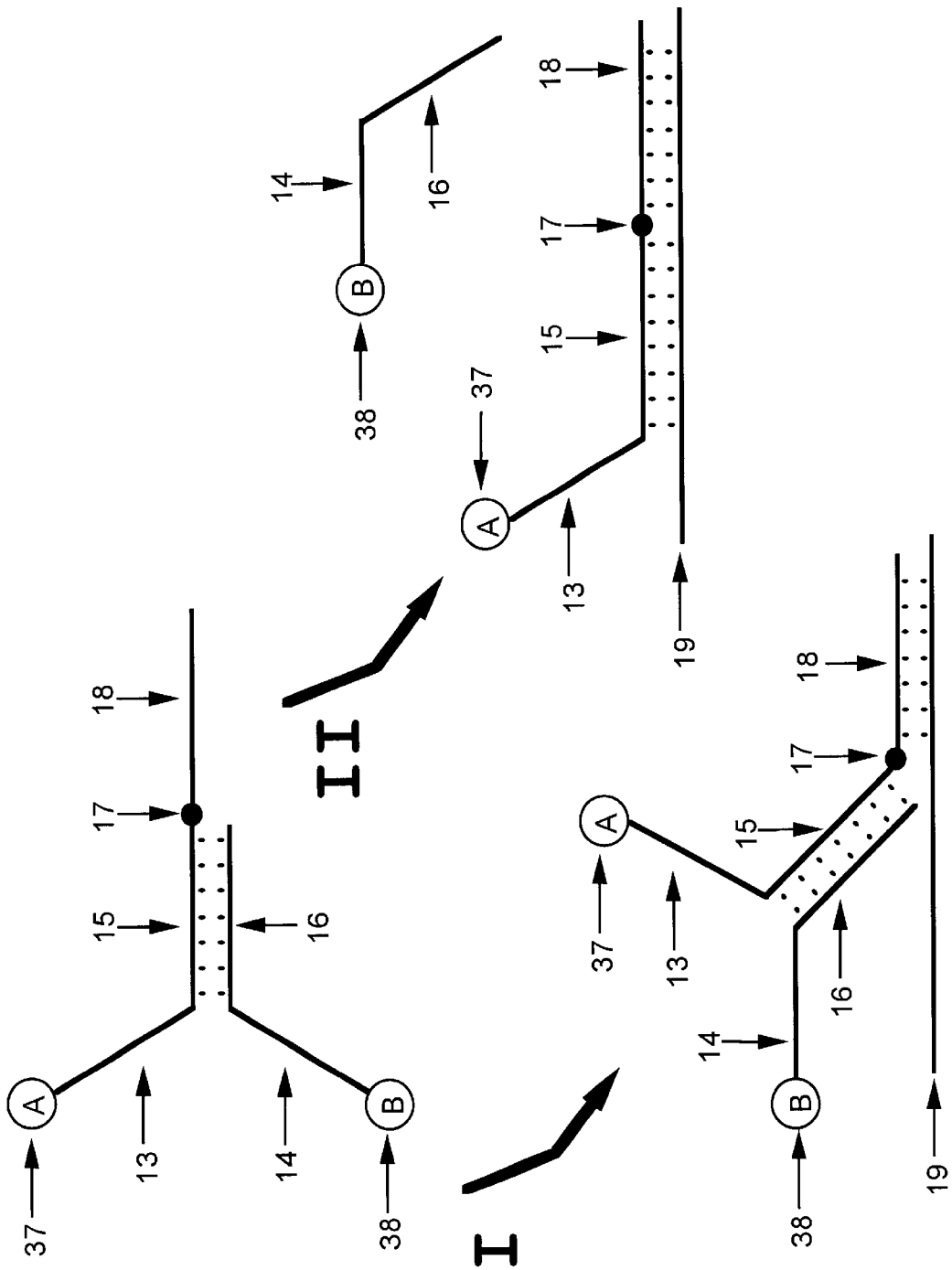
FIG. 2 illustrates several different embodiments for the hybridization of a probing sequence of a Detection Complex with a target sequence.

1. Definitions a. As used herein, the term "nucleobase" shall include those naturally occurring and those non-naturally occurring heterocyclic moieties commonly known to those who utilize nucleic acid technology or utilize peptide nucleic acid technology to thereby generate polymers which can sequence specifically bind to nucleic acids.

b. As used herein, the term "nucleobase sequence" is any segment of a polymer which comprises nucleobase containing subunits. Non-limiting examples of suitable polymers or polymers segments include oligodeoxynucleotides, oligoribonucleotides, peptide nucleic acids, nucleic acid analogs, nucleic acid mimics or chimeras.

c. As used herein, the term "target sequence" is any nucleobase sequence to be detected in an assay or otherwise used in the detection of a target molecule of interest in an assay. Thus, the "target sequence" may comprise the entire sequence of interest or may be a subsequence or subunit of a target molecule of interest. As used herein the "target sequence" may also refer to a priming site for a Detection Complex or PCR Detection Complex (as defined herein) of this invention.

d. As used herein, the term "target molecule of interest" may be a nucleic acid molecule of interest, a non-nucleic acid polymer, a PNA, or any other secondary composition, provided however, that the target sequence is linked to the secondary composition. Non-limiting examples of secondary compositions include peptides, enzymes, antibodies, antibody fragments and the like.

e. As used herein, the term "non-nucleic acid probe" or "non-nucleic acid polymer" shall mean an oligomer characterized in that it comprises a neutral backbone under suitable hybridization conditions. A preferred non-limiting example of a non-nucleic acid probe is a peptide nucleic acid (PNA) probe.

f. As used herein, the term "peptide nucleic acid" or "PNA" shall be defined as any oligomer, linked polymer or chimeric oligomer, comprising two or more PNA subunits (residues), including any of the compounds referred to or claimed as peptide nucleic acids in U.S. Pat. Nos. 5,539,082, 5,527,675, 5,623,049, 5,714,331, 5,736,336, 5,773,571 or 5,786,461 (all of which are herein incorporated by reference). The term "peptide nucleic acid" or "PNA" shall also apply to polymers comprising two or more subunits of those nucleic acid mimics described in the following publications: Diderichsen et al., *Tett. Lett.* 37: 475–478 (1996); Fujii et al., *Bioorg. Med. Chem. Lett.* 7: 637–627 (1997); Jordan et al., *Bioorg. Med. Chem. Lett.* 7: 687–690 (1997); Krotz et al., *Tett. Lett.* 36: 6941–6944 (1995); Lagriffoul et al., *Bioorg. Med. Chem. Lett.* 4: 1081–1082 (1994); Lowe et al., *J. Chem. Soc. Perkin Trans.* 1, (1997) 1: 539–546; Lowe et al., *J. Chem. Soc. Perkin Trans.* 11: 547–554 (1997); Lowe et al., *J. Chem. Soc. Perkin Trans.* 1 1:5 55–560 (1997); Petersen et al., *Bioorg. Med. Chem. Lett.* 6: 793–796 (1996); Diederichsen, U., *Bioorganic & Med. Chem. Lett.*, 8: 165–168 (1998); Cantin et al., *Tett. Lett.*, 38: 4211–4214 (1997); Ciapetti et al., *Tetrahedron*, 53: 1167–1176 (1997) and Lagriffoule et al., *Chem. Eur. J.*, 3: 912–919 (1997).

In preferred embodiments, a PNA is a polymer comprising two or more subunits of the formula:

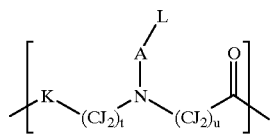

wherein, each J is the same or different and is selected from the group consisting of H, $R^1$, $OR^1$, $SR^1$, $NHR^1$, $NR^1_2$, F, Cl, Br and I. Each K is the same or different and is selected from the group consisting of O, S, NH and $NR^1$. Each $R^1$ is the same or different and is an alkyl group having one to five carbon atoms which may optionally contain a heteroatom or a substituted or unsubstituted aryl group. Each A is selected from the group consisting of a single bond, a group of the formula; —$(CJ_2)_s$— and a group of the formula; —$(CJ_2)_sC(O)$—, wherein, J is defined above and each s is an integer from one to five. The integer t is 1 or 2 and the integer u is 1 or 2. Each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl. In the most preferred embodiment, a PNA subunit consists of a naturally occurring or non-naturally occurring nucleobase attached to the aza nitrogen of the N-[2-(aminoethyl)]glycine backbone through a methylene carbonyl linkage.

g. As used herein, the terms "label" and "detectable moiety" shall be interchangeable and shall refer to moieties which can be attached to a nucleic acid polymer, non-nucleic acid probe or PNA probe to thereby render the probe or oligomer detectable by an instrument or method.

h. As used herein, the term "chimera" or "chimeric oligomer" shall mean an oligomer comprising two or more linked subunits which are selected from different classes of subunits. For example, a PNA/DNA chimera would comprise at least two PNA subunits linked to at least one 2'-deoxyribonucleic acid subunit (For exemplary methods and compositions related to PNA/DNA chimera preparation See: WO96/40709). Exemplary component subunits of the chimera are selected from the group consisting of PNA subunits, naturally occurring amino acid subunits, DNA subunits, RNA subunits and subunits of analogues or mimics of nucleic acids.

i. As used herein, the term "linked polymer" shall mean a polymer comprising two or more polymer segments which are linked by a linker. The polymer segments which are linked to form the linked polymer are selected from the group consisting of an oligodeoxynucleotide, an oligoribonucleotide, a peptide, a polyamide, a peptide nucleic acid (PNA) and a chimera.

j. As used herein the term "component polymer" or "component polymers" shall refer to the two or more polymers which assemble to form a Detection Complex. Non-limiting examples of suitable polymers include oligodeoxynucleotides, oligoribonucleotides, peptide nucleic acids, nucleic acid analogs, nucleic acid mimics, linked polymers or chimeras.

2. Detailed Description

I. General

PNA Synthesis:

Methods for the chemical assembly of PNAs are well known (See: U.S. Pat. Nos. 5,539,082, 5,527,675, 5,623,049, 5,714,331, 5,736,336, 5,773,571 or 5,786,571, herein incorporated by reference). Chemicals and instrumentation for the support bound automated chemical assembly of Peptide Nucleic Acids are now commercially available. Chemical assembly of a PNA is analogous to solid phase peptide synthesis, wherein at each cycle of assembly the oligomer possesses a reactive alkyl amino terminus which is condensed with the next synthon to be added to the growing polymer. Because standard peptide chemistry is utilized, natural and non-natural amino acids are routinely incorporated into a PNA oligomer. Because a PNA is a polyamide, it has a C-terminus (carboxyl terminus) and an N-terminus (amino terminus). For the purposes of the design of a hybridization probe suitable for antiparallel binding to the target sequence (the preferred orientation), the N-terminus of the probing nucleobase sequence of the PNA probe is the equivalent of the 5'-hydroxyl terminus of an equivalent DNA or RNA oligonucleotide.

PNA Labeling:

The Detection Complexes of this invention comprise at least one donor moiety and at least one acceptor moiety. Preferably, a donor moiety is a fluorophore and an acceptor moiety is a quencher moiety. The donor and acceptor moieties are preferably, but not necessarily, attached to the termini of the component polymers of the Detection Complexes.

Labeling of a PNA is analogous to peptide labeling. Because the synthetic chemistry of assembly is essentially the same, any method commonly used to label a peptide can usually be adapted for use in labeling a PNA. Thus, PNAs may be labeled with numerous detectable moieties. Generally, any detectable moiety which can be linked to a nucleic acid or peptide can be linked to a PNA.

Typically, the N-terminus of the PNA is labeled by reaction with a moiety having a carboxylic acid group or activated carboxylic acid group. One or more spacer moieties can be introduced between the labeled moiety and the PNA oligomer. Generally, the spacer moiety is incorporated prior to performing the labeling reaction. However, the spacer may be embedded within the label and thereby be incorporated during the labeling reaction. Specialized reagents can be attached to the PNA. For example, a terminal arylamine moiety can be generated by condensing a suitably protected 4-aminobenzoic acid derivative with the amino terminus of the PNA oligomer.

In one embodiment, the C-terminal end of the PNA is labeled by first condensing a labeled moiety with the support upon which the labeled PNA is to be assembled. Next, the first synthon of the PNA is condensed with the labeled moiety. Alternatively, one or more spacer moieties can be introduced between the labeled moiety and the PNA oligomer (e.g. 8-amino-3,6dioxaoctanoic acid). After the PNA is completely assembled and labeled, the PNA is cleaved from the support, deprotected and purified using standard methodologies.

For example, the labeled moiety could be a lysine derivative wherein the ε-amino group is labeled with a detectable moiety such as 5(6)-carboxyfluorescein. Alternatively, the labeled moiety could be a lysine derivative wherein, the ε-amino group is derivatized with 4-((-4-(dimethylamino)phenyl)azo)benzoic acid (dabcyl). Condensation of the lysine derivative with the support would be accomplished using standard condensation (peptide) chemistry. The α-amino group of the lysine derivative could then be deprotected and the PNA assembly initiated by condensation of the first PNA synthon with the α-amino group of the lysine amino acid. After complete assembly, the PNA oligomer would then be cleaved from the support, deprotected and purified using well known methodologies.

Alternatively, a functional group on the assembled, or partially assembled, polymer is labeled while it is still support bound. This method requires that an appropriate protecting group be incorporated into the oligomer to thereby yield a reactive functional to which the detectable moiety is linked, but has the advantage that the label (e.g. a fluorophore or quencher moiety) can be attached to any position within the polymer including within the probing segment. For example, the ε-amino group of a lysine could be protected with a 4-methyl-triphenylmethyl (Mtt), a 4-methoxy-triphenylmethyl (MMT) or a 4,4'-dimethoxytriphenylmethyl (DMT) protecting group. The Mtt, MMT or DMT groups can be removed from PNA (assembled using commercially available Fmoc PNA monomers and polystyrene support having a PAL linker; PerSeptive Biosystems, Inc., Framingham, Mass.) by treatment of the resin under mildly acidic conditions. Consequently, the labeling reagent can then be condensed with the ε-amino group of the lysine amino acid. After complete assembly and appropriate labeling, the polymer is then cleaved from the support, deprotected and purified using well known methodologies.

Alternatively, a label is attached to the PNA after it is fully assembled, cleaved from the support and optionally purified. This method is preferable where the label is incompatible with the cleavage, deprotection or purification regimes commonly used to manufacture PNA. By this method, the PNA will generally be labeled in solution by the reaction of a functional group on the PNA and a functional group on the label. Those of ordinary skill in the art will recognize that the composition of the coupling solution will depend on the nature of PNA and the labeling reagent. The solution may comprise organic solvent, water or any combination thereof. Generally, the organic solvent will be a polar non-nucleophilic solvent. Non-limiting examples of suitable organic solvents include acetonitrile, tetrahydrofuran, dioxane and N,N'-dimethylformamide.

Generally, the functional group on the PNA will be an amine and the functional group on the labeling reagent will be a carboxylic acid or activated carboxylic acid. Non-limiting examples of activated carboxylic acid functional groups include N-hydroxysuccinimidyl esters. If the label is an enzyme, preferably the amine on the PNA will be an arylamine. In aqueous solutions, the carboxylic acid group of either of the PNA or label (depending on the nature of the components chosen) can be activated with a water soluble carbodiimide. The reagent, 1-(3-dimethylaminopropyl)-3-ethylcarbodiimide hydrochloride (EDC), is a commercially available reagent sold specifically for aqueous amide forming condensation reactions.

Generally, the pH of aqueous solutions will be modulated with a buffer during the condensation reaction. Preferably, the pH during the condensation is in the range of 4–10. When an arylamine is condensed with the carboxylic acid, preferably the pH is in the range of 4–7. When an alkylamine is condensed with a carboxylic acid, preferably the pH is in the range of 7–10. Generally, the basicity of non-aqueous reactions will be modulated by the addition of non-nucleophilic organic bases. Non-limiting examples of suitable bases include N-methylmorpholine, triethylamine and N,N-diisopropylethylamine. Alternatively, the pH is modulated using biological buffers such as (N-[2-hydroxyethyl] piperazine-N'-[2-ethanesulfonic acid) (HEPES) or 4-morpholineethane-sulfonic acid (MES) or inorganic buffers such as sodium bicarbonate.

Nucleic Acid Synthesis and Labeling

Nucleic acid oligomer (oligonucleotide and oligoribonucleotide) synthesis has become routine. For a detailed description of nucleic acid synthesis please see Gait, M. J., *Oligonucleotide Synthesis: a Practical Approach*. IRL Press, Oxford England. Preferably, nucleic acid oligomers are synthesized on supports in what is known as solid phase synthesis. Alternatively, they are synthesized in solution. Those of ordinary skill in the art will recognize that both labeled, unlabeled and/or modified oligonucleotides (DNA, RNA and synthetic analogues thereof) are readily available. They can be synthesized using commercially available instrumentation and reagents or they can be purchased from commercial vendors of custom manufactured oligonucleotides. Patents which discuss various compositions, supports and methodologies for the synthesis and labeling of nucleic acids include: U.S. Pat. Nos. 5,476,925, 5,453,496, 5,446,137, 5,419,966, 5,391,723, 5,391,667, 5,380,833, 5,348,868, 5,281,701, 5,278,302, 5,262,530, 5,243,038, 5,218,103, 5,204,456, 5,204,455, 5,198, 527, 5,175,209, 5,164,491, 5,112,962, 5,071,974, 5,047,524, 4,980,460, 4,923,901, 4,786,724, 4,725,677, 4,659,774, 4,500,707, 4,458,066, and 4,415,732 which are herein incorporated by reference.

Labels:

The labels attached to the Detection Complexes of this invention comprise a set (hereinafter "Beacon Set(s)") of energy or electron transfer moieties comprising at least one donor and at least one acceptor moiety. Typically, the Beacon Set will include a single donor moiety and a single acceptor moiety. Nevertheless, a Beacon Set may contain more than one donor moiety and/or more than one acceptor moiety. For example, a set could comprise three moieties. Moiety one may be a donor fluorophore which, when exited and located in close proximity to moiety two, can then transfer energy to moiety two of the Beacon Set. Thereafter, moiety two, which when excited and located in close proximity to moiety three, can transfer energy to moiety three of the Beacon Set. Consequently, energy is transferred between all three moieties of this Beacon Set. In this set, moiety two is both an acceptor of energy from moiety one and a donor of energy to moiety three. Such transfers of energy between two or more moieties of a Beacon Set are contemplated by the practice of this invention.

The donor and acceptor moieties operate such that one or more acceptor moieties accepts energy transferred from the one or more donor moieties or otherwise quench signal from the donor moiety or moieties. Transfer of energy may occur through collision of the closely associated moieties of a Beacon Set (non-FRET) or through a nonradiative process such as fluorescence resonance energy transfer (FRET). For FRET to occur, transfer of energy between donor and acceptor moieties requires that the moieties be close in space and that the emission spectrum of a donor have substantial overlap with the absorption spectrum of the acceptor (See: Yaron et al. Analytical Biochemistry, 95, 228–235 (1979) and particularly page 232, col. 1 through page 234, col. 1). Alternatively, non-FRET energy transfer may occur between very closely associated donor and acceptor moieties whether or not the emission spectrum of a donor moiety has a substantial overlap with the absorption spectrum of the acceptor (See: Yaron et al. Analytical Biochemistry, 95, 228–235 (1979) and particularly page 229, col. 1 through page 232, col. 1). This process is referred to as intramolecular collision since it is believed that quenching is caused by the direct contact of the donor and acceptor moieties (See: Yaron et al.).

Preferred donor and acceptor moieties are fluorophore and quencher combinations, respectively. Numerous amine reactive labeling reagents are commercially available (as for example from Molecular Probes, Eugene, Oreg.). Preferred labeling reagents will be supplied as carboxylic acids or as the N-hydroxysuccinidyl esters of carboxylic acids. Preferred fluorochromes (fluorophores) include 5(6)-carboxyfluorescein (Flu), 6-((7-amino-4-methylcoumarin-3-acetyl)amino)hexanoic acid (Cou), 5(and 6)-carboxy-X-rhodamine (Rox), Cyanine 2 (Cy2) Dye, Cyanine 3 (Cy3) Dye, Cyanine 3.5 (Cy3.5) Dye, Cyanine 5 (Cy5) Dye, Cyanine 5.5 (Cy5.5) Dye Cyanine 7 (Cy7) Dye, Cyanine 9 (Cy9) Dye (Cyanine 2, 3, 3.5, 5 and 5.5 are available as NHS esters from Amersham, Arlington Heights, Ill.) or the Alexa dye series (Molecular Probes, Eugene, Oreg.). The most preferred fluorophores are the derivatives of fluorescein and particularly 5 and 6-carboxyfluorescein. The acceptor moiety may be a second fluorophore but preferably the acceptor moiety is a quencher moiety. A quencher moiety is a moiety which can quench detectable signal from a donor moiety such as a fluorophore. Most preferably, the quencher moiety is an aromatic or heteroaromatic moiety which is substituted with one or mores azo or nitro groups. The most preferred quencher moiety is 4-((-4-(dimethylamino)phenyl)azo) benzoic acid (dabcyl).

Detection of Energy Transfer:

When the Detection Complex is formed, at least one donor moiety of one component polymer is brought sufficiently close in space to at least one acceptor moiety of a second component polymer. Since the donor and acceptor moieties of the set are closely situated in space, transfer of energy occurs between moieties of the Beacon Set. When the Detection Complex dissociates, the donor and acceptor moieties do not interact sufficiently to cause substantial transfer of energy from the donor and acceptor moieties of the Beacon Set and there is a correlating change in detectable signal from the donor and/or acceptor moieties of the set. Consequently, Detection Complex formation/dissociation can be determined by measuring at least one physical property of at least one member of the Beacon Set which is detectably different when the complex is formed as compared with when the component polymers of the Detection Complex exist independently and unassociated.

Alternatively, a detectable change in signal attributable exclusively to hybridization which does not result in complex dissociation, may also be correlated with the presence, absence or quantity of the target sequence and target molecule in the sample provided there is a detectable change in at least one physical property of at least one member of a Beacon Set which is detectably different in the native Detection Complex as compared with when the still intact Detection Complex is further complexed to a target sequence of the target molecule. We refer to the changes in detectable signal attributable to hybridization or complex dissociation as the self-indicating property of Detection Complexes and PCR Detection Complexes (as defined herein) of this invention.

Preferably the Detection Complexes dissociate since mean distance between the linked donor and acceptor moieties of the unassociated polymers will be very large as compared with the still complexed polymers. Because of the large distance, there will be essentially no transfer or energy between the donor and acceptor moieties of the dissociated polymers whereas there will likely still be a substantial transfer of energy between moieties of the still complexes polymers. Consequently, there should be a substantially greater change in detectable signal when the Detection Complex dissociates as compared with when mere hybridization results in a detectable change. Similarly, the Detection Complexes of this invention should generate a greater change in detectable signal as compared with unimolecular probes since the linked donor and acceptor moieties of the unimolecular probes cannot be infinitely separated in space.

In addition to energy transfer labels, the donor and acceptor moieties of this invention may be electron transfer moieties wherein a detectable signal arises from the transfer or electron between the moieties when they are close in space but is less efficient when they are more separated in space.

Detectable and Independently Detectable Moieties/Multiplex Analysis:

In preferred embodiments of this invention, a multiplex hybridization assay is performed. In a multiplex assay, numerous conditions of interest are simultaneously examined. Multiplex analysis relies on the ability to sort sample components or the data associated therewith, during or after the assay is completed. In preferred embodiments of the invention, distinct independently detectable moieties are used to label component polymers of two or more different Detection Complexes. The ability to differentiate between and/or quantitate each of the independently detectable moieties provides the means to multiplex a hybridization assay because the data which correlates with the hybridization of each of the distinctly (independently) labeled Detection Complexes to a target sequence can be correlated with the presence, absence or quantity of each target sequence or target molecule sought to be detected in a sample. Consequently, the multiplex assays of this invention may be used to simultaneously detect the presence, absence or quantity of two or more target sequence or target molecule in the same sample and in the same assay. Because the Detection Complexes are self-indicating, and can be designed to be independently detectable, the multiplex assays of this invention can be performed in a closed tube format to provide data for simultaneous real-time and end-point analysis of a sample for two or more target sequences or target molecules of interest in the same assay. Additionally, the assays can be further multiplexed by the incorporation of unimolecular "Beacon" probes to thereby confirm assay performance or be used to identify a specific feature of a target sequence or target molecule of interest.

Spacer/Linker Moieties:

Generally, spacers are used to minimize the adverse effects that bulky labeling reagents might have on hybridization properties of non-nucleic acid probes. Linkers typically induce flexibility and randomness into the probe or otherwise link two or more nucleobase sequences of a probe or component polymer. Preferred spacer/linker moieties for non-nucleic acid component polymers of the Detection Complexes of this invention consist of one or more aminoalkyl carboxylic acids (e.g. aminocaproic acid) the side chain of an amino acid (e.g. the side chain of lysine or ornithine) natural amino acids (e.g. glycine), aminooxyalkylacids (e.g. 8-amino-3,6-dioxaoctanoic acid), alkyl diacids (e.g. succinic acid), alkyloxy diacids (e.g. diglycolic acid) or alkyldiamines (e.g. 1,8-diamino-3,6-dioxaoctane). Spacer/linker moieties may also incidentally or intentionally be constructed to improve the water solubility of the probe (For example see: Gildea et al., *Tett. Lett.* 39: 7255–7258 (1998)). Preferably, a spacer/linker moiety comprises one or more linked compounds having the formula: —Y—(O$_m$—(CW$_2$)$_n$)$_o$—Z—. The group Y has the formula: a single bond, —(CW$_2$)$_p$—, —C(O)(CW$_2$)$_p$—, —C(S)(CW$_2$)$_p$— and —S(O$_2$)(CW$_2$)$_p$. The group Z has the formula NH, NR$^2$, S or O. Each W is independently H, R$^2$, —OR$^2$, F, Cl, Br or I; wherein, each R$^2$ is independently selected from the group consisting of: —CX$_3$, —CX$_2$CX$_3$, —CX$_2$CX$_2$CX$_3$, —CX$_2$CX(CX$_3$)$_2$, and —C(CX$_3$)$_3$. Each X is independently H, F, Cl, Br or I. Each m is independently 0 or 1. Each n, o and p are independently integers from 0 to 10.

Hybridization Conditions/Stringency:

Those of ordinary skill in the art of nucleic acid hybridization will recognize that factors commonly used to impose or control stringency of hybridization include formamide concentration (or other chemical denaturant reagent), salt concentration (i.e., ionic strength), hybridization temperature, detergent concentration, pH and the presence or absence of chaotropes. Optimal stringency for a probe/target combination is often found by the well known technique of fixing several of the aforementioned stringency factors and then determining the effect of varying a single stringency factor. The same stringency factors can be modulated to thereby control the stringency of hybridization of the probing segment of a Detection Complex to a target sequence, except that the hybridization of a non-nucleic acid polymer (e.g. PNA) is fairly independent of ionic strength. Optimal stringency for an assay may be experimentally determined by examination of each stringency factor until the desired degree of discrimination is achieved.

The aforementioned stringency factors shall also be applicable to stabilize or dissociate the Detection Complexes of this invention since they comprise two or more component polymers which anneal. Consequently, control of stringency factors may allow one to preferentially modulate the stability of the Detection Complex and/or target molecule in a controlled fashion to thereby achieve additional advantages and benefits. For example, an otherwise highly structured nucleic acid can be substantially dissociated in low salt conditions wherein the Detection Complex can be designed to retain stability since at least one component polymer is a non-nucleic acid polymer such as a PNA. Under these conditions, a PNA probing segment of a Detection Complex will more easily interact with the target sequence which might ordinarily be buried in a highly structured region and ordinarily be inaccessible to a nucleic acid probe.

Suitable Hybridization Conditions:

Generally, the more closely related the background causing nucleic acid contaminates are to the target sequence, the more carefully stringency must be controlled. Blocking probes may also be used as a means to improve discrimination beyond the limits possible by mere optimization of stringency factors. Suitable hybridization conditions will thus comprise conditions under which the desired degree of discrimination is achieved such that an assay generates an accurate (within the tolerance desired for the assay) and reproducible result. Aided by no more than routine experimentation and the disclosure provided herein, those of skill in the art will easily be able to determine suitable hybridization conditions for performing assays utilizing the methods, kits and compositions described herein.

Blocking Probes:

Blocking probes are PNA, nucleic acid or non-nucleic acid probes which can be used to suppress the binding of the probing segment of the probing polymer to a non-target sequence. Preferred blocking probes are PNA probes (See: Coull et al., WIPO publication No. WO98/24933). Typically blocking probes are closely related to the probing segment and preferably they comprise a point mutation of the probing segment. It is believed that blocking probes operate by hybridization to the non-target sequence to thereby form a more thermodynamically stable complex than is formed by hybridization between the probing segment and the non-target sequence. Formation of the more stable and preferred complex blocks formation of the less stable non-preferred complex between the probing segment and the non-target sequence. Thus, blocking probes can be used with the methods, kits and compositions of this invention to suppress the binding of the probing segment of the probing polymer of a Detection Complex to non-target sequences.

II. Compositions of the Invention

A. Probe And Primer Detection Complexes (Detection Complexes):

In one embodiment, this invention is directed to Detection Complexes. Detection Complexes are hybrids of at least two component polymers. At least two of the component polymers of the Detection Complex comprise at least one moiety from a set of donor and acceptor moieties (a Beacon Set), though the Detection Complex may comprise more than one Beacon Set. Component polymers are designed to form the Detection Complex by the interaction of interacting groups. The Detection Complex may comprise one or more linkers and/or one or more spacer moieties as may be useful to construct a Detection Complex suitable for a particular application.

Each Detection Complex comprises at least one probing polymer and at least one annealing polymer. The probing polymer contains a sequence of subunits suitable for detecting a target molecule as a result of the hybridization of the probing segment to the target sequence or priming site. Typically, the annealing polymers primary utility will be to form the Detection Complex, though the annealing polymer may, in certain embodiments, also contain a nucleobase sequence suitable for detecting a different target molecule of interest. Interacting groups cause probing polymer(s) to anneal to the annealing polymer(s) to thereby form and stabilize the Detection Complex. Any combination of probing and annealing polymers may be constructed with the appropriate interacting groups. Moreover, the probing and annealing polymers may be PNA, DNA, RNA, chimeric oligomers or linked polymers, provided at least one of the component polymers is a non-nucleic acid polymer. Preferably, the non-nucleic acid polymer is a peptide nucleic acid (PNA).

With reference to FIG. 1A, a simple example of a Detection Complex comprising a single donor and single acceptor moiety is illustrated. The Detection Complex comprises a single set of donor and acceptor moieties (1 and 2), each of which is linked to a different component polymer(i.e. a single Beacon Set). As illustrated, the interacting groups (20 interacting with 21) comprise nucleobase sequences of the probing polymer (30) and the annealing polymer (31). The Detection Complex is formed and stabilized by the interaction of the interacting groups. As illustrated, the annealing polymer (31) comprises only the interacting groups (21) necessary to form a stable complex with the probing polymer (30) and therefore the annealing polymer (31) is shorter than the probing polymer (30). Because the probing polymer (30) must form a stable hybrid with the target sequence or priming site, often the probing polymer (30) will be designed to be longer than the annealing polymer (31).

With reference to FIG. 1B, a more elaborate example of a Detection Complex is illustrated. As illustrated, the Detection Complex comprises two sets of donor and acceptor moieties (i.e. two Beacon Sets). One Beacon Set comprises moieties 3 and 5 whereas the second Beacon Set comprises moieties 4 and 6. As illustrated, each polymer comprises two sets of interacting groups (22 interacting with 23; 24 interacting with 25) wherein one interacting group is located at each terminus of each of the probing polymer (32) and annealing polymer (33). Interacting groups form and stabilize the Detection Complex. As illustrated, the segments in the center of the probing polymer (32) and annealing polymer (33) do not interact and therefore the non-interacting segments of each component polymer are shown to bulge out (26).

With reference to FIG. 1C, a still more elaborate example of a Detection Complex is illustrated. As illustrated, the Detection Complex comprises three sets of donor and acceptor moieties (i.e. three Beacon Sets). One Beacon Set comprises moieties 7 and 10, a second Beacon Set comprises moieties 8 and 11 and the third Beacon Set comprises moieties 9 and 12. This Detection Complex comprises three polymers, only one of which is designated as the probing polymer (34). In this illustration, the other two polymers are annealing polymers (35 and 36). As illustrated, each polymer comprises two sets of interacting groups (40 interacting with 41, 42 interacting with 43; 44 interacting with 45) wherein one interacting group is located at each terminus of the probing polymer (34) and each of the annealing polymers (35 and 36). The Detection Complex is formed and stabilized by the interaction of the interacting groups. As illustrated the segments in the center of the probing polymer (34) and annealing polymers (35 and 36) do not interact and therefore the non-interacting segments of each component polymer are shown to bulge out (26).

The Detection Complexes of this invention are primarily designed to dissociate as a direct or indirect consequence of the hybridization of one or more segments of a component polymer to a target sequence or priming site. Consequently, the Detection Complexes can be used to detect the presence, absence or quantity of a target molecule of interest, which may be present in a sample of interest. The presence, absence or quantity of target molecule of interest in a sample can then be determined by directly or indirectly correlating the dissociation of Detection Complex with the hybridization of a component polymer to a target sequence. Because the component polymers of a Detection Complex will preferably dissociate, the attached donor and acceptor moieties, which are independently attached to different polymers, can become far more separated in space as compared with unimolecular "Beacon" probes such as Molecular Beacons (PNA or nucleic acid) or Linear Beacons (Examples of unimolecular "Beacon" probes include hairpin forming nucleic acid Molecular Beacons (See: Tyagi et al., Tyagi2 et al. and Tyagi3 et al.), PNA Molecular Beacons (See: U.S. Ser. No. 08/958,532 (allowed) and copending U.S. Ser. No. 09/179,298, both incorporated herein by reference) and Linear Beacons (See: copending U.S. Ser. No. 09/179,162, herein incorporated by reference). As a consequence, the efficiency of energy transfer, which is proportional to the distance between the donor and acceptor moieties, will be far more substantially altered as compared with unimolecular "Beacon" probes wherein the donor and acceptor moieties are linked to the same polymer and therefore cannot be infinitely separated in space. Thus, the Detection Complexes of this invention possess a substantial comparative advantage over unimolecular constructs.

Though primarily designed to dissociate, the distance between donor and acceptor moieties may change merely because the probing segment of a probing polymer of a Detection Complex hybridizes to a target sequence whether or not the Detection Complex dissociates. Provided there is a detectable change in at least one physical property of at least one member of a set which is detectably different in the native Detection Complex as compared with when the still intact Detection Complex is further complexed to a target sequence of a target molecule, the Detection Complexes of this invention may also be used to determine the presence absence or quantity of a target sequence or target molecule in a sample even though the Detection Complex does not dissociate.

By way of example, a typical assay performed in accord with this invention might involve determining the increase in fluorescence during the assay, wherein an increase in fluorescence correlates with hybridization of the probing segment to the target sequence whether or not the Detection Complex dissociates. Consequently, the change in fluorescence intensity can then be correlated with the presence, absence or quantity of target sequence present in the sample. Furthermore the presence, absence or quantity of target sequence can then be correlated with the presence, absence or quantity of the target molecule of interest. Typically quantitation of target sequence or target molecule will be made by comparison with a standard curve generated using a standardized procedure and known quantities of target sequence or target molecule in a representative sample.

Probing Polymers:

Probing polymers comprise at least one probing segment. The probing segment of the Detection Complex is the sequence specific recognition portion of the construct. Therefore, the probing segment is a nucleobase sequence containing subunits designed to hybridize to a specific target sequence or priming site under suitable hybridization conditions. Unlike nucleic acid Molecular Beacons, there is no requirement that a portion of the Detection Complex be specifically designed for self-hybridization. Thus, the entire probing polymer may comprise the probing segment wherein the interacting groups are integral to the probing segment. Alternatively, the probing polymer may contain both a probing segment and also one or more interacting groups, wherein the interacting groups do not hybridize to or otherwise interact with the target sequence or priming site.

Probing Segment:

With due consideration of the requirements of a probing polymer, the length of the probing segment will generally be chosen such that a stable complex is formed between the probing segment and the target sequence or priming site. The probing segment, suitable for the practice of this invention, will generally have a length of between 5 and 50 subunits. Preferably, the probing segment will be 7 to 25 subunits in length. Most preferably, the probing segment will be 12 to 20 subunits in length.

The probing segment of a Detection Complex will generally have a nucleobase sequence which is complementary to the target sequence. Alternatively, a substantially complementary probing segment might be used since it has been demonstrated that greater sequence discrimination can be obtained when utilizing probes wherein there exists a single point mutation (base mismatch) between the probe and the target sequence (See: Guo et al., *Nature Biotechnology* 15: 331–335 (1997)).

Annealing Polymers:

One or more annealing polymers anneal to a probing polymer to thereby form a Detection Complex. Thus, an annealing polymer may, in some embodiments, merely be used to form the Detection Complex. Alternatively, the annealing polymer may itself be an information containing polymer such as a second probing polymer. Consequently, the Detection Complex can be constructed of more than one probing polymer, wherein each probing polymer is also the annealing polymer for the other probing polymer. At a minimum, an annealing polymer comprises interacting groups necessary for the formation of the Detection Complex when annealed to the probing polymer though at least one annealing polymer of a Detection Complex must have at least one linked member of a Beacon Set.

Interacting Groups:

Interacting groups are the moieties of component polymer(s) which form and stabilize the Detection Complex. The interacting groups may comprise the entirety of the probing and/or annealing polymer(s). Alternatively, the interacting groups may comprise only a subset of the subunits of each of the probing and/or annealing polymer(s).

Interacting groups may be hydrophobic moieties such as the fluorophores and quenchers or otherwise comprise both fluorophore(s) and quencher(s) in concert with other lipophilic moieties. In other embodiments, the interacting groups may be ionized groups which form salt pairs. One example of such a salt pair would comprise the interaction of positively charged $\epsilon$-amino group(s) of one or more lysine moieties paired with negatively charged side chain carboxylic acid group(s) of one or more aspartic acid or glutamic acid moieties (charges are based on physiological pH). In another embodiment, the interacting groups comprise hydrogen bonding moieties. In the most preferred embodiment, interacting groups are complementary nucleobases of all or portions of the nucleobase sequence of the component polymers. Formation and stability of the Detection Complex will inevitably be affected by all of the hydrophobic, ionic and hydrogen bonding properties of the all moieties of the component polymers.

Interacting groups may be located at only one terminus of each of the probing and annealing polymers (e.g. FIG. 1A). Alternatively, interacting groups are linked to both termini of each of the component polymers (e.g. FIGS. 1B & 1C). In still other embodiments, interacting groups may be internal (e.g. centered within one or more component polymers) to one or more of the component polymers.

In preferred embodiments, the Detection Complex is formed from a single probing polymer and a single annealing polymer. More preferably, all of the subunits of the annealing polymer interact with only a portion of the subunits of the probing polymer (e.g. FIG. 1A). In a most preferred embodiment, formation and stability of the Detection Complex is primarily determined by the interaction of complementary nucleobases of the subunits of the component polymers.

With reference to FIGS. 1B and 1C, the two or more bulges (26) of the Detection Complexes may result because segments of the component oligomers are linked by a linker. Since the linkers do not typically contain interacting groups, these sections of the component polymers do not interact by design. For example, one of the Detection Complexes discussed in Examples 13 & 14 of this specification is formed from a PNA component polymer having two linked oligomer segments. Alternatively, the bulges may result simply because the nucleobases of the component polymers are non-complementary and therefore do not interact.

Base Pairing Motifs:

When the interacting groups comprise nucleobases, any base pairing motif which is will form a stable complex of at least two component polymers of a Detection Complex can be used to form the Detection Complex. Non-limiting examples of suitable base pairing motifs include duplexes, triplexes as well as other multimers and higher order structures which nucleic acids, nucleic acid analogs, nucleic acid mimics, chimeras and/or linked polymers can adopt to form a complex.

Equilibrium Factors:

Detection Complexes, PCR Detection Complexes and Substrate Detection Complexes are hybrids formed in solution by mixing the component polymers under conditions favorable for complex formation. Because the quantity of each component polymer added to form the Detection Complex, PCR Detection Complex or Substrate Detection Complex can be calculated and controlled, the extent of complex formation/dissociation can be manipulated or controlled by adjusting the quantity and concentration of the two or more component polymers present in the assay to thereby reduce background in a manner not possible with unimolecular probes to which both members of the Beacon Set are linked.

For example, if a probing polymer, containing a single fluorophore, and an annealing polymer, containing a single quenching moiety, are 95% associated when in a ratio of 1:1 (at a given concentration), but, are 99.9% associated when mixed in a ratio of 1:5 (at the same given concentration), the sample containing the 1:1 ratio will have a substantial background fluorescence attributable to the 5% fluorescently labeled probing polymer which is free in solution. However, the sample containing a 1:5 ratio will have substantially less inherent fluorescence because essentially all of the fluorophore containing polymer is completely complexed to the quencher moiety containing annealing polymer. Consequently, the background fluorescence of any solution containing Detection Complexes, PCR Detection Complexes or Substrate Detection Complexes can be adjusted by altering the relative ratios and concentrations of component polymers to thereby adjust the extent of hybrid formation.

It follows that the background fluorescence of the assays utilizing the Detection Complex or PCR Detection Complex of this invention may also be favorably modulated by the binding one of the component polymers to a target sequence. Extending the example analysis above, we will assume that a solution used to analyze a sample for target sequence comprises a 1:1 ratio of probing and annealing polymers to thereby produce a solution containing 95% of the Detection Complex. If we assume that 80% of the probing polymer becomes annealed preferentially to the target sequence of the sample thereby resulting in dissociation of the Detection Complex or PCR Detection Complex, the relative ratio of probing and annealing polymers which are still free in solution to form the Detection Complex or PCR Detection Complex is then 1:5 (all fluorophore containing probe is now 99.9% associated to a quencher containing probe). This shift in equilibrium will result in a significant reduction in the background fluorescence of the system. It thereby follows that the judicious choice of compositions and methods for the formation of the Detection Complexes or PCR Detection Complexes will enhance the practice of this invention. Furthermore, because non-nucleic acid polymers such as native PNA bind more strongly to nucleic acid than does nucleic acid, use of one or more PNA polymers as the component polymers of the Detection Complex is particularly advantageous since less excess of a polymer is needed to drive the equilibrium toward essentially complete formation of the Detection Complex.

Formation and Stability of Detection Complexes, PCR Detection Complexes and Substrate Detection Complexes Component polymers may be constructed so that multiple types of interacting groups are present and contribute to the stability/lability of the assembled Detection Complex, PCR Detection Complex or Substrate Detection Complex (See discussion in section entitled "Interacting Groups"). Typically, the composition of the component polymers is judiciously chosen so that the Detection Complex, PCR Detection Complex or Substrate Detection Complex is stable under predefined conditions and dissociates under predefined conditions. Generally, the thermodynamic parameters for the stability and lability of a Detection Complex, PCR Detection Complex or Substrate Detection Complex can be determined by examination of melting point since those of skill in the art will recognizes that Tm analysis can be used to determine the $\Delta H$, $\Delta S$ and $\Delta G$ values for formation and dissociation of a hybrid of two or more polymers. The practice is so common, the software which accompanies automated instrumentation is typically equipped to derive the $\Delta H$, $\Delta S$ and $\Delta G$ values after the Tm is performed. Choosing a Detection Complex, PCR Detection Complex or Substrate Detection Complex of proper stability is essential for designing assays for real-time and end-point analysis of a sample. It is important to note however, that real-time analysis must be made under conditions where the Detection Complex, PCR Detection Complex or Substrate Detection Complex is free to form so that detectable signal changes are properly attributable to the presence of target sequence or target molecule and not to conditions which induce target independent dissociation (e.g. near or above the Tm of the complex). Using the disclosure provided herein, those of skill in the art will require no more than routine experimentation to design polymers for forming Detection Complexes, PCR Detection Complex or Substrate Detection Complex of suitable stability/lability for particular applications.

Though the composition of the interacting groups is the primary factor used to influence the stability/lability of the complex, the length and composition of the probing polymer may influence complex stability. Specifically, since hybridization is a cooperative event, the hybridization of the probing segment to a target sequence or primer site may sterically or functionally influence the interactions of interacting groups linked thereto. Consequently, these types of secondary effects will also be considered when choosing the composition of the component polymers of the Detection Complex, PCR Detection Complex or Substrate Detection Complex.

Preferably, the Detection Complex or PCR Detection Complex is designed to exist as a stable construct until such time as the interaction of the probing segment with a target sequence or primer site directly or indirectly results in complex dissociation. Consequently, the Detection Complex may be designed such that formation of a hybrid between the probing segment and the target sequence or primer site will directly cause dissociation of the complex. Alternatively, the Detection Complex or PCR Detection Complex may be designed such that the formation of a stable hybrid between the target sequence or priming site and the probing sequence does not directly dissociate the Detection Complex but does occur by operation of a secondary "triggering" event.

When the Detection Complex is intended to dissociate directly upon the hybridization of the probing segment to the target sequence, generally the complex is design such that the hybrid between the probing segment and target sequence or priming site is more thermodynamically stable than is the nature of the interactions which stabilize the Detection Complex. In this embodiment, the Detection Complex is generally constructed such that at least a portion of the subunits which comprise interacting groups of the probing polymer will also contribute to the formation of the hybrid between the probing segment and target sequence. The requirement that the same groups comprise one hybrid or the other when combined with the favorable thermodynamic considerations will result in direct dissociation of the Detection Complex. This embodiment is referred to as direct dissociation and is most preferred when the Detection Complex is used as a probe as compared to when it is used as a primer.

When the Detection Complex or PCR Detection Complex is intended to remain intact after the probing segment hybridizes to the target sequence or priming site, there are typically no interacting groups of the probing polymer which also contribute to the formation of the hybrid between the probing segment and the primer site or target sequence. For this reason, the thermodynamic stability of the hybrid formed from the probing segment and target sequence or primer site is typically unrelated to the thermodynamic stability of the interacting groups which form the Detection Complex. Consequently, the Detection Complex is generally constructed so that a secondary "triggering" event disrupts the interactions of the interacting groups to thereby cause dissociation of the Detection Complex. It follows that the Detection Complex is thermodynamically stable under predefined assay conditions until the secondary "triggering" event occurs, whereby the nature of the secondary event causes dissociation of the complex in a manner which can be used to accurately correlate the activity of the secondary "triggering" event with the presence, absence or quantity of target sequence. This embodiment is referred to herein as indirect dissociation and is most preferred when the Detection Complex is used as a primer as compared to when it is used as a probe.

By way of example, a generic construct of a Detection Complex is illustrated in FIG. 2. The Detection Complex can dissociate or remain assembled upon hybridization of the probing segment to a target sequence or priming site depending on the composition of the probing polymer. With reference to FIG. 2A, either of moiety A or B is independently selected as either a donor or acceptor moiety provided that: 1. if A is a donor moiety, then B is an acceptor: and 2. if A is an acceptor, then B is a donor moiety. Tethers 13 and 14 are spacer moieties which link the donor and acceptor moieties to the respective component polymers. Interacting groups 15 and 16 interact to form and stabilize the Detection Complex. The junction 17 is merely used to distinguish between segment 18 and the interacting group(s) 15 of the probing polymer (37). As illustrated, the Detection Complex is contacted with a target sequence of a target molecule of interest (12) under suitable conditions such that segment 18 forms a hybrid with the target sequence or priming site.

In the illustration, dissociation of the Detection Complex depends on whether the probing segment comprises both segments 15 and 18 of the probing polymer (37) or whether the probing segment comprises only segment 18. By route I, the Detection Complex or PCR Detection Complex hybridizes to the target sequence or primer site (the hybridization event) but does not dissociate since the probing segment comprises only segment 18. Dissociation does not occur because the one or more subunits of segment 15 are not designed to interact with the target sequence or primer site and therefore, no stress is applied to the interacting groups to thereby cause complex dissociation. Nevertheless, this Detection Complex can be used to detect a secondary "triggering" event or can be used as a measure of hybridization of the probing segment to the target sequence if there is an accompanying change in detectable signal from at least one member of the Beacon Set resulting from the hybridization event. Example 15 of this specification demonstrates the feasibility and utility of correlating the hybridization event with the amount of nucleic acid produced by a PCR reaction (i.e. the secondary "triggering" event is PCR).

By route II, the Detection Complex is dissociated as a result of the hybridization event because the probing segment comprises both segments 15 and 18. By design, the complex formed between the probing segment and the target sequence or primer site is thermodynamically favored. Since the initial interactions by segment 18 with the target will result in cooperative binding of the entire complementary sequence of the probing polymer, the interactions will necessarily cause the release of the annealing polymer (38) and dissociation of the Detection Complex. Therefore, dissociation of Detection Complexes of this embodiment can be used as a more direct method for the detection of the presence, absence or quantity of target sequence or target molecule present in a sample of interest. Example 14 of this specification demonstrates that Detection Complexes can be used as probes.

The route I scheme has several advantages over nucleic acid Molecular Beacons and related unimolecular "Beacon" probes. The constructs described in WO95/13399 and WO97/06208 are specifically utilized for the direct and specific detection of hybridization to a target sequence (See: pages 9–10, bridging paragraph). Moreover, the constructs of WO95/13399 are not designed to be one of the primers in a PCR reaction (See: pages 41–42, bridging paragraph). Specifically, the requirement for a secondary "triggering" event to occur before a detectable signal is produced in the assay adds a second level of discrimination to the assay. This second level of discrimination should reduce the occurrence of signal caused by non-specific events such as non-specific binding of the probing polymer to non-target molecules and non-target sequences. As a result, the assays utilizing Detection Complexes or PCR Detection Complexes which are design to produce signal in response to a hybridization coupled with the occurrence of a secondary "triggering" event should produce more reliable, accurate and reproducible results. Moreover, use of one or more non-nucleic acid polymers as one or more of the component polymers of the Detection Complex or PCR Detection Complex are particularly advantageous since they: 1) are not subject to enzymatic degradation; 2) can protect nucleic acid polymers to which they are hybridized from enzymatic degradation; 3) can operate at low ionic strength; 4) do not require magnesium to form hybrids; 5) reform hybrids very rapidly and efficiently; and 6) exhibit higher sequence discrimination; and therefore overcome limitations and disadvantage of nucleic acid Molecular Beacons and related constructs comprised solely of nucleic acid.

Secondary "Triggering" Events:

Secondary "triggering" events include any operation which requires hybridization of the probing segment to the target sequence or primer site and which thereby indirectly causes the Detection Complex or PCR Detection Complex to dissociate. Non-limiting examples of secondary "triggering" events include nucleic acid synthesis and nucleic acid amplification reactions. In a preferred embodiment, the secondary "triggering" event is a polymerase extension reaction. In a preferred embodiment, the complex formed between the probing segment and the target sequence (priming site) is the substrate for a polymerase. In a most preferred embodiment, the polymerase extension reaction is performed in a PCR amplification reaction.

In one embodiment, the probing polymer/target sequence complex which is formed may be a substrate for an enzyme such as a polymerase, transcriptase or ligase (See for example the constructs illustrated in FIG. 2). Thus, the probing polymer or target sequence may also function as a primer so that upon hybridization in the presence of a suitable enzyme and under suitable conditions, the probing polymer/target sequence complex will undergo a catalytic transformation (e.g. a polymerization, transcription or ligation reaction; etc.). Consequently, for this application, the probing polymer will generally be a nucleic acid because polymerases, transcriptases and ligases are known to operate on double stranded nucleic acid complexes. However, modified PNAs or chimeric PNAs are also known to be substrates for certain enzymes provide they comprise a necessary functional group (e.g. a 3'-hydroxyl group; See: Lutz et. al., *J. Am. Chem. Soc.*, 119: 3171–3178 (1997)). Thus, the probing polymer may be a modified PNA or PNA chimeric molecule. In a preferred embodiment, the Detection Complex or PCR Detection Complex is constructed from one nucleic acid probing polymer and one non-nucleic acid annealing polymer. Most preferably, the non-nucleic acid annealing polymer is a PNA.

Multiple Sets of Donor and Acceptor Moieties

Multiple Beacon Sets can be easily incorporated into the Detection Complexes, PCR Detection Complexes or Substrate Detection Complexes of this invention because the individual component polymers may incorporate multiple labels wherein each of the different labels of an individual component polymer pertain to a member of a different Beacon Set. For example, each of one annealing polymer and one probing polymer may be labeled at both termini with either of a donor fluorophore or quencher acceptor moiety of a Beacon Set. Consequently, two Beacons Sets may be present in a single Detection Complex. Assuming that two of the same fluorophore and two of the same quencher moieties are present, at least three combinations exist for the Detection Complex. In one combination, both fluorophores are attached to the probing polymer and both quenchers are attached to the annealing polymer. In the second combination, both quenchers are attached to the probing polymer and both fluorophores are attached to the annealing polymer. In the third combination, one fluorophore and one quenching moiety is attached to the probing polymer and one fluorophore and one quenching moiety is attached to the annealing polymer provided that members of each Beacon Set interact in the assembled Detection Complex.

In other embodiments, the fluorophores are different. Preferably, the different fluorophores used in each Beacon Set are independently detectable. Consequently, multiple Beacon Sets containing two or more independently detectable donor and/or acceptors moieties offer even greater diversity to the useful applications of Detection Complexes or PCR Detection Complexes. In preferred embodiments, these Detection Complexes and PCR Detection Complexes are particularly well suited for use in multiplex assays wherein detectable signal from each of the independently detectable fluorophores can be correlated with the presence, absence or quantity of a different target sequence in the same assay.

Figure 3:
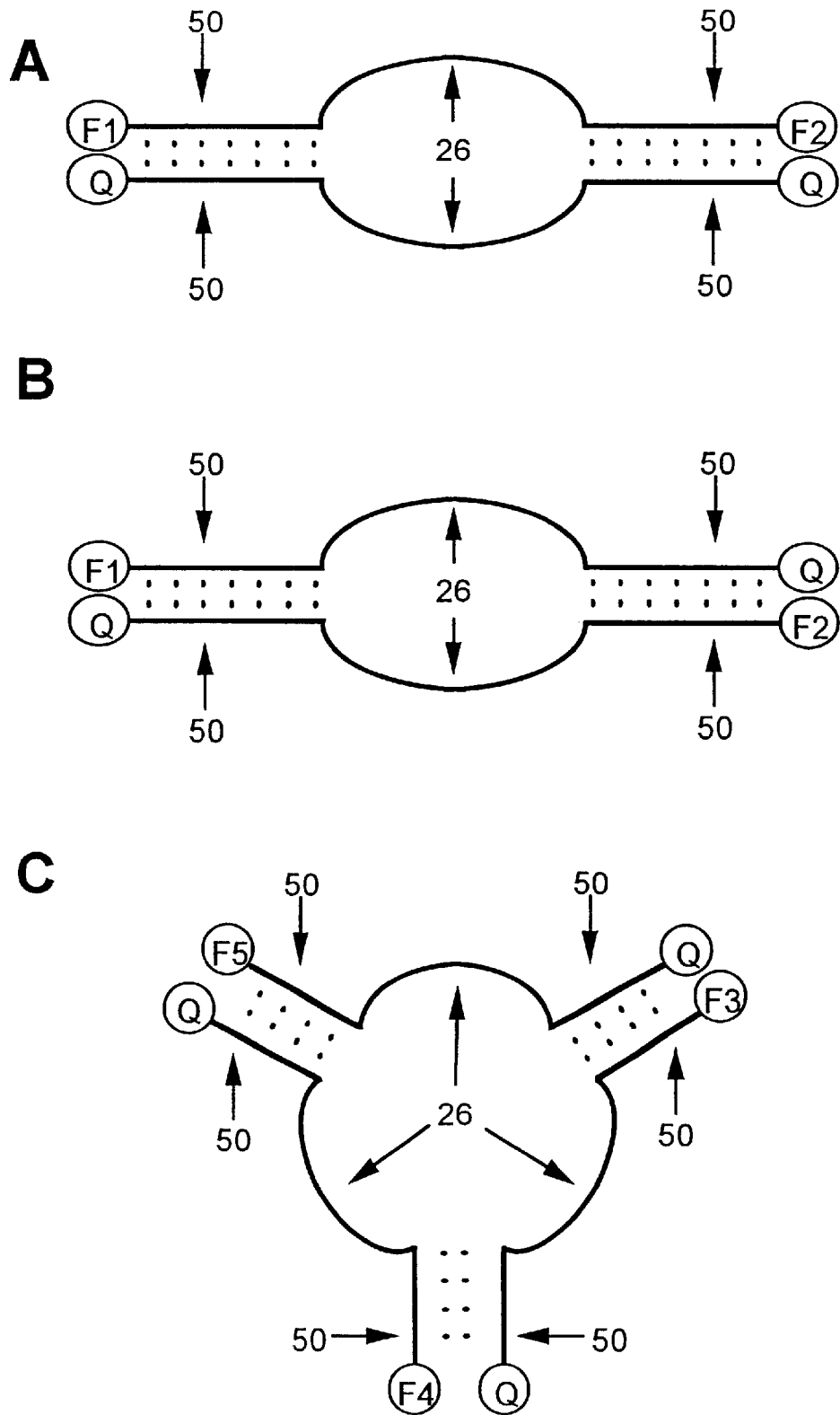
FIGS. 3A–3C illustrate several different embodiments of Detection Complexes comprising multiple sets of detectable moieties.
Figure 4:
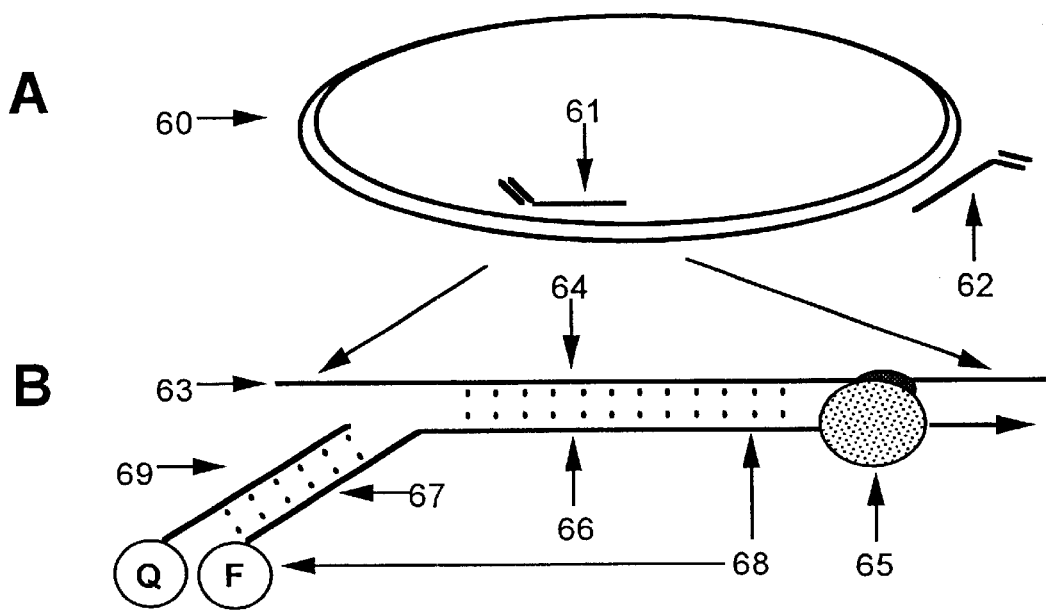
FIGS. 4A and 4B illustrate the initial operation of PCR using a Detection Complex as a PCR primer.

Several representative examples of Detection Complexes comprising multiple fluorophores are represented in FIGS. 3A–3C. With reference to FIGS. 3A–3C, the component polymers of each Detection Complex are represented with interacting groups present at both termini, wherein the middle segments of each of the polymers do not interact and consequently are represented as bulging out (26).

For this example, the Detection Complex is generally of the type described in FIG. 1B though other embodiments of Detection Complexes may be utilized. With reference to FIGS. 3A and 3B, each Detection Complex comprises two quencher moieties (Q), wherein each quencher may be the same or different. Also represented is a first donor fluorophore (F1) and a second donor fluorophore (F2). The interacting groups (50) of the component polymers form and stabilized the Detection Complex, thereby causing the donor fluorophores and quenchers to interact. For these examples, the probing and annealing polymers of the Complex need not be distinguished.

With reference to the embodiment illustrated in FIG. 3A, both the first donor fluorophore (F1) and the second donor fluorophore (F2) are linked at opposite ends of one component polymer. Consequently, the quencher moieties of each Beacon Set are linked to the termini of the other component polymer to thereby interact with the donor fluorophore of the appropriate donor/acceptor set in the assembled Detection Complex.

With reference to the embodiment illustrated in FIG. 3B, a first donor fluorophore (F1) and a second donor fluorophore (F2) are each linked to two different component polymers. A quencher moiety (Q) is also linked to each of the two component polymers in an orientation which provides quenching to each of F1 and F2. This construct is particularly useful in a multiplex assay provided that the two different component polymers each comprise a probing segment which is directed to a different target sequence of a target molecule of interest and the signal attributable to the probing segment/target sequence hybrid can be distinguished from the signal generated from the unhybridized but dissociated component polymer. Generally, this can be done by non-specifically concentrating nucleic acid on a matrix (e.g. a anion exchange matrix) and then assaying only the matrix for detectable signal from either or both of the independently detectable moieties of each Beacon Set. In preferred embodiments, the probing segments of the component polymers comprise that portion of the Detection Complexes which budge out (26).

In still another embodiment, three sets of donor and acceptor moieties may be utilized. With reference to the embodiment illustrated in FIG. 3C, the Detection Complex comprises three quencher moieties (Q), wherein each quencher may be the same or different. The Detection Complex also comprises a first donor fluorophore (F3), a second donor fluorophore (F4) and a third donor fluorophore (F5). As illustrated, the interacting groups (50) of the three polymers form and stabilized the Detection Complex, thereby causing the donor fluorophores and quenchers of a set to interact. For these examples, the donor and annealing polymers need not be distinguished but it follows from the discussion above that judicious choice and location of the component donor and acceptor moieties of each set will result in the production of the desired Detection Complex. The most preferred detection complexes will form and be useful for the detection of three different target sequences in the same assay using each of the three independently detectable moieties.

It follows that the principles discussed above can be used to prepare numerous alternative embodiments of Detection Complexes and PCR Detection Complexes which incorporate multiple component polymers and multiple sets of donor and acceptor moieties. Combination of independently detectable fluorophores are particularly useful in multiplex applications for the Detection Complexes of this invention. Numerous alternative embodiments of Detectable Complexes in combination with the multiple independently detectable moieties are contemplated as part of this invention.

B. Substrate Detection Complexes:

This invention also pertains to Detection Complexes which can operate as a substrate for an enzyme to thereby generate changes in detectable signal in a target independent manner. Non-limiting examples of suitable enzymes include transcriptases, ligases or polymerases. A Substrate Detection Complex is a complex of two or more component polymers. At least two of the component polymers of the Substrate Detection Complex comprise at least one moiety from a set of donor and acceptor moieties (a Beacon Set), though the Detection Complex may comprise more than one Beacon Set. Component polymers are designed to form the Detection Complex by the interaction of interacting groups. The Detection Complex may comprise one or more linkers and/or one or more spacer moieties as may be useful to construct a Substrate Detection Complex suitable for a particular application.

A Substrate Detection Complex is very similar to the Detection Complexes hereinbefore described except the Substrate Detection Complex differs from a Detection Complex or PCR Detection Complex in that it does not contain a probing segment which hybridizes to a target sequence or priming site of a target molecule of interest. Thus, the Substrate Detection Complex does not directly interact with the target sequence or target molecule of interest. However, a Substrate Detection Complex, at a minimum, comprises at least two annealing polymers wherein at least one of the annealing polymers can interact with itself, another annealing polymer or another molecule in the assay, which is not the target sequence, to thereby form a substrate for an enzyme. The two or more annealing polymers further comprise interacting groups which form and stabilize the Substrate Detection Complex. Any combination of annealing polymers may be constructed with the appropriate interacting groups. Moreover, the annealing polymers may be PNA, DNA, RNA, chimeric oligomers or linked polymers. Preferably, at least one of the component polymers is a non-nucleic acid polymer. Most preferably, the non-nucleic acid polymer is a peptide nucleic acid (PNA).

With reference to FIG. 20, an illustration of two non-limiting examples of Substrate Detection Complexes are presented. With reference to illustration 20A, the Substrate Detection Complex (90) is comprised of the two annealing polymers 80 and 81. Either of moiety A or B is independently selected as either a donor or acceptor moiety provided that: 1) if A is a donor moiety, then B is an acceptor: and 2) if A is an acceptor, then B is a donor moiety. Tethers 83 and 84 are spacer moieties which link the donor and acceptor moieties to the respective component polymers. Interacting groups 85 and 86 interact to form and stabilize the Substrate Detection Complex. As illustrated, the component annealing polymer 81 comprises a hairpin loop (88) and thereby forms a stem as a result of complementary base pairing between the nucleobases of segments 86 and 87. Furthermore, there is a free 3' or 5'-hydroxyl terminus (89) which is available to an enzyme such as a transcriptase, ligase or polymerase. Assuming that a polymerase (e.g. Taq polymerase) acts on the Substrate Detection Complex, under suitable condition, to extend from a 3'-hydroxyl group, the polymerase will read to the end of the annealing polymer 81 to thereby displace component polymer 80 and dissociate the Substrate Detection Complex.

With reference to illustration 20B, another exemplary Substrate Detection Complex (91) may be comprised of the three component annealing polymers 80 92 and 93. Either of moiety A or B is independently selected as either a donor or acceptor moiety provided that: 1) if A is a donor moiety, then B is an acceptor: and 2) if A is an acceptor, then B is a donor moiety. Tethers 83 and 84 are spacer moieties which link the donor and acceptor moieties to the respective component polymers. Interacting groups 85 and 86 interact to form and stabilize the Substrate Detection Complex. As illustrated, the component annealing polymer 92 hybridizes to both component polymers 80 and 93 though 80 and 93 do not directly interact. By comparison with Substrate Detection Complex 90, this embodiment does not comprise a hairpin loop since the stem results from complementary base pairing between segments 94 and 95 of the different component polymers 92 and 93, respectively. Substrate Detection Complex 91 comprises a free 3' or 5'-hydroxyl terminus (96) which is available to an enzyme such as a transcriptase, ligase or polymerase. Assuming that a polymerase (e.g. Taq polymerase) acts on the Substrate Detection Complex, under suitable conditions, to extend from a 3'-hydroxyl group, the polymerase will read to the end of the annealing polymer 92 to thereby displace component polymer 80 and dissociate the Substrate Detection Complex.

Because the Substrate Detection Complexes can be induced to dissociate, they are particularly useful in signal amplification methodologies. In preferred embodiments, the signal amplification methodologies are associated with a target dependent enzyme activity so that the signal generated by the Substrate Detection Complex can be used to detect or identify the presence, absence or quantity of a target sequence and/or target molecule of interest in an assay. In preferred embodiments, the target dependent enzyme activity will be associated with a probe-based hybridization assay suitable for the detection of a target sequence or target molecule of interest.

Figure 21:
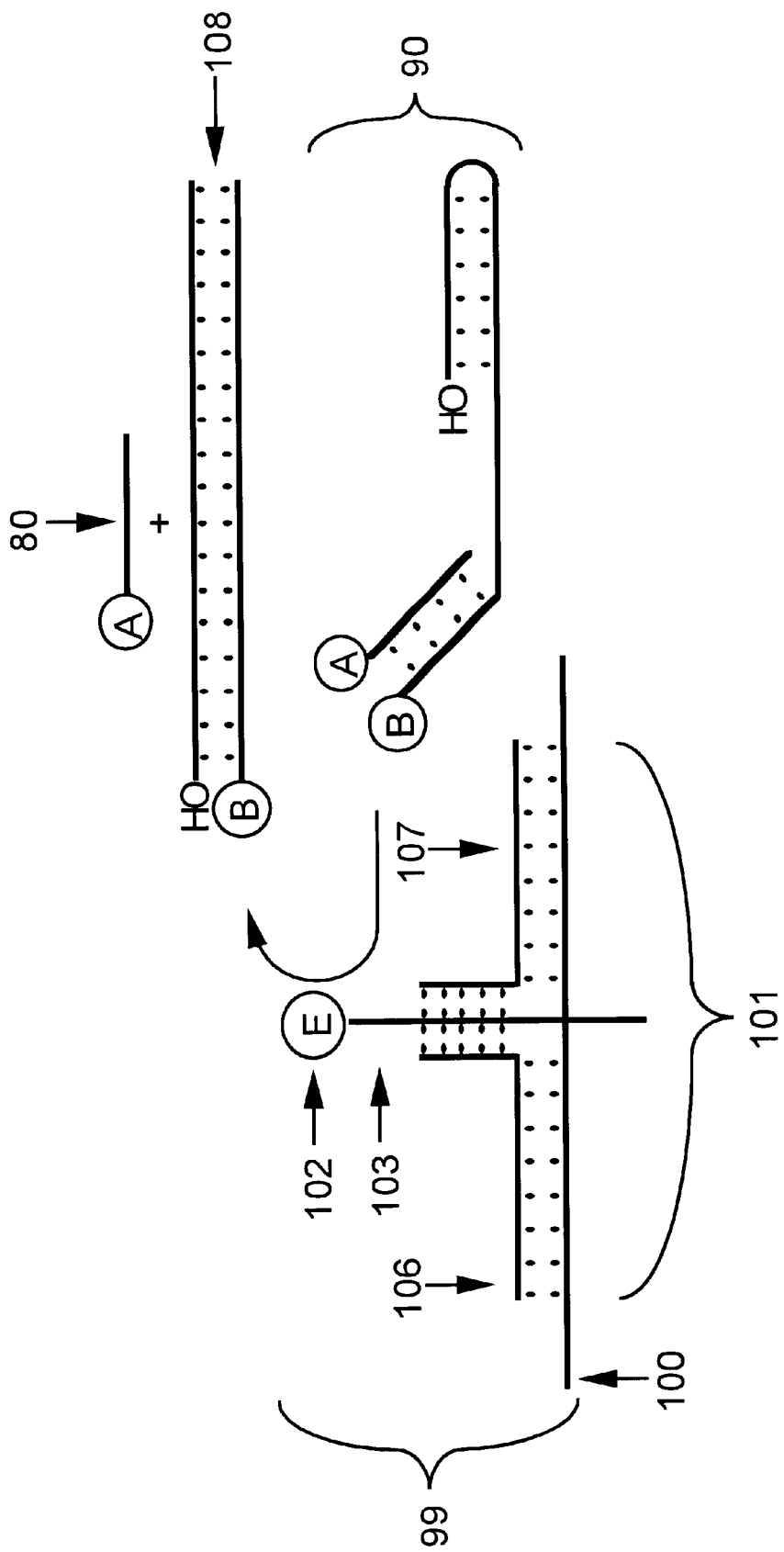
FIG. 21 is an illustration of a probe-based hybridization assay wherein a Substrate Detection Complex is used as a signal amplification process to detect the presence of the target molecule.

With reference to FIG. 21, an embodiment of using a Substrate Detection Complex in a probe-based hybridization assay to detect a target molecule is illustrated. The probe/target complex (99) to be detected using the Substrate Detection Complex (90) is formed from the target molecule (100), having a target sequence 101 to which the unlabeled probes 106 and 107 hybridize. The enzyme labeled probe 103, comprising enzyme moiety (102) is then further complexed to arms of the unlabeled probes 106 and 107. (See European Patent Application; EPA 849,363 for a discussion of the formation and utility of such complexes). According to the illustration, the enzyme (102), then acts upon the Substrate Detection Complex (90; See FIG. 20) to thereby extend the terminus of the hairpin stem and form the duplex 108. Formation of the duplex 108 result in release of the component polymer 80 and dissociation of the Substrate Detection Complex. Upon dissociation, there is a measurable change in detectable signal from at least one member of a Beacon Set which can be used to detect or identify the presence, absence or quantity of the target sequence or target molecule in the assay. Furthermore, signal amplification occurs because the polymerase enzyme can turn over many Substrate Detection Complexes to thereby produce a tremendous detectable change in signal attributable to the many dissociated Substrate Detection Complexes.

Immobilization of a Detection Complex To A Surface

One or more of the component polymers which comprise a Detection Complex, Substrate Detection Complex or PCR Detection Complex of this invention may optionally be immobilized to a surface for the purpose of formiing a support bound Detection Complex. The component polymer can be immobilized to the surface using the well known process of UV-crosslinking. Alternatively, the component polymer is synthesized on the surface in a manner suitable for deprotection but not cleavage from the synthesis support (See: Weiler, J. et al., "Hybridization based DNA screening on peptide nucleic acid (PNA) oligomer arrays", *Nucl. Acids Res.*, 25:, 2792–2799 (1997)). In still another embodiment, one or more component polymer is covalently linked to a surface by the reaction of a suitable functional group on the probe with a functional group of the surface (See: Lester, A. et al, PNA array technology. Presented at Biochip Technologies Conference in Annapolis (October, 1997)).

Methods for the attachment of polymers to surfaces generally involve the reaction of a nucleophilic group, (e.g. an amine or thiol) of the polymer to be immobilized, with an electrophilic group on the support to be modified. Alternatively, the nucleophile can be present on the support and the electrophile (e.g. activated carboxylic acid) present on the polymer. Because native PNA and other non-nucleic acid probes will typically possesses an amino terminus, they will not necessarily require modification to be immobilized to a surface (See: Lester et al., Poster entitled "PNA Array Technology"). Conversely, nucleic acid probes will generally be prepared in modified form (e.g. prepared as amine or thiol modified polynucleotides) using commercially available reagents and/or supports, if they are to be immobilized to a support.

Conditions suitable for the immobilization of a nucleic acid or PNA to a surface will generally be similar to those conditions suitable for the labeling of the polymer. The immobilization reaction is essentially the equivalent of labeling whereby the label is substituted with the surface to which the polymer is to be covalently immobilized. Numerous types of surfaces derivatized with amino groups, carboxylic acid groups, isocyantes, isothiocyanates and malimide groups are commercially available. Non-limiting examples of suitable surfaces include membranes, glass, controlled pore glass, polystyrene particles (beads), silica and gold nanoparticles.

Once a single component polymer is immobilized to a surface, the Detection Complex, PCR Detection Complex or Substrate Detection Complex can be formed simply by contacting the surface with a solution containing the other component polymers under conditions suitable for the complex to assemble. When immobilized to a surface, the Detection Complex, PCR Detection Complex or Substrate Detection Complex will exhibit little or no detectable signal until the component polymers are dissociated. The ability to retain one of the component polymers on a surface while releasing other component polymers into solution also provides a rapid means to separate the component polymers to thereby simplify detection in the assay.

Thus, Detection Complexes, PCR Detection Complexes and Substrate Detection Complexes formed from two or more component polymers, wherein only one component polymer is support bound, have advantages which are not available with unimolecular "Beacon" probes such as Molecular Beacons. Specifically, unimolecular "Beacon" probes tether the donor and acceptor moieties to a single molecule so it is not possible to completely separate the donor and acceptor moieties of a Beacon Set. By comparison, the hybridization induced dissociation of the Detection Complex, PCR Detection Complex or Substrate Detection Complex results in what is effectively an infinite distance separation between the moieties of the Beacon Set and can therefore lead to substantially more intense changes in detectable signal.

For example, upon dissociation of an immobilized Detection Complex, untethered polymers are released to the solution while tethered component polymers remain attached to the surface. Assuming the support bound polymer comprises the quencher moiety of the Beacon Set, the release of the fluorescently labeled component polymer into the solution will allow for simple separation from all quencher moiety prior to the analysis of the solution for fluorescence. Alternatively, the support bound polymer may comprise the fluorescent moiety of the Beacon Set, wherein the release of the quencher containing component polymer into the solution will simplify analysis of the support for fluorescence.

Advantageously, the support bound Detection Complexes of this invention can be easily regenerated merely by removing any hybridized target molecules from the surface. This can usually be done by exposing the surface to denaturing conditions such as treating the surface with a solution containing formamide and/or base (e.g. sodium hydroxide) or by washing the surface elevated temperature. The surface is then contacted with a quantity of labeled component polymer as is necessary to regenerate the support bound Detection Complex under suitable conditions.

Arrays of Detection Complexes

Arrays of probes have recently become well known as a means to simultaneously interrogate samples for numerous target sequences (See: U.S. Pat. No. 5,556,752, U.S. Pat. No. 5,837,832, U.S. Pat. No. 5,744,305, U.S. Pat. No. 5,843,655, U.S. Pat. No. 5,631,734, U.S. Pat. No. 5,770,722, U.S. Pat. No. 5,874,219 and U.S. Pat. No. 5,856,174, all herein incorporated by reference). Generally, the information which can be generated using such an array device is limited only by the number of different sequences which can be fit on the surface and the detection methodology chosen.

In still another embodiment, numerous different Detection Complexes and PCR Detection Complexes of this invention can be immobilized each at a specified position on the surface to thereby form an array of Detection Complexes wherein the probing sequence of the component probing polymers of the immobilized Detection Complexes are judiciously chosen to interrogate a sample which may contain one or more target molecules of interest. Because the location and composition of each Detection Complex or PCR Detection Complex is known, arrays of Detection Complexes can be used to simultaneously detect, identify or quantitate two or more target molecules present in the same sample. Thus, Detection Complex arrays will be particularly useful in diagnostic applications, in screening compounds for leads which might exhibit therapeutic utility (e.g. drug development) or in screening samples for factors useful in monitoring patients for susceptibility to adverse drug interactions (e.g. pharmacogenomics).

For example, the array of Detection Complexes may be formed such that for each Detection Complex, a fluorescently labeled probing polymer is immobilized to the surface for each of the different target molecules sought to be detected in a sample. At least one quencher containing annealing polymer is then hybridized to each probing polymer to thereby form each immobilized Detection Complex. Most preferably the same annealing polymer is used to form the many different Detection Complexes of the array. When the array is contacted with sample, hybridization of a target sequence to a particular probing polymer will directly or indirectly result in dissociation of a particular Detection Complex and therefore the released annealing polymer may be easily removed from the assay. Consequently, detection of a fluorescent signal at a particular location on the array is indicative of the presence and/or quantity of a target sequence in the sample which has hybridized at the position of a known probing sequence. Consequently, analysis of all fluorescence on the array can be used to simultaneously determine the presence, absence or quantity of two or more target molecules of interest which may be present in the same sample.

One additional advantage of such an array of Detection Complexes is the ease of regeneration/recycling. Specifically, once a single analysis of a sample is completed, the hybridized nucleic acid from the sample can be removed using conditions which dissociate the hybrids (e.g. denaturing conditions). The array of Detection Complexes can then be regenerated by rehybridization of quencher containing annealing polymers to the support bound probing polymers under suitable hybridization conditions. In preferred embodiments, all probing polymers comprise common interacting groups such that a single quencher containing annealing polymer is useful for quenching the fluorescence of all the different support bound probing polymers. An example of designing a common quencher containing annealing polymer useful for the assembly of multiple different Detection Complexes each comprising a different probing polymer is found in Examples 15, 16 and 17 of this specification.

III Methods Of Use And Applications For Detection Complexes, PCR Detection Complexes and Substrate Detection Complexes Method For The Detection Of A Target Sequence:

The Detection Complexes, PCR Detection Complexes and Substrate Detection Complexes of this invention are suitable for detecting or identifying the presence, absence or quantity of a target sequence of a target molecule. Consequently, this invention is also directed to methods for the detection, identification or quantitation of a target sequence and/or target molecule in a sample.

In one embodiment, the method comprises contacting the sample with a Detection Complex or PCR Detection Complex and then detecting or identifying changes in detectable signal attributable to the transfer of energy between the donor and acceptor moieties of a Beacon Set upon hybridization or the probing segment of the probing polymer to the target sequence or upon direct or indirect dissociation of the complex. The signal detected can then be correlated with the presence, absence or quantity of the target sequence and/or target molecule in the sample. Generally, quantitation will involve comparison of the signal to a standard curve generated using a standardized assay and known quantities of target sequence and/or target molecule in representative samples.

In another embodiment, the method comprises forming the Detection Complex after the probing polymer or probing polymers have been allowed to interact with the target sequence or target molecule of interest. In this embodiment, the extent of formation of the Detection Complex can be measured by the change in detectable signal of at least one member of the Beacon Set before and after the formation of the Detection Complex. Since the amount of probing polymer or polymers and annealing polymer or polymers added to the sample can be controlled and calculated, the extent of formation of the Detection Complex, and the measurable change in detectable signal derived therefrom, can be used to determine the presence absence or quantity of a target sequence or target molecule in a sample of interest.

In still another embodiment, the Detection Complex is a substrate for an enzyme wherein the target molecule of interest is detected because the activity of the enzyme on the Substrate Detection Complex generates detectable signal in the presence of, or in proportion to, the presence or quantity of target molecule in the sample. The method comprises contacting the sample with probes and enzyme configured to generate target dependent enzyme activity. Generally, the assay is designed as a probe-based assay wherein one of the probes which complexes with the target molecule is a probe-enzyme conjugate. The sample is then contacted with a Substrate Detection Complex and the changes in detectable signal attributable to the transfer of energy between the donor and acceptor moieties of a Beacon Set resulting from dissociation of the complex are then measured. Generally, quantitation will involve comparison of the signal to a standard curve generated using a standardized assay and known quantities of target sequence and/or target molecule in representative samples.

Exemplary Uses For The Methods Of The Invention:

When performing the methods of this invention, the Detection Complexes may be used as either probes, primers or substrates for enzymes. Because certain embodiments of Detection Complexes exhibit little intrinsic signal until dissociated, the methods are also particularly well suited to detecting a target sequence or target molecule in a cell, tissue or organism, whether living or not. Suitable methods include in-situ assays as well as assays performed on samples containing target molecules extracted from cells, tissues or organisms. Methods for in-situ hybridization as well as methods for the extraction and processing of nucleic acid for analysis are well known in the art.

For example, this invention is useful for detecting, identifying or quantitating the presence or quantity of an organism or virus in a sample through the detection of target nucleic acids associated with the organism or virus. (See: U.S. Pat. No. 5,641,631, entitled "Method for detecting, identifying and quantitating organisms and viruses" herein incorporated by reference). Similarly, this invention is useful for detecting, identifying or quantitating one or more species of an organism in a sample (See U.S. Pat. No. 5,288,611, entitled "Method for detecting, identifying and quantitating organisms and viruses" herein incorporated by reference). This invention is also useful for determining the effect of antimicrobial agents on the growth of one or more microorganisms in a sample (See: U.S. Pat. No. 5,612,183, entitled "Method for determining the effect of antimicrobial agents on growth using ribosomal nucleic acid subunit subsequence specific probes" herein incorporated by reference). This invention is also useful for determining the presence or quantity of a taxonomic group of organisms in a sample (See: U.S. Pat. No. 5,601,984, entitled "Method for detecting the presence of quantity of a taxonomic group of organisms using specific r-RNA subsequences as probes" herein incorporated by reference. As used herein, non-limiting examples of organisms include microorganisms, yeast, fungi, bacteria, microbacteria, algae, viruses and spores.

The methods of this invention are also particularly useful for the detection of bacteria and eucarya in food, beverages, water, pharmaceutical products, personal care products, dairy products or environmental samples. Preferred beverages include soda, bottled water, fruit juice, beer, wine or liquor products. Suitable methods will also be particularly useful for the analysis of raw materials, equipment, products or processes used to manufacture or store food, beverages, water, pharmaceutical products, personal care products, dairy products or environmental samples.

Alternatively, the methods may be performed to diagnose a condition of medical interest. For example the methods, kits and compositions of this invention will be particularly useful for the analysis of clinical specimens or equipment, fixtures or products used to treat humans or animals. In one preferred embodiment, the assay may be used to detect a target sequence which is specific for a genetically based disease or is specific for a predisposition to a genetically based disease. Non-limiting examples of diseases include, β-Thalassemia, sickle cell anemia, Factor-V Leiden, cystic fibrosis and cancer related targets such as p53, p10, BRC-1 and BRC-2. In still another embodiment, the target sequence may be related to a chromosomal DNA, wherein the detection, identification or quantitation of the target sequence can be used in relation to forensic techniques such as prenatal screening, paternity testing, identity confirmation or crime investigation.

Other non-limiting examples of uses for the methods of this invention include the analysis or manipulation of plants and genetic materials derived therefrom as well as biowarfare reagents. Detection Complexes will also be particularly useful in diagnostic applications, in screening compounds for leads which might exhibit therapeutic utility (e.g. drug development) or in screening samples for factors useful in monitoring patients for susceptibility to adverse drug interactions (e.g. pharmacogenomics).

Operation Of The Method On Surfaces And In Arrays:

The methods of this invention may be performed when one or more of the assay components are immobilized to a surface. According to the method, the target sequence may be immobilized (covalently linked, electrostatically bound or adsorbed) to a surface such that the assay is performed by contacting the surface with the other assay components including the Detection Complex, PCR Detection Complex or Substrate Detection Complex. Alternatively, the Detection Complex, PCR Detection Complex or Substrate Detection Complex is immobilized or tethered to a surface through one or more of its component polymers. In yet another embodiment, the sample is contacted with an array comprising at least two immobilized or tethered Detection Complexes or PCR Detection Complex. Arrays are typically used to simultaneously interrogate a sample for the presence, absence or quantity of two or more unique target sequences of interest. Surface bound targets or Detection Complexes are particularly useful in certain applications since one can control release of at least one component polymer from the surface in response to the presence of the target sequence or target molecule.

In one embodiment, the target molecule comprising the target sequence is immobilized to a surface. Assuming the Detection Complex, PCR Detection Complex or Substrate Detection Complex dissociates to release the a fluorescently labeled polymer into solution, the solution can be assayed for the presence and quantity of the fluorophore as a means to determine the presence and/or quantity of immobilized target sequence or target molecule. Alternatively, the quencher labeled annealing polymer is released to the solution and washed away thereby generating a detectable fluorescently labeled probing polymer hybridized and concentrated on the surface wherein signal intensity is used to detect or quantitate the target sequence or target molecule in the sample.

Similarly, the Detection Complex, PCR Detection Complex or Substrate Detection Complex maybe immobilized to the surface. In this embodiment, the presence of the target sequence or target molecule causes the release of either the fluorophore labeled polymer or the quencher labeled polymer into the solution. Consequently, the detection method will involve either analysis of the solution released from the surface or analysis of signal concentrated on the surface as the means to determine the presence, absence or quantity of target sequence or target molecule in the sample.

Advantages of Using Common Annealing Probes:

Regardless of whether they are immobilized to a surface or used in solution, when multiple Detection Complexes, PCR Detection Complexes or Substrate Detection Complexes are used in a single assay, it is an important feature of this invention that the same annealing probe may be used to form a complex with two or more different probing polymers wherein the two or more different probing polymers hybridize to two or more unique target sequences or target molecules of interest. The ability to utilize one common component polymer in the formation of many different Detection Complexes, PCR Detection Complexes or Substrate Detection Complexes, each suitable for detecting a different and unique target, is particularly advantageous to the manufacturing of assays. Specifically, the manufacturing process can be substantially simplified since the many different singularly labeled probing polymers comprising different independently detectable moieties will form a Detection Complex in the presence of a common annealing polymer which itself can be manufacture in bulk and mixed with the many different probing polymers. In preferred embodiments, many different probing polymers can be mixed with the single annealing polymer in a single tube to thereby simultaneously form the many different Detection Complexes, PCR Detection Complexes or Substrate Detection Complexes useful in a single multiplex assay.

Moreover, preparing and purifying nucleic acid and PNA oligomers with multiple labels can be cumbersome and laborious. Because the two labels of a Beacon Set can be each be attached to a different polymer of the Detection Complex, PCR Detection Complex or Substrate Detection Complex, the preparation of component polymers, each comprising a single label, will be much simpler, less time consuming and less expensive as compare with the preparation of unimolecular "Beacon" probes in which the two or more moieties of a Beacon Set are tethered to the same polymer.

Preferred Assay Formats:

Because Detection Complexes, PCR Detection Complexes or Substrate Detection Complexes are self-indicating, the methods of this invention are particularly well suited to analysis performed in a closed tube assay format. By closed tube assay format we mean an assay wherein manipulation of the assay sample need not be performed (e.g. separation of assay components) during or after the assay in order for the result to be determined. For example, the assay vessel may be, but is not necessarily, sealed provided that at least one detectable parameter of the assay sample can be measured (e.g. fluorescence) through the walls of the vessel. In preferred embodiments, the result is visible to the naked eye without the aid of sophisticated instrumentation. For example, fluorescence is visible when UV light is applied to the tube containing the sample. In most preferred embodiment, the sample can be analyzed in real-time as well as at the end-point of the assay. Examples of commercially available instruments which are capable of both real-time as well as end-point determination of closed tube assays include the Light Cycler from Idaho Technologies and the Prism 7700 from Perkin Elmer. These instruments can measure fluorescence of any sample in the instrument in real-time as well as at the end-point of the assay without any requirement that the tube be opened or the contents of the reaction become exposed.

Preferred closed tube assays comprise the detection of a target sequence which has been produced in an assay. The target sequence may be produced by a transcription or ligation but is preferably amplified in a nucleic acid amplification reaction. When utilized in a transcription, ligation or polymerase extension reaction (e.g. PCR), the Detection Complex may be directed to a target sequence within newly synthesized or amplified nucleic acid. Alternatively, the Detection Complex may participate as a primer in the nucleic acid synthesis or amplification reaction. Non-limiting examples of suitable nucleic acid synthesis or amplification reactions include Polymerase Chain Reaction (PCR), Ligase Chain Reaction (LCR), Strand Displacement Amplification (SDA), Transcription-Mediated Amplification (TMA), Q-beta replicase (Q-beta) and Rolling Circle Amplification (RCA). It is expected that other new methods for synthesizing or amplifying nucleic acid will be become known and commonly utilized by those of skill in the art. Use of the Detection Complexes of this invention to monitor any methods (new or old) for the synthesis and/or amplification of nucleic acid is anticipated by the disclosure of this invention.

PCR is a preferred assay format used to practice this invention. The PCR catalytic process is repetitive, and therefore, many copies of a nucleic acid target molecule comprising a target sequence can be rapidly generated in a PCR reaction. Preferably, one or more Detection Complexes perform as the forward and/or reverse primers in the PCR reaction. When used as a primer, the probing polymer of one or more Detection Complexes is incorporated into the amplified nucleic acid. Whether or not the Detection Complex is a primer, PCR is the secondary "triggering" event which causes dissociation of the Detection Complex. Thus, signal is generated in proportion to the amount of newly formed nucleic acid (i.e. amplicons). Consequently, the Detection Complex may be used to detect the presence, absence or quantity of a target sequence of a target molecule in a sample. The utility of using a Detection Complex as a PCR primer is demonstrated in Examples 15, 16, 17 and 18 of this Specification.

Use of Detection Complexes As Primers In PCR Applications:

In a preferred embodiment, the methods and compositions of this invention are used in PCR reactions wherein one or more PCR Detection Complexes are used as one or both of the forward and or reverse primers in the PCR reaction provided however that the PCR Detection Complexes of this invention need not comprise at least one non-nucleic acid polymer since the art hereinbefore has taught that such complexes are not suitable for use in PCR (See: Tyagi2 et al., WIPO patent application WO95/13399 and the Background section of this Specification). Consequently, the PCR Detection Complexes of this invention included complexes comprised solely of nucleic acid polymers as well as complexes formed using one or more non-nucleic acid polymers. Preferably however, at least one of the component polymers is a non-nucleic acid polymer and most preferably a PNA. The method is used for the detection or identification of a nucleic acid target molecule of interest in a sample, wherein the nucleic acid target molecule comprises one or more priming sites to which the probing segment of the probing polymer of the PCR Detection Complex hybridizes to initiate a primer extension reaction. The primer extension reaction can be initiated in an artificial system such as a tube or in a cell (in-situ) such as with the technique known as PRINS (See: Serakinci et al., Nature Biotechnology, 17: 200–201 (February, 1999).

An illustration of a fluorescence based PCR assay is illustrated in FIGS. 4–7. With reference to FIG. 4A, a double stranded plasmid template (60) is illustrated. As illustrated, one or both of the forward (61) or reverse (62) primers of the PCR reaction can be a PCR Detection Complex.

An expansion of the polymerase reaction initiated by the forward primer (61) is illustrated in FIG. 4B. As illustrated, a single strand of the plasmid (63) comprising the target sequence (64) is shown. The polymerase (65) thereby generates the complementary strand of the plasmid. As illustrated, the probing segment (66) of the probing polymer (68) hybridizes to the target sequence (64). The annealing polymer (69) hybridizes to the interacting groups (67) of the probing polymer (68) to thereby form the PCR Detection Complex. As illustrated, the detection complex does not dissociate upon hybridization to the target sequence since the interacting groups (67) of the probing polymer do not hybridize to the target sequence (64). The PCR Detection Complex illustrated comprises a first fluorophore (F) and a quencher (Q).

Figure 5:
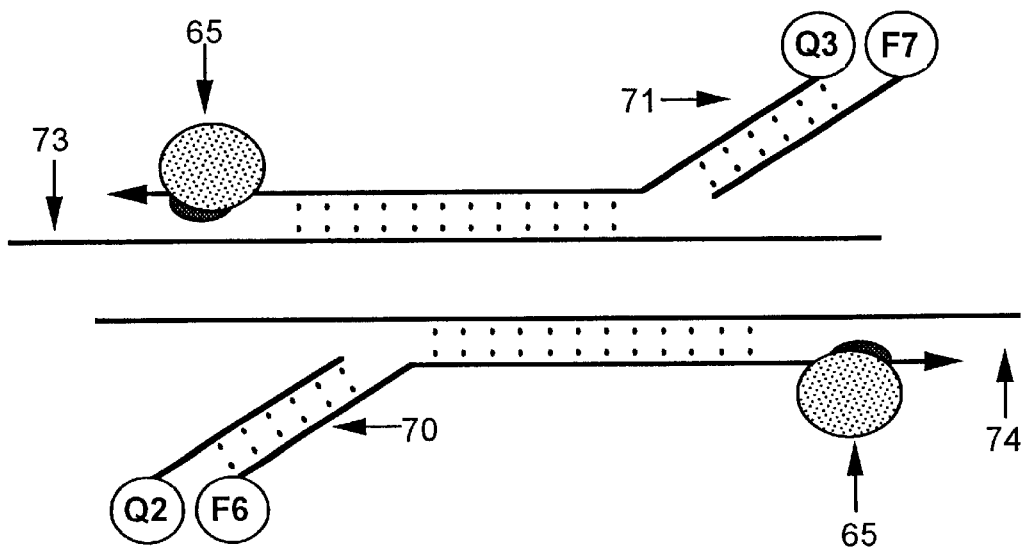
FIG. 5 illustrates the operation of PCR in the first round wherein both the forward and reverse primers are Detection Complexes.

First round products of PCR are illustrated in FIG. 5. As illustrated, both the forward (70) and reverse primers (71) are PCR Detection Complexes. Complementary strands of the plasmid are illustrated as 73 and 74. The polymerase (65) will copy the plasmid until it detaches. As illustrated, the PCR Detection Complexes are not yet dissociated. Therefore each fluorophore F6 and F7 is quenched by the quencher moieties Q2 and Q3, respectively.

Figure 6:
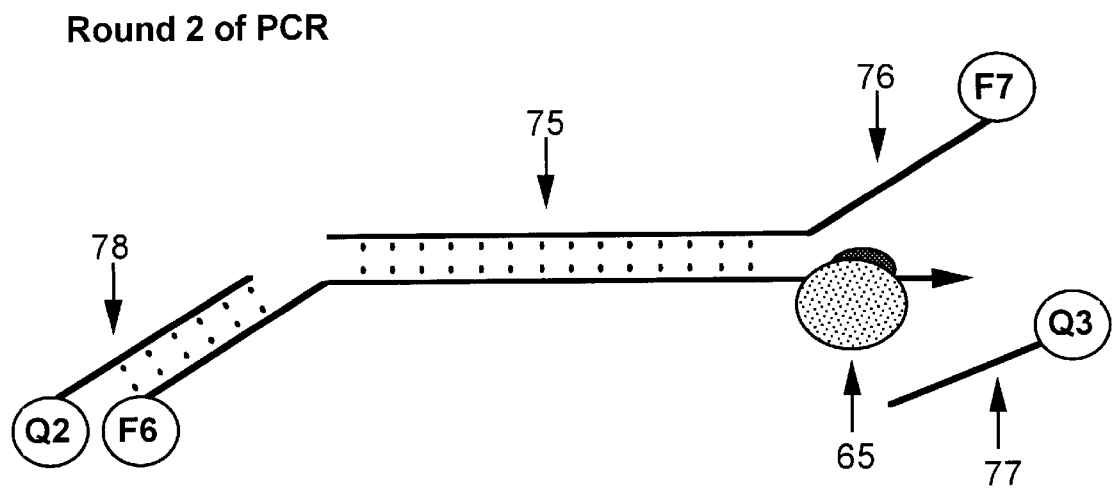
FIG. 6 illustrates the operation of PCR in the second round wherein both the forward and reverse primers are Detection Complexes.

The second round of PCR is illustrated in FIG. 6. With reference to FIG. 6, the polymerase enzyme copies back on the round one polymerization product (75). As it reaches the end of the template strand, the polymerase (65) will push the annealing polymer (77) off the template thereby dissociating the PCR Detection Complex and releasing the annealing polymer into the solution. Consequently, this indirect dissociation of the PCR Detection Complex is a secondary "triggering" event which results in the generation of the detectable signal of the assay.

With reference to FIG. 6, it becomes apparent that if the probing polymer is a nucleic acid and the interacting groups (76) comprise nucleotides, then the polymerase will copy past the hybridization site of the probing segment of the PCR Detection Complex to thereby extend the amplicon past the original priming site(s) of the template. Generation of the amplicon which is longer than the distance between the termini of the priming sites on the template will result in preferred (enriched) reproduction of the amplicons since in subsequent rounds of PCR the entire nucleotide sequence of the probing polymer will be complementary to the termini of the amplicon whereas only the probing segment of the probing polymer is complementary to the target sequence (Review the discussion of FIG. 2 in the section entitled "Formation and Stability of Detection Complexes, PCR Detection Complexes and Substrate Detection Complexes"). The increased thermodynamic stability of the complex formed between the amplicon and the probing polymer will thereby result in enriched amplification of the amplicons over reproduction of the template in subsequent rounds of PCR.

It likewise follows that the extension of the amplicons past the hybridization sites on the template enables manipulations of the amplicons which might not otherwise be available since the composition of the interacting groups can be customized. For example, the interacting groups used to form and stabilize the PCR Detection Complex may be designed so that the amplicons formed in the PCR reaction will comprise terminal restriction sites which are not found within the template. Thus, the amplicons can be directly cloned once the PCR reaction is completed.

Figure 7:
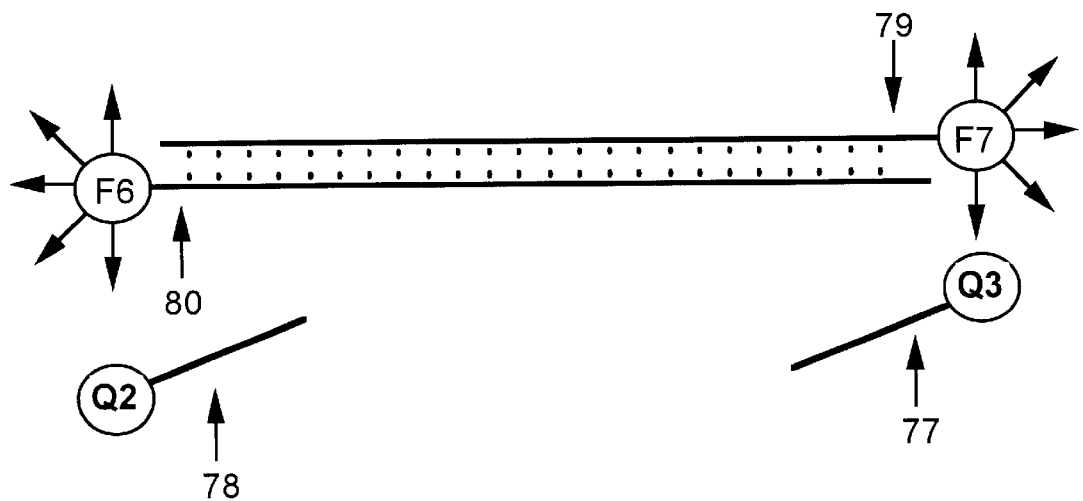
FIG. 7 illustrates an amplicon prepared in a PCR amplification wherein both the forward and reverse primers are Detection Complexes.

With reference to FIG. 7, the final PCR amplicon is illustrated. As illustrated, the fluorescence of each fluorophore (F6 & F7) at each terminus of the amplicon (79 and 80) can be detected since the Detection Complexes have been dissociated thereby releasing into solution the annealing polymers (77 and 78) comprising the quencher moieties (Q2 & Q3). As previously discussed the fluorophores and quencher moieties may be the same or different. Moreover, a single assay may be multiplexed to thereby identify or quantitate two or more unique target sequences. When multiplexing, it is preferable to use common PNA annealing polymers comprising a quencher moiety and nucleic acid primers for two or more target molecules of interest wherein one or both of the primers of each set are labeled with independently detectable moieties such that production of the amplicons for each unique target molecule are independently detectable. An exemplary multiplex PCR assay is found in Example 16 of this specification.

A. PCR Clamping:

The operation of PCR reactions may be improved using a process known as PCR clamping (See: Ørum et al., Nucl. Acids Res. 21: 5332–5336 (1993) and WIPO patent application WO93/25706) to thereby produce an assay suitable for point mutation discrimination. The PCR Detection Complexes described above can therefore be used in combination with PCR clamping to thereby generate closed tube assays capable of end-point and real-time point mutation discrimination. An example of using PCR Detection Complexes in combination with PCR clamping to achieve point mutation discrimination can be found in Example 17 of this Specification.

B. Internal Assay Monitoring/Independent Feature Identification:

Detection Complexes can be used simultaneously with unimolecular "Beacon" probes such as hairpin forming nucleic acid Molecular Beacons (See: Tyagi et al., Tyagi2 et al. and Tyagi3 et al.), PNA Molecular Beacons (See: U.S. Ser. No. 08/958,532 (allowed) and copending U.S. Ser. No. 09/179,298, both incorporated herein by reference) and Linear Beacons (See: copending U.S. Ser. No. 09/179,162, all of which are herein incorporated by reference)). Commingling unimolecular "Beacon" probes and PCR Detection Complexes in the same reaction may prove particularly useful in multiplex assays wherein the activity of each probe set is independently detectable. For example, the simultaneous use may prove very beneficial as an internal means to monitor proper assay performance or otherwise independently identify or measure a feature or features of the amplicon generated in the assay.

i. Internal Assay Monitoring:

In one embodiment, an assay is designed such that a PCR Detection Complex functions as a primer in the PCR assay and a unimolecular "beacon" probe (e.g. a hairpin forming nucleic acid Molecular Beacon, a PNA Molecular Beacon or a Linear Beacon), comprising an independently detectable moiety, hybridizes to a hybridization site within the amplicon to thereby generate an independently detectable signal. The combination of expected independently detectable signals from both the PCR Detection Complex and the unimolecular probe can be used to monitor the assay. For example, if only one of the signals from either the PCR Detection Complex or unimolecular beacon is detected or is dominate in the assay, this would be a result indicative of a problem such as mis-priming or primer dimer formation. However, detection of each independently detectable signal for both the activity of the PCR Detection Complex and the unimolecular "beacon" probe can be used to insure accurate assay performance.

ii. Independent Feature Identification:

In still another embodiment, this methodology can be applied to the use of amplification as a means to confirm the presence of a general feature of interest in a sample as well as simultaneously and independently determine one or more specific features of the amplicon (See: Nycz et al., European Patent Application No. 725,148, for an assay which amplifies a non-species specific target followed by a group or species specific detection of the amplification products). For example, the assay of this invention could be used to detect the presence of organisms of a genus and simultaneously determine whether one or more species of the organism were also present. Alternatively, the assay could be used to determine whether a general target was present in the sample and simultaneously determine whether wild type, mutant or both versions were present even if the difference between wild type and mutant comprises a single point mutation. An exemplary assay can be found in Example 18 of this Specification.

By way of example, the PCR Detection Complexes could be chosen to amplify all bacterial nucleic acid in the sample and thereby generate a green signal (as for example by using one or more fluorescein labeled PCR Detection Complexes). Therefore, by choosing appropriate PCR Detection Complex primers, the generation of a green signal in the assay will be indicative of the presence of bacteria. In addition, one or more unimolecular "Beacon" probes could also be included in the assay to, for example, determine whether certain species of bacteria are present. For example, one unimolecular "Beacon" probe could be labeled with a blue fluorophore and be directed to a target sequence which would be present in the amplicon if nucleic acid of *E. coli* were present in the sample. The assay could be further multiplex by the addition of another unimolecular "Beacon" probe labeled with a red fluorophore and directed to a target sequence which would be present in the amplicon if nucleic acid of *S. aureus* were present in the sample. Thus, the absence of a signal would indicate no bacteria were in the sample. A green signal would indicate bacteria were present but neither *E. coli* or *S. aureus* were present. Similarly, a blue and green signal would indicate *E. coli* was present; a red and green signal would indicate that *S. aureus* was present and a blue, green and red signal would indicate that both *E. coli* and *S. aureus* were present in the sample. Consequently, this invention contemplates closed tube multiplex assays suitable for the simultaneous detection of both properties generic to a population as well as properties specific to the population. Applicants are unaware or any method suitable for simultaneously generating both genus and species information in a single assay which utilizes a closed tube assay format. Consequently, this is a most unique and useful application of the methods and compositions of this invention.

Additionally, the use of both unimolecular "Beacon" probes (See copending U.S. Ser. No. 09/179,162) and the PCR Detection Complexes of this invention (See Example 17) can each independently be used to detect point mutations in a closed tube assay format. Consequently, the commingling of PCR Detection Complexes and unimolecular "Beacon" probes in a single assay facilitates the simultaneous collection of both genus and species information in a single closed tube assay format suitable for real-time or end-point analysis even if the differentiating factor between each of the genus and species identification sought lies in a point mutation of a nucleic acid.

Multiplex Applications

As illustrated by the preceding examples, Detection Complexes and PCR Detection Complexes are particularly useful for applications involving multiple Beacon Sets wherein each Beacon Set contains at least one independently detectable moiety. Preferably, the independently detectable moieties are independently detectable fluorophores. For example, a mixture of four different Detection Complexes may be used to detect each of four different target sequences, wherein each Detection Complex comprises one or four independently detectable fluorophores. For this example, detection of the presence, absence or quantity of the four different target sequences is made possible by the detection and/or quantitation of each of the four different independently detectable fluorophores after the mixture has been incubated with the sample of interest. As previously discussed, the Detection Complexes may also be used in assays wherein the independently detectable moieties are used to distinguish the operation of the same or different processes occurring in the same assay. Such multiplex assays are possible whether the Detection Complexes are used as probes or as primers. Examples 16 and 18 of this Specification are examples of Multiplex Applications utilizing Detection Complexes or Detection Complexes in concert with unimolecular "Beacon" probes.

IV. Method For The Formation of Detection Complexes

In still another embodiment, this invention is directed a method for forming a Detection Complex. The method comprises mixing together two or more component polymers under conditions which facilitate complex formation. In certain embodiments, it is preferable to form the Detection Complexes before, during or even after some or all of the other processes of the assay are performed provided that the change in detectable signal from at least one member of a Beacon Set occurring in the assay can be correlated with the presence, absence or quantity of a target sequence or target molecule of interest in the sample. Detection Complexes formed by the method of this invention have been described under the heading "Compositions Of This Invention". Detection Complexes formed by this method include PCR Detection Complexes as well as Substrate Detection Complexes.

V. Kits of the Invention

This invention is further directed to kits which comprise the component polymers of a Detection Complex and other reagents useful for the practice of methods of this invention. Kits of this invention are suitable for detecting or identifying the presence, absence or quantity of a target sequence or target molecule which may be present in a sample of interest. As received by the end-user, the Detection Complex may be preassembled or alternatively, the end-user may need to mix two or more of the component polymers to thereby generate the Detection Complex. The appended claims are intended to apply to kits wherein the component polymers exist individually as well as kits containing preassembled Detection Complexes. Detection Complexes suitable for the kits of this invention have been described under the heading "Compositions Of This Invention". Detection Complexes suitable for use in kits include PCR Detection Complexes as well as Substrate Detection Complexes.

Preferred kits of this invention comprise all the reagents to perform a PCR reaction wherein each of the one or more Detection Complexes or PCR Detection Complexes of the kit are used to monitor a sample for the presence, absence or quantity of a target sequence or target molecule of interest. In preferred embodiments, one or more of the Detection Complexes of the kit perform as the primers in the PCR reaction. For the Detection Complex to operate as a primer in PCR, the probing polymer of at least one Detection Complex must comprises a probing segment, bearing a 3'-hydroxyl group. Preferably, the probing polymer comprises nucleobase containing interacting groups which do not sequence specifically interact with the target sequence but which only interact with the nucleobases of interacting groups of the annealing polymer. Moreover, preferably, the annealing polymer comprises nucleobase containing interacting groups which are the exact complement to the interacting groups of the probing polymer.

A typical PCR kit will contain at least two primers (wherein at least one may be a PCR Detection Complex), at least one Detection Complex or PCR Detection Complex, nucleotide triphosphates, polymerase enzyme (preferably thermostable polymerase) and a buffer solution (with controlled ionic strength, controlled magnesium content and pH modulator).

Having described the preferred embodiments of the invention, it will now become apparent to one of skill in the art that other embodiments incorporating the concepts described herein may be used. It is felt, therefore, that these embodiments should not be limited to disclosed embodiments but rather should be limited only by the spirit and scope of the following claims.

EXAMPLES

Example 1

Synthesis of N-α-(Fmoc)-N-ε-(NH$_2$-L-Lysine-OH

To 20 mmol of N-α-(Fmoc)-N-ε-(t-boc)-L-lysine-OH was added 60 mL of 2/1 dichloromethane (DCM)/trifluoroacetic acid (TFA). The solution was allowed to stir until the tert-butyloxycarbonyl (t-boc) group had completely been removed from the N-α-(Fmoc)-N-ε-(t-boc)-L-lysine-OH. The solution was then evaporated to dryness and the residue redissolved in 15 mL of DCM. An attempt was then made to precipitate the product by dropwise addition of the solution to 350 mL of ethyl ether. Because the product oiled out, the ethyl ether was decanted and the oil put under high vacuum to yield a white foam. The white foam was dissolved in 250 mL of water and the solution was neutralized to pH 4 by addition of saturated sodium phosphate (dibasic). A white solid formed and was collected by vacuum filtration. The product was dried in a vacuum oven at 35–27° C. overnight. Yield 17.6 mmol, 88%.

Example 2

Synthesis of N-α-(Fmoc)-N-ε-(dabcyl)-L-Lysine-OH ("Fmoc-K(dabcyl)-OH")

To 1 mmol of N-α-(Fmoc)-N-ε-(NH$_2$)-L-Lysine-OH was added 5 mL of N,N'-dimethylformamide (DMF) and 1.1 mmol of trifluoroacetic acid. This solution was allowed to stir until the amino acid had completely dissolved.

To 1.1 mmol of 4-((4-(dimethylamino)phenyl)azo) benzoic acid, succinimidyl ester (Dabcyl-NHS; Molecular Probes, P/N D-2245) was added 4 mL of DMF and 5 mmol of diisopropylethylamine (DIEA). To this stirring solution was added, dropwise, the N-α-(Fmoc)-N-ε-(NH$_2$)-L-Lysine-OH solution prepared as described above. The reaction was allowed to stir overnight and was then worked up.

The solvent was vacuum evaporated and the residue partitioned in 50 mL of DCM and 50 mL of 10% aqueous citric acid. The layers were separated and the organic layer washed with aqueous sodium bicarbonate and again with 10% aqueous citric acid. The organic layer was then dried with sodium sulfate, filtered and evaporated to an orange foam. The foam was crystallized from acetonitrile (ACN) and the crystals collected by vacuum filtration. Yield 0.52 mmol, 52%.

Example 3

Synthesis of bis-(2-methoxyethyl)amidyl-diglycolic acid

To 500 mmol of diglycolic anhydride stirring in 800 mL of dichloromethane (DCM) was added dropwise, 1.1 mole of bis(2-methoxyethyl)amine (Aldrich Chemical). The reaction was allowed to stir for 2 hours and then 280 mL of 6N HCl was added dropwise. The contents were then transferred to a separatory funnel and allowed to separate. The DCM layer was removed and the aqueous layer extracted with 100 mL of DCM. The combined DCM layers were then extracted with 100 mL of 10% aqueous citric acid. The DCM layer was then separated, dried (Na$_2$SO$_4$), filtered and evaporated to yield 73.8 g (296 mmole; 59% yield). A kugelrorh was then used to remove traces of solvent (product was eated to 60° C. at approximately 180 μM Hg but was not distilled).

Example 4

Synthesis of N-[N"-Fmoc-(2"-aminoethyl)]-N-[N,N'-(2-methoxyethyl)amidyl-diglycolyl]glycine ("Fmoc-"E"aeg-OH")

To 60 mmol of Fmoc-aeg-OH (PerSeptive Biosystems, Inc.) was added 360 mL of MilliQ water, 180 mL of acetone, 120 mmol of NaHCO$_3$ and 60 mmol of K$_2$CO$_3$. This solution was allowed to stir until all the Fmoc-aeg-OH had dissolved (approx. 2 hr.) and then the solution prepared, as described below, was added.

To 70 mmol of bis-(2-methoxyethyl)amidyl-diglycolic acid was added 120 mL of anhydrous acetonitrile (Fluka Chemical), 240 mmol of N-methylmorpholne (NMM; Fluka Chemical) and 75 mmol of trimethylacetyl chloride (Aldrich Chemical). The solution was allowed to stir at room temperature for 30 minutes and then added dropwise to the solution of Fmoc-aeg-OH which was prepared as described above.

After the combined solutions stirred for 1 hr and tlc analysis indicated complete reaction, 6N HCl was added to the reaction until the pH was less than 2 by paper. The organic solvent was then removed by vacuum evaporation. The remaining aqueous solution was then transferred to a separatory funnel and extracted 2× with 250 mL of ethyl acetate. The combined ethyl acetate layers were dried (Na$_2$SO$_4$), filtered and evaporated to yield 41.5 g of an oil.

This crude product was purified by column chromatography using a reversed phase stationary phase (C18) and a gradient of aqueous acetonitrile to elute the product and remove the pivalic acid. Though not visible by tlc, the elution of the pivalic acid can be monitored by smell. The pivalic acid can be almost completely eluted from the column prior to elution of the product. Elution of the product can be monitored by tlc. Yield 26.8 g (47 mmol; 78%). An "E" modification of a PNA or polyamide has the formula:

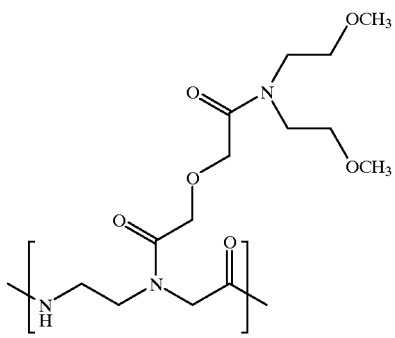

Example 5

Synthesis of N,N'-(2-methoxyethyl)-glycine-tert-butyl ester

To 1.1 mole of bis(2-methoxyethyl)amine (Aldrich Chemical) was added dropwise 500 mmol of tert-butyl chloroacetate (Aldrich Chemical). The reaction was allowed to stir for three days and was then worked up.

To the final reaction contents was added 250 mL of DCM and 200 mL of water. To this stirring solution was added portionwise, 300 mmol of solid potassium carbonate ($K_2CO_3$). After completely mixing, the layers were separated. The DCM layer was washed once with a volume of water, dried ($Na_2SO_4$), filtered and evaporated to yield 66.3 g of a very thin yellow oil. This crude product was Kugelrorh distilled at 60° C. (200–500 $\mu$M Hg) to yield 58.9 g of a clear colorless oil (238 mmol; 95%).

Example 6

Synthesis of N,N'-(2-methoxyethyl)-glycine

To the purified (stirring) N,N'-(2-methoxyethyl)-glycine-tert-butyl ester was slowly added 12.1 mL of concentrated hydrochloric acid. The reaction was allowed to stir overnight and then the byproducts (e.g. water, HCl, isobutylene) were removed by vacuum evaporation. $^1$H-MNR analysis indicated the t-butyl ester was hydrolyzed but it appeared that there was water and HCl still present. The crude product was co-evaporated 2× from ACN but water and HCl were still present.

To eliminate impurities, a 4.4 g sample was removed from the crude product and Kugelrorh distilled at 135–155° C. (100–200 $\mu$M Hg with rapidly dropping pressure after distillation began). Yield 4.2 g (18.4 mmol; 95% recovery of thick clear colorless oil). The distilled product did not contain any water or HCl.

Example 7

Synthesis of N-[N"-Fmoc-(2"-aminoethyl)]-N-[N, N"-(2-methoxyethyl)-glycyl]glycine ("Fmoc-"+"aeg-OH")

To 8 mmol of Fmoc-aeg-OH (PerSeptive Biosystems, Inc.) was added 24 mL of acetone and 40 mL of MilliQ water. To this stirring solution was added 16 mmol of $NaHCO_3$ and 8 mmol of $K_2CO_3$. This solution was allowed to stir until all the Fmoc-aeg-OH had dissolved (approx. 1 hr.) and then the solution prepared, as described below, was added.

To 9 mmol of N,N'-[bis-(2-methoxyethyl])-glycine was added 20 mL of anhydrous acetonitrile (Fluka Chemical), 9 mmol diisopropylethylamine (DIEA, Aldrich Chemical), 27 mmol of N-methylmorpholine (NMM; Fluka Chemical) and 9.3 mmol of trimethylacetyl chloride (Aldrich Chemical). The solution was allowed to stir at room temperature for 30 minutes and the added dropwise to the solution of Fmoc-aeg-OH which was prepared as described above.

After the combined solutions stirred for 1 hr and tlc analysis indicated complete reaction, the organic solvents were removed by vacuum evaporation. The remaining aqueous solution was then acidified to pH 7.0 by the portionwise addition of citric acid. The solution was then transferred to a separatory funnel and extracted 2× with 35 mL of ethyl acetate. No product was present in the organic layer so it was discarded.

The pH of the aqueous solution was then adjusted up and down until the solution got cloudy at approximately pH 8, by paper. The solvent was then transferred back to the separatory funnel and extracted with 25 mL of DCM. Because product was present in the organic layer, the aqueous layer was extracted again 3× with DCM. All DCM layers were combined and back extracted with 5% sodium bicarbonate solution. The pH was again adjusted to about pH 8.0. The aqueous layer was extracted several times with DCM and all DCM layers were combined, dried ($Na_2SO_4$), filtered and evaporated to yield approximately 5.0 g of a white solid.

This crude product was dissolved in DCM and precipitated into a mixture of 2/1 hexane/diethyl ether. The final product was collected by vacuum filtration. Yield 2.97 g (5.8 mmol; 72% yield). An "+" modification of a PNA or polyamide has the formula:

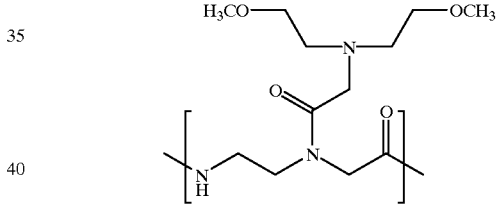

Example 8

General Procedure For The Synthesis Of PAL-Peg/PS Synthesis Supports Suitable For Preparing Polyamides Having C-Terminal Modifications The Fmoc-K(dabcyl)-OH, Fmoc-"E"aeg-OH and Fmoc-"+"aeg-OH synthons were used to prepare synthesis supports useful for the preparation of oligomers comprising one or more C-terminal "dabcyl", "E" or "+" moieties. Though the Fmoc-K(dabcyl)-OH, Fmoc-"E"aeg-OH and Fmoc-"+"aeg-OH synthons can be, and were, used directly in the automated instrument, the preparation of prederivatized supports is preferred because less synthon is required to prepare the bulk support.

In the first step, the fluorenylmethoxycarbonyl (Fmoc) group of commercially available Fmoc-PAL-Peg-PS synthesis support (PerSeptive Biosystems, Inc.; P/N GEN913384) was removed by treatment, in a flow through vessel, with 20% piperidine in N,N'-dimethylformamide (DMF) for 30 minutes. The support was then washed with DCM. Finally the support was washed with DMF and dried with a flushing stream of argon.

In the second step, a solution containing 0.15 M monomer, 0.14 M [O-(7-azabenzotriaol-1-yl)-1,1,3,3- tetramethyluronium hexafluorophosphate (HATU), 0.15 M DIEA and 0.225 2,6-lutidine in DMF was prepared by sequential combination of the reagents. This solution was then added to the synthesis support and allowed to react for 2 hours. The solution was then flushed through the vessel with a stream of argon and the support washed sequentially with DMF, DCM and DMF. The resin was then dried with a stream of argon.

In the third step, the support was the treated with 5 mL of standard commercially available PNA capping reagent (PerSeptive Biosystems, Inc., P/N GEN063102). The capping reagent was then flushed from the vessel and the support was washed sequentially with DMF and DCM. The support was then dried with a stream of argon.

For the support comprising two "E" moieties, the three step cycle was repeated (except that the Fmoc deprotection of "E" should be kept short because transmigration of the bis-(2-methoxyethyl)amidyl-diglycolic acid moiety can occur). When the support was properly derivatized, it was dried under high vacuum. Final loading of the support was determined by analysis of Fmoc loading.

This synthesis support was then packed into empty PNA synthesis column, as needed, and used to prepare PNA oligomers having C-terminal modifying moieties.

Example 9

Synthesis of PNAs

PNAs were synthesized using commercially available reagents and instrumentation obtained from PerSeptive Biosystems, Inc. PNAs possessing a C-terminal modifications were prepared by performing the synthesis using the modified synthesis support or by performing the synthesis using the Fmoc-K(dabcyl)-OH, Fmoc-"E"aeg-OH and Fmoc-"+"aeg-OH synthons directly on the automated instrument.

Example 10

General Method For N-terminal Labeling of Support Bound PNA with 5(6)carboxyfluorescein-NHS or 5(6)carboxyfluorescein The amino terminal fluorenylmethoxycarbonyl (Fmoc) group of the fully assembled PNA was removed by piperidine treatment and the synthesis support was washed and dried under vacuum. The synthesis support was then treated for 4–5 hours at 37° C. with approximately 300 μL of a solution containing 0.1M 5(6)carboxyfluorescein-NHS (Molecular Probes, P/N C-1311), 0.3M DIEA and 0.3M 2,6-lutidine. After treatment the synthesis support was washed and dried under high vacuum. The PNA oligomer was then cleaved, deprotected and purified.

Alternatively, after proper reaction with linkers and removal of the terminal amine protecting group, the resin was treated with 250 μL of a solution containing 0.5M 5(6)carboxyfluorescein, 0.5M N,N'-diisopropylcarbodiimide, 0,5M 1-hydroxy-7-azabenzotriazole (HOAt) in DMF (See: Weber et al., *Bioorganic & Medicinal Chemistry Letters*, 8: 597–600 (1998). After treatment the synthesis support was washed and dried under high vacuum. The PNA oligomer was then cleaved, deprotected and purified as described below.

Note on Fluorescein Labeling:

The fluorescein labeled PNAs described herein were prepared using different procedures. The different procedures have evolved to optimize fluorescein labeling conditions. At this time we prefer to use the procedure of Weber et al. for most fluorescein labeling operations.

Example 11

Cy3 Labeling of PNAs

The purified amine containing PNA is dissolved in 1/1 DMF/water at a concentration of 0.05 OD/μL to prepare a stock PNA solution. From the stock, approximately 30 nmole of PNA is added to a tube. To this tube is then added 125 μL 0.1 M HEPES (pH 8.5), and enough 1/1 DMF/water to bring the total volume to 250 μL. This solution is thoroughly mixed. To a prepackaged tube of Cy3 dye (Amersham), is added the entire 250 μL solution prepared as described above. The tube is well mixed and then allowed to react for 1 hour at ambient temperature.

After reaction, the solvent is removed by evaporation in a speed-vac. The pellet is then dissolved in 400 μL of a solution containing 3:1 1% aqueous TFA/ACN. The solution is then preferably transferred to a 5000 MW Ultrafree (Millipore P/N UFC3LCC25) or 3000 MW Amicon (Microcon microconcentrator P/N 42404) spin cartridge to removed excess dye. The recovered product was then repurified by HPLC.

PNA Oligomers Prepared:

TABLE 1

| Probe No. | Sequence |
|---|---|
| | N-terminally Labeled Only |
| 1 | Flu-O-ACGCCA-CCA-GCT-CCA-NH₂ |
| | C-terminally Labeled Only |
| 2 | Ac-TGG-AG-OO-G-GCG-T-K(dabcyl)-NH₂ |
| 3 | Ac-TGG-AG-OOO-G-GCG-T-K(dabcyl)-NH₂ |
| 4 | Ac-TGG-AG-O"+"O-G-GCG-T-K(dabcyl)-NH₂ |
| 5 | Ac-"E"-TGG-TGG-CGT-K(dabcyl)-NH₂ |
| 6 | Ac-"+"OO-TGA-TTG-CGA-ATG-A-K(dabcyl)-NH₂ |
| 7 | Ac-"+"-OO-ATT-GCG-AAT-GA-K(dabcyl)-NH₂ |
| 8 | Ac-"+"-OO-TGC-GAA-TGA-K(dabcyl)-NH₂ |
| | Probes Labeled On Both The C- and N- Termini |
| 9 | Flu-O-ACG-CCA-CCA-GCT-CCA-K(dabcyl)-NH₂ |
| 10 | Cy3-O-ACG-CCA-CCA-GCT-CCA-K(Flu)-NH₂ |
| 11 | Cy3-O-TTG-AG-OOO-GGC-GT-K(dabcyl)-NH₂ |
| 12 | Cy3-O-TTG-AG-O"+"-O-GGC-GT-K(dabcyl)-NH₂ |

All PNA sequences are written from the amine (N-) terminus to the carboxyl (C-) terminus. Abbreviations are: Ac = acetyl, "E" and "+" are defined above, Flu = 5(6)-carboxyfluorescein, dabcyl = 4-((4-(dimethylamino)phenyl)azo)benzoic acid, O = 8-amino-3,6-dioxaoctanoic acid, K = the amino acid L-Lysine and Cy3 is the Cy3 dye (Amersham).

Example 12

General Procedure for Cleavage, Deprotection and Purification

The synthesis support (Fmoc-PAL-PEG/PS; P/N GEN913384) was removed from the synthesis cartridge, transferred to a Ultrafree spin cartridge (Millipore Corp., P/N SE3P230J3) and treated with a solution of TFA/m-cresol (either of 7/3 or 8/2 (preferred)) for 1–3 hours. The solution was spun through the support bed and again the support was treated with a solution of TFA/m-cresol for 1–3 hours. The solution was again spun through the support bed. The combined eluents (TFA/m-cresol) were then precipitated by addition of approximately 1 mL of diethyl ether. The precipitate was pelletized by centrifugation. The pellet was then resuspended in ethyl ether and pelletized two additional times. The dried pellet was then resuspended in 20% aqueous acetonitrile (ACN) containing 0.1% TFA (additional ACN was added as necessary to dissolve the pellet). The product was analyzed and purified using reversed phase chromatographic methods.

Note: Several PNAs were prepared using new product Fmoc-XAL-PEG/PS synthesis support (P/N GEN 913394) available from PerSeptive Biosystems, Inc. This support has the advantage that the PNA can be removed more rapidly and under more mildly acid conditions. For PNAs prepared with Fmoc-XAL-PEG/PS the support was treated as described above except that a solution of TFA/m-cresol 9/1 was generally used for a period of 10–15 minutes (2x).

Example 13

Analysis of Thermal Profiles
General Experimental Procedure:

Fluorescent measurements were taken using a RF-5000 spectrofluorophotometer (Shimadzu) fitted with a water jacketed cell holder (P/N 206–15439, Shimadzu) using a 1.6 mL, 10 mm path length cuvet (Stana Cells, Inc.). Cuvet temperature was modulated using a circulating water bath (Neslab). The temperature of the cuvet contents was monitored directly using a thermocouple probe (Bamant; model No. 600–0000) which was inserted below liquid level by passing the probe tip through the cap on the cuvet (custom manufacture).

Stock solution of purified PNA probe was prepared by dissolving the PNA in 50% aqueous N,N'-dimethylformamide (DMF). From each PNA stock was prepared a solution of Dabcyl-PNA and Flu-PNA, each at a concentration of 10 pmol in 1.6 mL of Hyb. Buffer (50 mM Tris HCl pH 8.3 and 100 mM NaCl). To form a PNA/PNA duplex the tube was heated for 12 minutes at 95° C. in a heating block. Before recording fluorescent measurement the solution was allowed to stand, after heating, at ambient temperature for 2 hours.

Figure 8A:
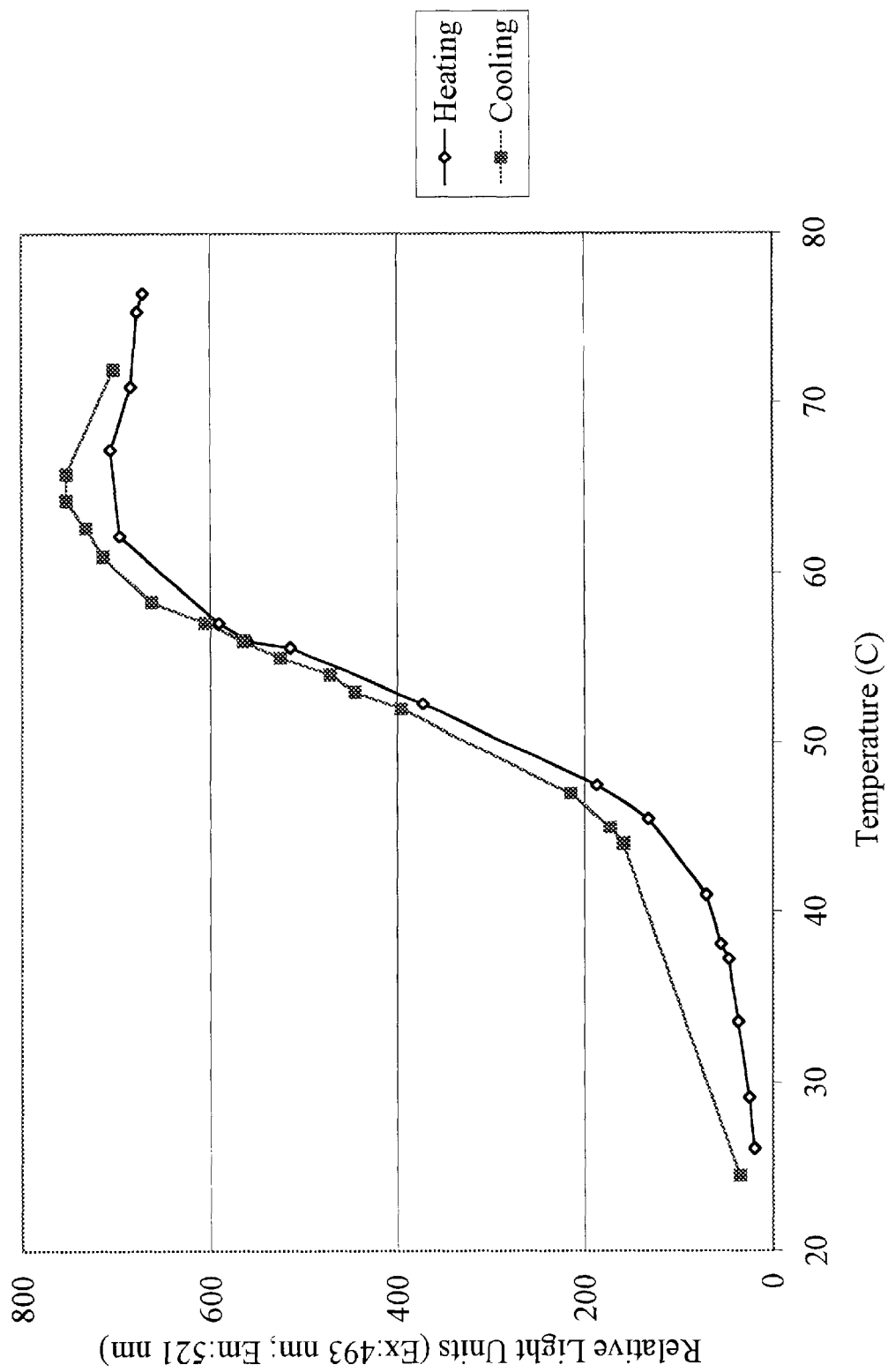
FIG. 8A is a graphical illustration of fluorescence vs. temperature thermal profile for a Detection Complex assembled from two PNAs.

Samples were exited at 493 nm and the fluorescence measured at 521 nm. Data points were collected at numerous temperatures as the cuvet was heated and then again measured as the cuvet was allowed to cool. Generally, the bath temperature was sequentially increased by 5° C. and then allowed to equilibrate before each data point was recorded. Similarly, to generate the cooling profile, the bath temperature was sequentially decreased by 5° C. and then allowed to equilibrate before each data point was recorded.
Data Discussion:
General:

The Detection Complexes were formed by mixing two PNA probes. When formed, the fluorescent intensity of a solution containing the Detection Complex is relatively low because the fluorophore and quencher, although covalently attached to two individual polymers, are, by design of their respective nucleobase sequences, brought in such close proximity such that most or substantially all of the fluorescent signal is quenched by the interaction of the fluorophore and quenching moiety. Once formed, the Detection Complex is heated to thermally denature the Detection Complex and thereby determine the stability of the Detection Complex. Thermal denaturation of the Detection Complex results in the generation of a more intense fluorescent signal because once the individual polymers are physically separated, the fluorophore and quenching moieties are no longer so closely associated that the quenching moiety is able to quench most or substantially all of the fluorescent signal. Thus, the intensity of the fluorescent signal is directly related to the percent of Detection Complex present in the sample. Although fluorescent intensity is used instead of ultraviolet absorbance (typically at 260 nm), the data should exhibit a sigmoidal profile similar to that observed when determining the thermal melting point (Tm) of a nucleic acid duplex using $A_2$, analysis. In theory both methods should produce the same Tm. Moreover, the process should be reversible such that the fluorescent intensity should decrease with decreasing temperature as the Detection Complex reforms (reanneals).
Data:

a. With reference to FIG. 8A, the results of a thermal profile are graphically illustrated for the Detection Complex which was formed by mixing two PNA probes in a ratio of 1 to 1 (10 pmol Ac-TGG-AG-OO-GG-CGT-K(dabcyl)-$NH_2$ (annealing polymer: Probe No. 2 of Table 1) mixed with 10 pmol Flu-O-ACG-CCA-CCA-GCT-CCA-$NH_2$ (probing polymer: Probe No. 1 of Table 1)) in 1.6 mL of hybridization buffer. By design, the Detection Complex comprises two 5 bp stem regions at each end of the complex with a 5 bp bulge in the center of the polymer wherein there are no complementary nucleobases (see FIG. 1B). Thus, the linkers which link the two 5 bp segments need only be long enough to provide for suitable interaction of the nucleobases at the ends of the respective polymers so that the Detection Complex can form.

Figure 9:
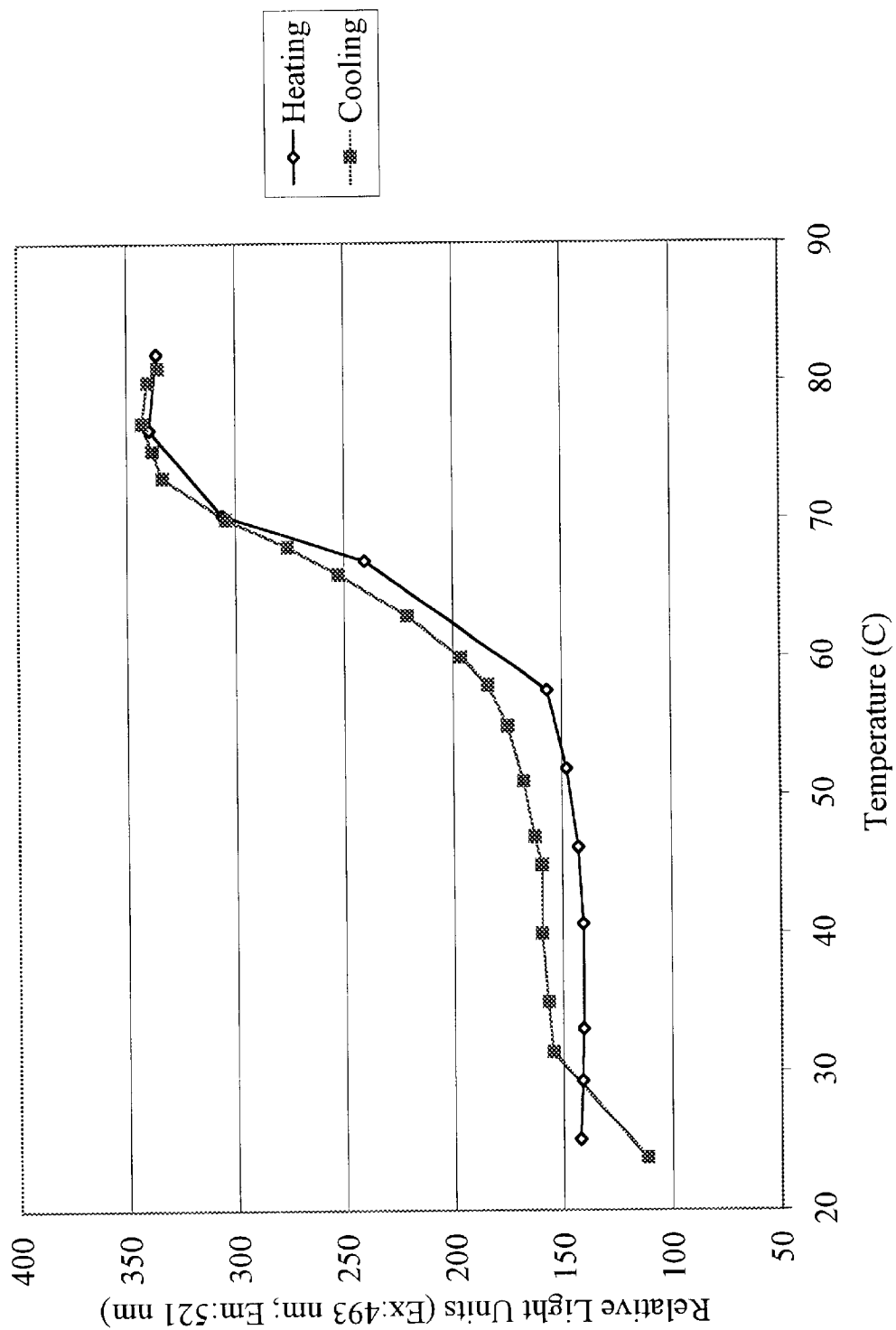
FIG. 9 is a graphical illustration of fluorescence vs. temperature thermal profile for a Detection Complex assembled from two PNAs.

In this example, the Detection Complex exhibits a thermal profile consistent with a melting and reannealing as indicated by an increase in fluorescence intensity upon heating (melting) and a correlating decrease in fluorescence intensity upon cooling (reannealing). The data indicates that the melting point (Tm) of the Detection Complex is approximately 55° C.

b. With reference to FIG. 9, the results of a thermal profile are graphically illustrated for a Detection Complex which was formed by mixing two PNA probes in a ratio of 1 to 1 (10 pmol Ac-"E"-TGG-TGG-CGT-K(dabcyl)-$NH_2$ (annealing polymer: Probe No. 5 of Table 1) was mixed with 10 pmol Flu-O-ACG-CCA-CCA-GCT-CCA-$NH_2$ (probing polymer: Probe No. 1 of Table 1)) in 1.6 mL of hybridization buffer. By design, this Detection Complex comprises two PNAs of differing lengths. Because the shorter annealing polymer is complementary to a portion of the terminus of the probing polymer, the Detection Complex comprises a 9 bp duplex with a 6 bp tailing sequence (See: FIG. 1A).

Again, the Detection Complex exhibits a thermal profile consistent with a melting and reannealing of the polymer as indicated by an increase in fluorescence intensity upon heating (melting) and a correlating decrease in fluorescence intensity upon cooling (reannealing). The data indicates that the melting point of the Detection Complex is approximately 67° C.

Example 14

Analysis of Hybridization Assay Data
General Experimental Procedures:

For this study, a biotin labeled wt k-ras DNA oligonucleotide suitable as target sequence was synthesized. The DNA is illustrated 5' to 3'.

Seq. ID. No. 1
WT K-ras Biotin-GTG-GTA-GTT-GGA-GCT-GGT-GGC-GTA

All hybridization assay data was collected using a Wallac multilabel counter equipped with a F485 CW-lamp filter and a F535 Emission filter. The NUNC MaxiSorp, breakapart microtitre plate was used as the reaction vessel. Each microtitre plate was prewashed with Hyb. Buffer at room temperature for 15 minutes before the reaction components were added. Total reaction volume was 100 μL in Hyb. Buffer.

Stock solution of purified WT K-ras DNA (Genosys) was prepared by dissolving the purified DNA in TE (10 mM Tris-HCl pH 8.0; 0.1 mM EDTA, Sigma Chemical). From this DNA Stock was prepared a solution of WT K-ras DNA at a concentration of 100 pmol/μL by serial dilution of the DNA Stock with Hyb. Buffer.

Figure 8B:
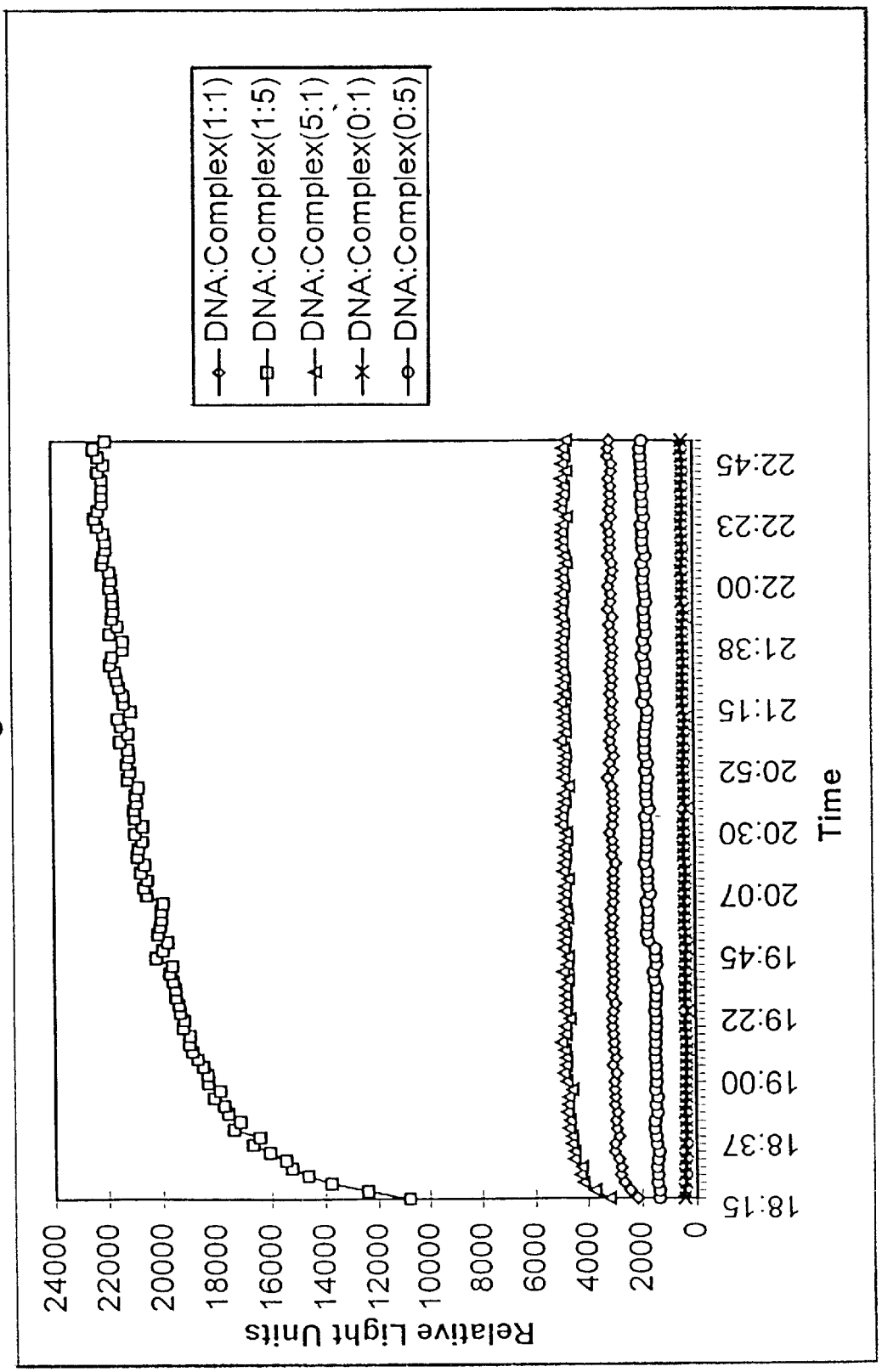
FIG. 8B is a graphical illustration of hybridization assay data for a Detection Complex assembled from two PNAs.

Each measurement contained 100 μL total volume with relative quantities of WT K-ras DNA and Detection Complex as illustrated in FIG. 8B. Each reaction sample was prepared by combining the required amount of Detection Complex (2 μL for 1Eq. and 10 μL for 5 Eq.), WT K-ras DNA as the target (1 μL for 1Eq. and 5 μL for 5 Eq.) and Hybridization Buffer as needed to prepare 100 μL of sample.

Samples were mixed and then fluorescence intensity monitored as a function of time using the Wallac VICTOR instrument. The data collected was plotted to generate the figures.

Data Discussion:
  General:
  The Detection Complex is formed by mixing the annealing and probing polymers. When formed, the fluorescent intensity of a solution containing the Detection Complex is relatively low. Once formed, the Detection Complex is contacted with target nucleic acid under conditions suitable for hybridization of the probing polymer to the target nucleic acid (TNA). Hybridization of the probing polymer to the target nucleic acid will generally cause the Detection Complex to dissociate provided the stability of the complex between the target sequence and the probing segment is more thermodynamically favored as compared with the stability of the Detection Complex. Detection Complex dissociation results in the generation of a more intense fluorescent signal because the fluorophore and quenching moiety will no longer be so closely associated that the quenching moiety is able to quench most or substantially all of the fluorescent signal. Thus, hybridization is detected by the increase in fluorescence intensity as compared with samples wherein the target nucleic acid is not present.

Data:
  With reference to FIG. 8B the results of a hybridization assay are graphically illustrated. For this example, the Detection Complex is generated from a 1:1 mixture of PNA polymers (Ac-TGG-AG-OO-GG-CGT-K(dabcyl)-NH$_2$ (Probe No. 2 of Table 1) and Flu-O-ACG-CCA-CCA-GCT-CCA-NH$_2$ (Probe No. 1 of Table 1)). In this example, mixtures of 1:5, 5:1 and 1:1 target nucleic acid/Detection Complex, respectively, have been analyzed. The controls are 0:5 and 0:1 target nucleic acid/Detection Complex, respectively. The data demonstrates that, as compared with the control samples (which do not substantially change in fluorescent intensity over time), the fluorescent intensity of the samples containing target nucleic acid, increase with time and are substantially greater than the fluorescence observed in the controls. Thus, the data demonstrates the Detection Complexes of this invention can be used as a probe instead of a primer.

The analysis performed in Examples 13 and 14 can be applied to other PNAs listed in Table 1 to thereby generate similar results. The results demonstrate that stable Detection Complexes form/dissociate in a predictable manner. Furthermore, these Detection Complexes can be used as a probes to detect the presence, absence or quantity of a target sequence and/or target molecule in a sample.

Example 15

Use of Detection Complexes as Primers in PCR

Overview

The assays described in this Example were shown to yield predicable fluorescent signal generation from initially dark (non-fluorescent) PCR reactions. Detectable fluorescent signal generated during the assay was directly proportional to the quantity of nucleic acid produced by the amplification reaction.

Experiment A

This experiment was used to demonstrate that the Detection Complex formed by hybridization of the PNA Quencher and each of the 3' and 5' DNA primers was capable of reversible melting and reannealing in response to thermal changes in environment in a manner which generated detectable fluorescent signal when the Detection Complex was dissociated.

Experiment B

For this experiment, the template concentration was fixed so that fluorescence intensity generated by the amplification reaction could be correlated with the number of amplification cycles. PCR reactions were performed for 17, 20, 23, 26, 29, 32, and 35 amplification cycles with 1 fmole of template per reaction. The fluorescent signal of the PCR reaction was then quantitated and the presence and length of the nucleic acid amplification products was confirmed by separation of the sample components using polyacrylamide gel electrophoresis. A negative control (no template) was also performed (35 cycles). The fluorescence quantitation data correlated well with the number of cycles of PCR. The quantitated fluorescent signal also correlated well with the amount of fluorescent starting materials and products which were observed in the polyacrylamide gel analysis.

Experiment C

For this experiment, the template concentration was varied so that fluorescence intensity generated by the amplification reaction occurring in a fixed number of cycles could be correlated with the quantity of template in each PCR reaction. Quantitated fluorescent signal generated by the assay was found to be very regular over a 7 log range of target (1 fmole to 1 zmole). The experiment demonstrates the viability of using the method to generate a standard curve which can then be used to determine the quantity of target sequence or target molecule in an unknown sample by comparing assay results with the standard curve.

Materials and Methods

Probes, Primers and Templates:
  PNA Quencher:
  This PNA Quencher was designed to be complementary to the 13 nucleobases of the 5' terminus of both the 3' and 5' DNA Primers. Using this preferred embodiment, only one PNA Quencher was required to quench the fluorescence of both of the 3' and 5' DNA Primers. Shorter versions (11 and 9 nucleobases in length) of the PNA Quencher (See: Table 1, Nos. 7 and 8) were also found to quench fluorescent signal of the Detection Complex (data not shown). However, the longest PNA Quencher was chosen for these experiments since it formed the most stable Detection Complex.

```
PNA Quencher (Table 1, No. 6) C Dabcyl(K)-AGTAAGCGTTAGT-OO-+-Ac N
C = Carboxy terminus,
N = Amine terminus, "Ac", "K""+""Dabcyl" and "O" are previously
defined.
```

DNA Primers:

The 5' DNA Primer and 3' DNA Primer comprise both a priming sequence (shown in underlined text), which is complementary to the priming site on the target nucleic acid of interest, and a common complex forming segment (CFS) to which the PNA Quencher hybridizes (shown in Bold text). The common complex forming segment comprises the interacting groups which hybridize to the PNA Quencher.

```
                <-common CFS-><-unique priming sequence->
5' Primer 5' Flu-TCATTCGCAATCAATGACTGAATATAAACTTGT-OH   3'  SEQ. ID No. 2

3' Primer 5' Flu-TCATTCGCAATCACTCTATTGTTGGATCATATT-OH   3'  SEQ. ID No. 3
```

DNA primers were prepared using commercially available reagents and instrumentation and were purified using methodologies known to those of skill in the art. The Flu=5(6)-carboxyfluorescein label is attached to the primer through an aminohexanol linkage.

dsDNA K-ras plasmid Template (only the amplified region is shown with the priming sites underlined)

```
         <- 3'priming site ->
3'  ...GAGATAACAACCTAGTATAAGCAGGTGTTTTACTAAGACTTAATCGACTTAGCAGTTCC..

5'  ...CTCTATTGTTGGATCATATTCGTCCACAAAATGATTCTGAATTAGCTGTATCGTCAAGG..

..GTGAGAACGGATGCGGTGGTCGAGGTTGATGGTGTTCAAATATAAGTCAGTA... 5' SEQ ID No. 4

..CACTCTTGCCTACGCCACCAGCTCCAACTACCACAAGTTTATATTCAGTCAT... 3' SEQ ID No. 5
                                       <- 5'priming site ->
```

PNA Quencher was diluted in water and stored at 4° C. Primers and DNA templates were diluted in TE (10 mM TRIS pH 8.0, 1 mM EDTA) and stored at 4° C.

PCR Assays:

PCR reactions were performed in the Perkin-Elmer 2400 thermocycler in individual mini-eppendorf tubes without oil or wax. The PCR protocol involved a 5 second warm up to 94° C. (1st round only), followed by denaturing at 94° C. for 5 seconds, annealing at 55° C. for 1 minute, and extension at 74° C. for 1 minute. The denaturation-annealing-extension cycle was repeated for 35 cycles in Experiment B, and for 40 cycles in Experiment C. In Experiment C only, an additional 7 minute extension step at 74° C. was done after cycle 40.

Each PCR reaction contained 2 pmoles of the 5' and 3' DNA Primers, 2 mM $MgCl_2$, 125 µM ATP, 125 µM CTP, 125 µM GTP, 125 µM TTP, 1 unit AmpliTaq DNA polymerase, 50 mM KCl, and 10 mM TRIS, pH 8.3. Experiment B used 12 pmole of PNA Quencher, per reaction, thereby generating a 3:1 ratio of PNA Quencher to DNA primer. Experiment C used 16 pmole of PNA Quencher per reaction, thereby generating a 4:1 ratio of PNA Quencher to DNA primer.

To allow complete hybridization between the DNA primers and PNA Quenchers, the components of the PCR reactions were first mixed in round bottom microtiter plates and incubated with by gentle shaking at room temperature for about 5 minutes. The plate was then placed into the Wallac multilabel counter, and fluorescence was measured for 1 second per well. Fluorescence was measured using an excitation filter at 485 nm, and an emission filter at 535 nm. After the prereaction fluorescence was determined ("RLU Before" measurement), the samples were transferred to mini-eppendorf tubes and PCR was performed.

After PCR, samples were transferred to a new microtiter plate for the "RLU After" fluorescence measurement. After determining the post PCR fluorescence of each reaction, 2 µL of a 5× loading dye was added to each sample, and the entire reaction sample was then separated using polyacrylamide gel electrophoresis (Conditions: 10–20% polyacrylamide gradient gel and electrophoresed at 100 V, 40 mA for approximately 1.5 hours). Prior to ethidium bromide staining, photographic images of the fluorescent products contained in the gels were obtained using a transilluminator (UV light 302 nm; See for example, FIGS. 12A and 14A). Gels were stained in a solution of 500 µM ethidium bromide while shaking gently at ambient temperature for 2 minutes, then destained in water for approximately 15 minutes, and rephotographed while exposed to UV light from a transilluminator (FIGS. 12B and 14B). Gels were then placed in High pH Buffer for 2 minutes to denature intact PNA Quencher-DNA Primer complexes, after which, they were photographed a third time while exposed to UV light from a transilluminator (FIGS. 12C and 14C).

Reagents:

The DNA template was PCR amplified from human DNA (using a kit purchased from Clontech) and cloned into the pCR2.1 plasmid (Invitrogen). Clones were screened by restriction fragment analysis and then sequenced. Large preparations of the plasmid were generated and quantitated using standard techniques. The cloned sequence flanks a region in the human K-ras gene where point mutations are known to occur in certain disease states. The K-ras region amplified is 111 bp in length, but when amplified using both of the DNA primers described above, a 137 bp amplicon is prepared due to the incorporation of the two 13 bp complex forming segments present in the primers (111+13+13=137).

PCR reagents including 10× buffer, magnesium chloride solution, AmpliTaq DNA polymerase, and nucleotide triphosphates were obtained from Perkin-Elmer.

10%–20% Gradient Pre-Cast Mini-Gels, 10× Running Buffer, and 5× Sample Dye were obtained from ESA, Inc., Chelnsford Mass.

High pH Buffer: 0.4M NaOH, 0.6M NaCl, pH~13.
TE: 10 mM TRIS, pH 8.0, 1 mM EDTA.
PhiX174/Hae III was purchased from New England BioLabs. It is supplied in TE at 1 µg/µL.

Results

General:

In the following results and discussion, all of the original data points were included in the derived numbers. Background was subtracted from all derived data.

Experiment A:

Assay Description:

Fluorescent measurements were taken using a RF-5000 spectrofluorophotometer (Shimadzu) fitted with a water jacketed cell holder (P/N 206–15439, Shimadzu) using a 1.6 mL, 10 mm path length cuvet (Stana Cells, Inc.). Cuvet temperature was regulated using a circulating bath (Neslab). The temperature of the cuvet contents was monitored directly using a thermocouple probe (Bamart; model No. 600–0000) inserted below liquid level.

Stock solution of purified PNA Quencher was prepared by dissolving the PNA in 50% aqueous N,N'-dimethylformamide (DMF). Stock solutions of purified DNA primers were prepared by dissolving the DNAs in 10 mM Tris pH 8.3, 1 mM EDTA (TE). For each hybrid, 20 pmole PNA Quencher and 10 pmole of either of the 3' or 5' DNA Primer were mixed and then diluted to 1.6 mL in Hybridization Buffer (50 mM Tris, pH 8.3, 100 mM NaCl). The Detection Complex was allowed to form for ten minutes at room temperature (21° C.) before data for the thermal profile was collected.

Samples were excited at 495 nm and fluorescence was measured at 520 nm. Data points were collected at numerous temperatures as the cuvet was heated, and then measured again as the cuvet was cooled.

Discussion:

The thermal profiles generated from fluorescence vs. temperature data for each of the 3' and 5' DNA Primers hybridized to the PNA Quencher are shown as FIGS. 10A and 10B. Both FIGS. 10A and 10B exhibit sigmoidal heating and cooling curves of the type expected for the melting and reannealing of a PNA/nucleic acid hybrid. For both heating curves, the inflection point of the curve is approximately 60° C. (the approximate Tm value), with the curve leveling to a lower and upper plateau at approximately 50 and 70° C., respectively. Though the cooling curve for the 5' DNA primer exhibits a slight histerisis, the data demonstrates that the complex readily dissociates and reforms in response to thermal changes in environment. Furthermore, there is a tremendous fold increase in fluorescence resulting from the dissociation of the Detection Complex.

Experiment B:

Assay Description:

Before any reagents were added to the microtiter plate, a background fluorescence for each well of the microtitre plate was recorded. A master mix was made which contained all of the reagents for the PCR reactions, with the exception of template, DNA primers, and PNA Quencher. Six microliters of this master mix was added to each of eight reaction wells in the microtiter plate. To each well was then added 1 µL of each 3' and 5' DNA Primer (2 pmole/µL), 1.5 µL of PNA Quencher (8 pmole/µL), and 1 µL of template (1 fmole/µL), for a total volume of 10.5 µL. For the negative control, 1 µL of TE was added instead of template. Once all the reagents for each reaction were combined, the RLU Before measurement was recorded and the samples transferred to microtube for performing the PCR reactions as previously described. PCR was paused momentarily after the 1 minute 74° C. extension steps in cycles 17, 20, 23, 26, 29, and 32 to withdraw a sample for analysis. These samples were placed in a 4° C. refrigerator after being removed from the thermocycler. Each cycle of the protocol lasted approximately 1 minute and 15 seconds, so the quantity of time between the withdrawal of the sample at cycle 17, and the withdrawal of the sample at cycle 35 was almost exactly equal to 60 minutes. The cycle 35 sample was cooled in the refrigerator for 5 minutes after all PCR reactions were complete. All samples were centrifuged briefly at room temperature before being transferred to a clean microtiter plate for the post-PCR fluorescent measurement. By the time the post PCR fluorescent measurement was made the samples had been at room temperature for approximately 10 minutes.

TABLE 2

| | A | B | C | D | E |
|---|---|---|---|---|---|
| | Sample | Rounds PCR | RLU Before | RLU After | S/N Ratio |
| 1 | | | | | |
| 2 | Negative | 35 | 2412 | 1804 | 0.7 |
| 3 | Positive | 17 | 2422 | 4858 | 2.0 |
| 4 | Positive | 20 | 2794 | 10589 | 3.8 |
| 5 | Positive | 23 | 2568 | 14249 | 5.5 |
| 6 | Positive | 26 | 2494 | 15510 | 6.2 |
| 7 | Positive | 29 | 2820 | 20833 | 7.4 |
| 8 | Positive | 32 | 2934 | 25192 | 8.6 |
| 9 | Positive | 35 | 2754 | 28007 | 10.2 |

Figure 11:
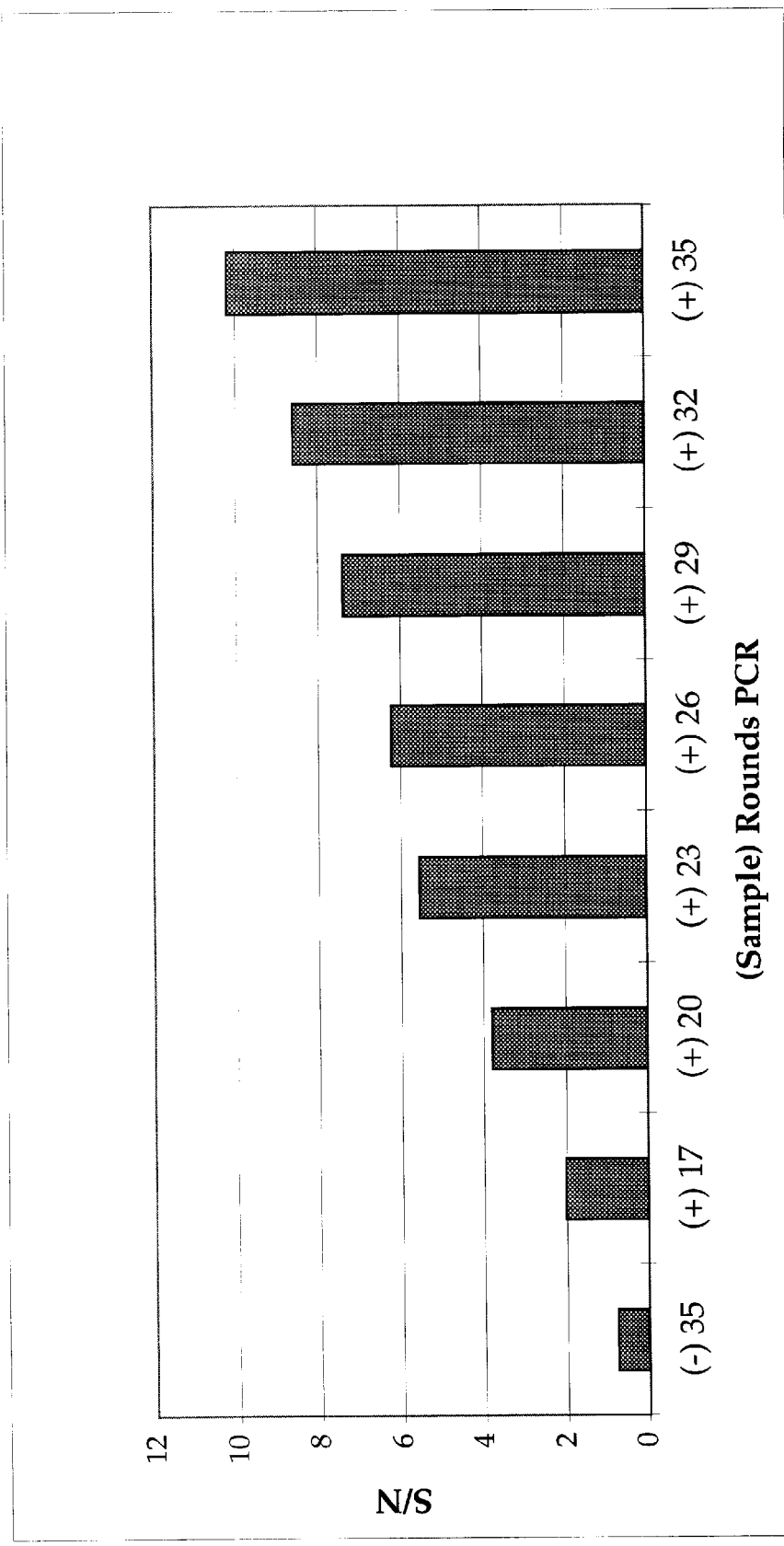
FIG. 11 is a graphical illustration of tabular data obtained for a PCR reaction.
Figure 12:
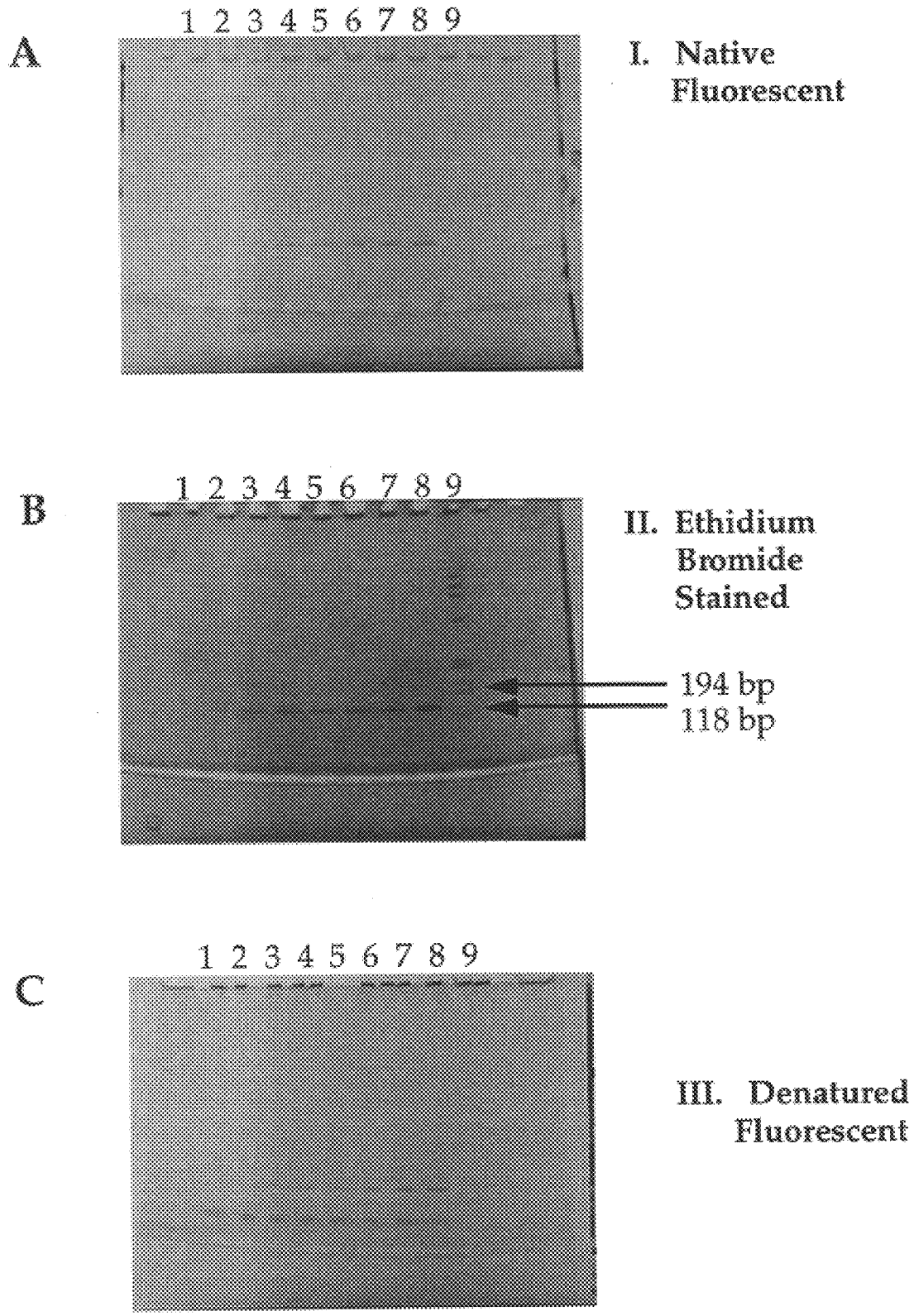
FIGS. 12A–12C are electronic composite negative images of photographs taken of a polyacrylamide gel used to analyze PCR reaction products for fluorescence.

Discussion:

Data obtained for this Experiment B is presented in Table 2 and FIGS. 11 and 12. With reference to Table 2, both experimental and derived tabular data is presented. Sample type (positive or negative) is displayed in column A. The number of PCR cycles is listed in column B. The fluorescence measurement taken prior to PCR is displayed in column C ("RLU Before"). The fluorescence measurement after PCR is displayed in column D ("RLU After") and the calculated signal to noise ratio is displayed in column E. Signal to noise is calculated by dividing the "RLU After" value by the "RLU Before" value. FIG. 11 is a graphical representation of the data presented in Columns B & E of Table 2. FIG. 12 comprises three computer generated composite negative images of three photographs (A, B & C) taken of the fluorescence of a gel positioned on a transilluminator. All three photographs are of the same gel after performing each of the manipulations described in Materials and Methods (above). More specifically, in Photograph A, all native fluorescence of the separated sample components are visible. In Photograph B, all components stainable by ethidium bromide are visible. In Photograph C all sample components which are fluorescent under the denaturing conditions are visible.

As previously defined, the "RLU Before" value is the measurement of fluorescence of the reaction prior to PCR. With reference to Table 2, column C, "RLU Before" values are very low, and quite similar for all samples. This indicates that the fluorescence quenching was quite efficient for the complex formed between the PNA Quencher and the 3' and 5' DNA Primers.

PCR amplification resulted in dissociation of the Detection Complex to thereby generate detectable fluorescent signal as can be deduced by comparison of the "RLU After" value (column D) with the "RLU Before" values (Column C) for all samples which contained template. This data is consistent with the incorporation of fluorescent 3' and 5' PNA Primers into dsDNA. Signal to noise ratios (S/N, column E) greater than 1 indicate an increase in fluorescence after the PCR reaction has been completed.

With reference to columns B and E of Table 2, there is a clear correlation between the number of cycles of PCR and the S/N ratio for all samples containing 1 fmole of template. The S/N ratio increases steadily from a value of 2.0 at cycle 17 (row 3, column E) to a value of 10.2 at cycle 35 (row 9, column E) This steady increase is apparent from the graphical representation of the data (FIG. 11). The negative control, shows no increase in fluorescence resulting from 35 cycles of PCR. Loss of sample during transfers between the microtiter plates and the mini-eppendorf tubes was observed (~1–2 µL). This loss of sample will at least partially account for S/N ratio of less than 1.0 for the control.

The photographic images presented in FIG. 12 yield conclusive proof that the observed increases in fluorescence discussed with reference to Table 2 and FIG. 11, can be correlated with the production of dsDNA by the PCR reaction.

The photographic images are displayed with the sample wells at the top. Lane number 1 contains the negative control, and lanes 2 through 8 are sequentially the reactions for 17, 20, 23, 26, 29, 32 and 35 cycles of PCR. Lane 9 is the size marker PhiX174/Hae III.

With reference to FIG. 12, Photograph A, fluorescence was observed immediately after the gel was run. In the photograph, fluorescent dsDNA was visible in lanes 2 through 8, just below the midpoint of the image. The fluorescent intensity increased from left to right as would be expected for increasing quantities of ds DNA produced by a greater number of cycles of PCR. No fluorescence is observed in the negative control (Lane 1) or from the PCR Detection Complexes.

With reference to FIG. 12, Photograph B, fluorescence is observed after the gel was stained with ethidium bromide. There is very little difference between the images in Photograph A and B except that in Photograph B the dsDNA size marker PhiX174/Hae III is now visible in lane 9. The position of the amplified PCR fragment of 137 bp is consistent with its position between the 198 bp and 118 bp fragment (marked with the two black arrows).

With reference to FIG. 12, Photograph C, fluorescence is observed after the ethidium bromide treated gel has been subsequently treated with a solution of sodium hydroxide to denature the dsDNA as well as the Primer/PNA Quencher complexes. The Figure reveals the presence of unincorporated fluorescent primers, located between the dsDNA band and the dye front (the dye front is not visible in the photographic image). The fluorescent intensity of the primer bands are inversely proportional to the intensity of the dsDNA amplimers. Specifically, the primer band is very prominent in lane 1, where no dsDNA was formed during 35 rounds of PCR. However, with each successive of lanes 2–8, the fluorescence intensity decreases thereby demonstrating that the fluorescent primers were incorporated into the dsDNA amplicons (compare with intensity of the higher running band).

These primers were not visible in Photographs A and B because they were associated with PNA Quencher (Photograph A). Under denaturing conditions, the primers fluoresce because they are dissociated from the PNA Quenchers. Interestingly, the dsDNA size marker disappears in Photograph C presumably because the ethidium bromide is non fluorescent under the denaturing conditions.

Summary:

PCR reactions were run for 17, 20, 23, 26, 29, 32, and 35 cycles with 1 fmole of input template. A negative control, without template, was run for 35 rounds of PCR. A direct relationship was established between the number of cycles of PCR and the intensity of fluorescent signal generated in template containing reactions. Signal to noise ratios increased from 2.0 at cycle 17 to 10.2 at cycle 35 while the negative control generated no detectable fluorescent signal. The fluorescent signal measured in a fluorometer correlated well with the amount of fluorescent dsDNA seen on a polyacrylamide gel and the quantity of fluorescent primer consumed in each of the PCR reactions. Taken as a whole, this experiment conclusively demonstrates that the fluorescent signal increased in each of the PCR reactions in a manner consistent with the total number of PCR cycles and hence the quantity of dsDNA amplicon generated by the PCR process.

Experiment C:

Assay Description:

Experiment C was designed to monitor the generation of fluorescent signal from PCR reactions when template levels are varied between 1.0 E-15 mole (1 femtomole) to 1.0 E-21 mole (1 zeptomole).

Before any reagents were added to the microtiter plate, a background fluorescence for each well of the microtitre plate was recorded. A master mix was made which contained all of the reagents for the PCR reactions, with the exception of template, DNA primers, and PNA Quencher. Six microliters of this master mix was added to each of eight reaction wells in the microtiter plate. To each well was then added 1 µL of each DNA primer (2 pmole/µL), 2.0 µL of PNA Quencher (8 pmole/µL), for a total volume of 10.0 µL. Finally, 1 µL aliquots of a previously prepared dilution series of plasmid template were added. The dilution series consisted of seven 1 log steps from 1 fmole/µL to 1 zmole/µL, made in TE buffer. For the negative control, 1 µL of TE was added instead of template. Once all the reagents for each reaction were combined, the "RLU Before" measurement was recorded and the samples transferred to microtube for performing the PCR reactions as previously described.

Fluorescent intensity of each reaction was measured prior to PCR and after 40 cycles. All samples were centrifuged briefly at room temperature before being transferred to a clean microtiter plate for the "RLU After" fluorescent measurement.

Figure 13:
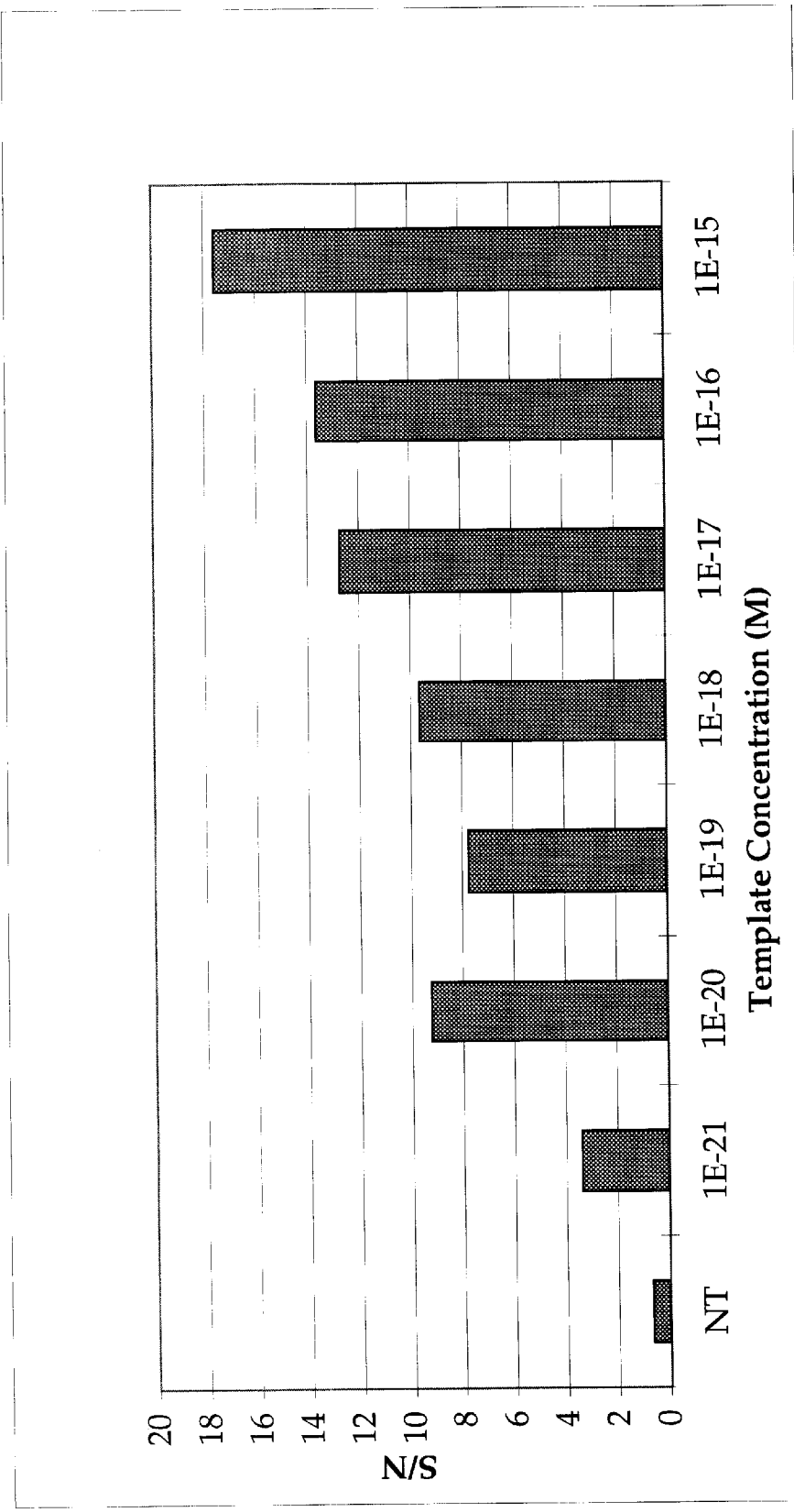
FIG. 13 is a graphical illustration of tabular data obtained for a PCR reaction.
Figure 14:
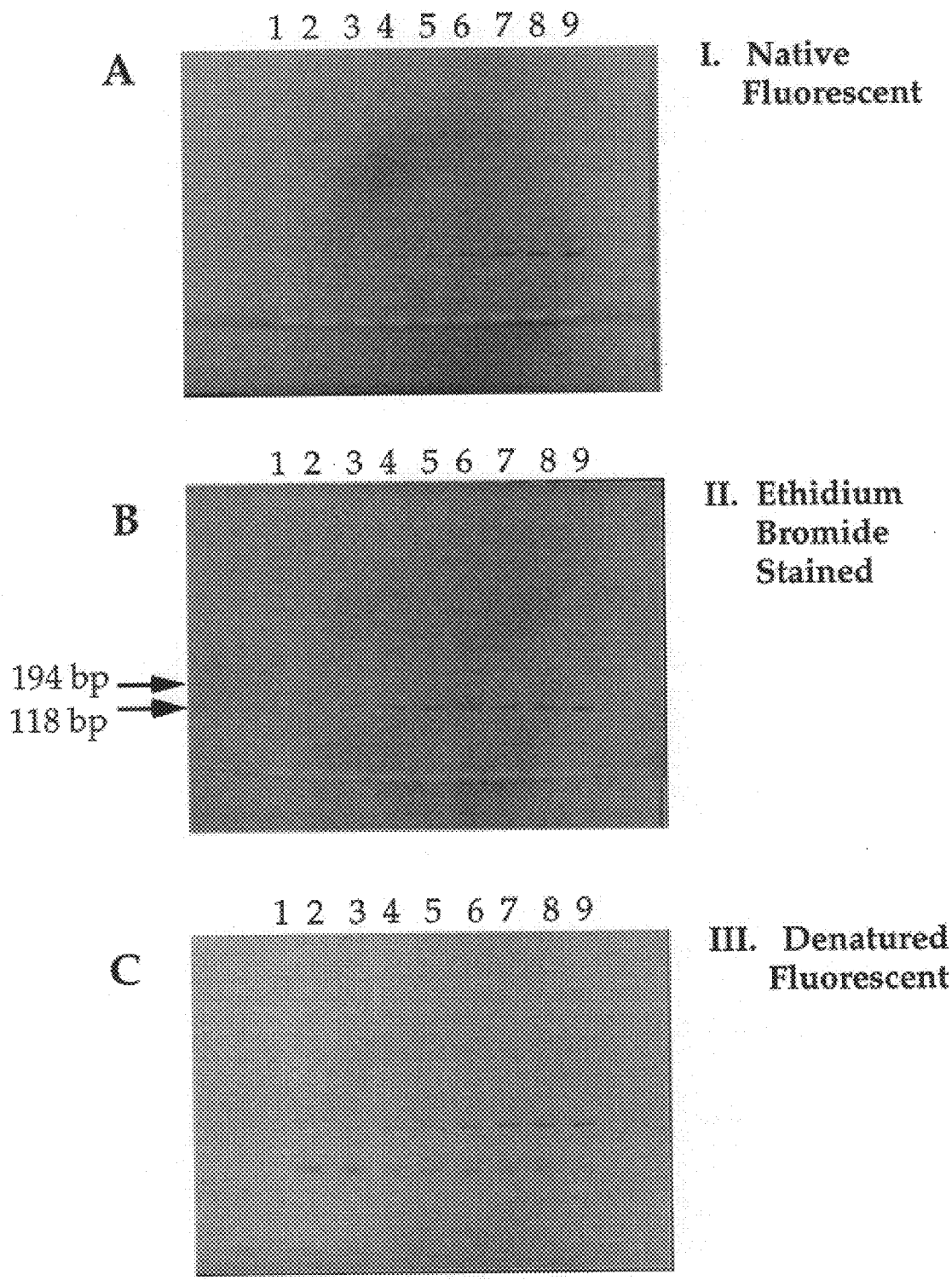
FIGS. 14A–14C are electronic composite negative images of photographs taken of a polyacrylamide gel used to analyze PCR reaction products for fluorescence.

Discussion:

Data obtained for this Experiment C is presented in Table 3 and FIGS. 13 and 14. With reference to Table 3, both experimental and derived tabular data is presented. With reference to the Table 3, the template concentration is displayed in column A. The fluorescence measured prior to PCR is listed in column B and the fluorescence measured after PCR is presented in column C. The calculated signal to noise ratio (as calculated in Experiment A) is presented in column D. The data shown in Column D is presented graphically in FIG. 13. FIG. 14 comprises three computer generated composite negative images of three photographs (A, B & C) of the same gel which has been treated as described in Materials and Methods (above). More specifically, in Photograph A, all native fluorescence of the separated sample components are visible. In Photograph B, all components stainable by ethidium bromide are visible. In Photograph C all sample components which are fluorescent under the denaturing conditions are visible.

TABLE 3

| | A | B | C | D |
| --- | --- | --- | --- | --- |
| 1 | Template (mole) | RLU Before | RLU After | S/N Ratio |
| 2 | NT | 2694 | 1750 | 0.6 |
| 3 | 1E-21 | 2158 | 7290 | 3.4 |

TABLE 3-continued

| | A | B | C | D |
|---|---|---|---|---|
| 4 | 1E-20 | 2526 | 23312 | 9.2 |
| 5 | 1E-19 | 2504 | 19393 | 7.7 |
| 6 | 1E-18 | 2638 | 25438 | 9.6 |
| 7 | 1E-17 | 2542 | 32365 | 12.7 |
| 8 | 1E-16 | 2594 | 35302 | 13.6 |
| 9 | 1E-15 | 2478 | 43563 | 17.6 |

With reference to Table 3, column B, "RLU Before" values were very low, and quite similar for all samples. This indicated that the fluorescence quenching was quite efficient for the complex formed between the PNA Quencher and the 3' and 5' DNA Primers.

With reference to columns A and D of Table 3, there is a clear correlation between the quantity of template which was added to the PCR reaction (column A) and the S/N ratio for sample after 40 cycles of PCR (column D). Specifically, the S/N ratio increased in a constant predicable manner from a value of 3.4 for 1E-21 mole of template (row 3, column D) to a value of 17.6 for 1E-15 mole of template (row 9, column D). This constant increase in fluorescent intensity is easily visualized by the data presented FIG. 13. The negative control, shows no increase in fluorescence during PCR as is indicated by the S/N value of 0.6 (row 2, column D). Loss of sample during transfers between the microtiter plates and the mini-eppendorf tubes was observed (~1–2 $\mu$L). This loss of sample will at least partially account for S/N ratio of less than 1.0 for the control.

The photographic images presented in FIG. 14 yield conclusive proof that the observed increase in fluorescence discussed with reference to Table 3 and FIG. 13, can be correlated with the production of dsDNA by the PCR reaction. Moreover, the production of dsDNA could be correlated in a predicable manner with the quantity of template added to the PCR reaction.

The photographic images are displayed with the sample wells at the top. Lane number 1 contains 1 $\mu$g of PhiX174 dsDNA digested with Hae III. Lanes 2 through 8 are sequentially the reactions containing logarithmic increases in the quantity of template DNA.

With reference to FIG. 14, Photograph A, fluorescence was observed immediately after the gel was run. In the photograph, fluorescent dsDNA was visible, in lanes 3 through 9, just below the midpoint of the image. The fluorescent intensity increased from left to right as would be expected for increasing quantities of dsDNA amplicon produced by having more template in the initial cycles of the PCR reaction. No fluorescent band is observed in the sample lacking template (negative control, Lane 2).

With reference to FIG. 14, Photograph B, fluorescence was observed after the gel was treated with ethidium bromide. There is very little difference between the images in Photograph A and B except that in Photograph B the dsDNA size marker PhiX174/Hae III is now visible in lane 1. The size marker loaded poorly due to an obstruction in the well, and as a result is difficult to see in the photograph. The two fragments closest in size to the bands seen in lanes 3–9 are the 198 bp fragment and the 118 bp fragment, which are indicated by the black arrows. The position of the amplified PCR fragment of 137 bp is consistent with its position between the 198 bp and 118 bp fragment (marked with the two black arrows).

With reference to FIG. 14, Photograph C, fluorescence is observed after the ethidium bromide treated gel has been subsequently treated with a solution of sodium hydroxide to denature the dsDNA as well as Primer/PNA Quencher complexes. The Figure reveals the presence of unincorporated fluorescent primers, located between the dsDNA band and the dye front (the dye front is not visible in the photographic image). The fluorescent intensity of the primer bands are inversely proportional to the intensity of the dsDNA amplimers. Specifically, the primer band is very prominent in lane 2, where no dsDNA was formed. However, in each of lanes 3–9, the fluorescence intensity sequentially decrease thereby demonstrating that the fluorescent primers were incorporated into the dsDNA amplimers (compare with the intensity of fluorescence for the primers in each lane to the intensity of the higher running 137 bp band).

These primers were not visible in FIG. 14, Photographs A and B because they were associated with PNA Quencher (Photograph A). Under denaturing conditions, the primers fluoresce because they are dissociated from the PNA Quenchers. Interestingly, the dsDNA size marker disappears in FIG. 14, Photograph C presumably because the ethidium is non fluorescent under the denaturing conditions.

Summary:

Serial dilutions of template DNA were made and then used in PCR amplification reactions. The intensity of fluorescent signal generated in PCR reactions was shown to exhibit a direct correlation with the quantity of input template over a 7 log range (1 fmole to 1 zmole). The fluorescent signal measured in the spectrofluorophotometer correlated well with the quantity of fluorescent dsDNA seen on a polyacrylamide gel and the quantity of fluorescent primer consumed in each PCR reaction. Taken as a whole, this experiment conclusively demonstrates that the fluorescent signal generated in each PCR reaction correlated with the quantity of input template and hence the quantity of dsDNA amplicon generated by the PCR process. Consequently, this assay demonstrates the feasibility of generating a standard curve for a closed tube assay which can be used to determine the quantity of target sequence or target molecule in an unknown sample. Furthermore, the assay is very sensitive since it is capable of producing signal which was detectable above background down to 1 zeptomole (~600 molecules), the lowest target level examined.

Example 16

Use of Detection Complexes in Multiplex PCR

Overview

For this example, a Multiplex PCR assay was performed using two sets of independently detectable PCR Detection Complex primers wherein each set of primers is designed to amplify one of two different DNA target molecules if present in the assay. The first primer set is labeled with fluorescein (green) and specifically amplifies the K-ras gene sequence in the K-ras plasmid (as described in Example 15). The second primer set is labeled with rhodamine (red) and specifically amplifies a region in the BR322 plasmid. Both PCR Detection Complex primers utilize the same common PNA annealing polymer (PNA Quencher) comprising a dabcyl quencher moiety which quenches the fluorescence of both the fluorescein and rhodamine labels until amplification occurs to thereby dissociate the Detection Complex.

Materials and Methods
Probes, Primers and Templates:
  PNA Quencher:

```
PNA Quencher (Table 1, NO. 6) C Dabcyl(K)-AGTAAGCGTTAGT-OO-+-Ac N
C = Carboxy terminus,
N = Amine terminus, "Ac", "K""+""Dabcyl" and "O" are previously
defined.
```

DNA Primers:

The 3' DNA Primers comprise both a priming sequence which is complementary to the priming site on the target nucleic acid of interest and a common complex forming segment (CFS; shown in Bold text) to which the PNA Quencher hybridizes. The 5' primers are not labeled.

```
Primer Set A (K-ras Primer Set):
5'Primer      5'   HO-ATGACTGAATATAAACTTGT-OH                      3'   SEQ.ID No. 6

3'Primer      5'   Flu-TCATTCGCAATCACTCTATTGTTGGATCATATT-OH        3'   SEQ. ID No. 3

Primer Set B (BR322 Primer Set):
5'Primer      5'   HO-CACTATCGACTACGCGATCA-OH                      3'   SEQ. ID No. 7

3'Primer      5'   Rho-TCATTCGCAATCATAGGTTGAGGCCGTTGAGCA-OH        3'   SEQ. ID No. 8
```

Primer Set C (K-ras & BR322 Primer Set):

This primer set comprises a mixture of Primer Set A & Primer Set B. This primer set is useful for simultaneous multiplex identification of one or both of the K-ras plasmid and the BR322 plasmid templates.

The BR322 3' Primer (Seq. ID No. 8) labeled with tetramethyl rhodamine (Rho) was obtained from Genosys (The Woodlands, Texas). The 3' K-ras Primer was made using commercially available reagents and instrumentation. The PNA Quencher was diluted in 50% aqueous DMF and stored at 4° C. whereas DNA primers and DNA templates were diluted in TE and stored at 4° C.

dsDNA Template

K-ras plasmid: Preparation of this plasmid and the sequence of the amplified region of the plasmid are described in Example 15.

BR322 plasmid: This plasmid is commercially available and was obtained from New England BioLabs as part # 303-3S. The sequence of the amplified region of the plasmid is illustrated below.

dsDNA Template (amplified region only; priming sites are underlined)

As described in Example 15, the region of K-ras plasmid amplified by the primers is 111 bp in length. However, when amplified using both of the DNA primers described in this Example 16, a 124 bp amplicon is generated since incorporation of one 13 bp complex forming segment (CFS) from the 3' primer extends the amplicon by 13 bp (111+13=124).

Similarly, the BR322 plasmid is a commonly used and widely available cloning vector. When amplified using the primers described in this Example 16, a 274 bp amplicon is extended by incorporation of one 13 bp complex forming segment in the 3' primer. Therefore, the length of the expected amplicon is 287 bp (274+13=287 bp).

Other reagents not specified are described in Example 15.

PCR Assays:

PCR reactions were performed in the Perkin-Elmer 2400 thermocycler in individual mini-eppendorf tubes. Each 50 µL PCR reaction contained 3 mM MgCl$_2$, 250 µM ATP, 250 µM CTP, 250 µM GTP, 250 µM TTP, 2 units AmpliTaq DNA polymerase, 50 mM KCl, and 10 mM TRIS, pH 8.3. Each reaction also contained primer sets A, B, or C and the PNA Quencher. To reactions containing target, 1 µL (6E+09 molecules/µL) of the appropriate plasmid was added.

Primer Set A comprised 0.1 µM K-ras 3' primer, 0.2 µM K-ras 5' primer as well as 0.4 µM PNA Quencher. Primer Set B comprised 0.05 µM BR322 3' primer, 0.1 µM BR322 5' primer, as well as 0.4 µM PNA Quencher. Reactions using Primer Set C comprised 0.1 µM K-ras 3' primer, 0.2 µM K-ras 5' primer, 0.05 µM BR322 3' primer, 0.1 µM BR322 5' primer and 0.6 µM PNA Quencher. Asymmetric PCR amplification was chosen for this example to thereby generate an excess of the non-labeled strand as this was

```
         ← 5'Priming Site →
5'   ...CACTATCGACTACGCGATCATGGCGACCACACCCGTCCTGTGGATCCTCTACGCCGGACG...
3'   ...GTGATAGCTGATGCGCTAGTACCGCTGGTGTGGGCAGGACACCTAGGAGATGCGGCCTGC...

...CATCGTGGCCGGCATCACCGGCGCCACAGGTGCGGTTGCTGGCGCCTATATCGCCGACAT...
     ...GTAGCACQGGCCGTAGTGGCCGCGGTGTCCACGCCAACGACCGCGGATATAGCGGCTGTA...

...CACCGATGGGGAAGATCGGGCTCGCCACTTCGGGCTCATGAGCGCTTGTTTCGGCGTGCG...
     ...GTGGCTACCCCTTCTAGCCCGAGCGGTGAAGCCCGAGTACTCGCGAACAAAGCCGCACCC...

...TATGGTGGCAGGCCCCGTGGCCGGGGGACTGTTGGGCGCCATCTCCTTGCATGCACCATT...
     ...ATACCACCGTCCGGGGCACCGGCCCCCTGACAACCCGCGGTAGAGGAACGTACGTGGTAA...

...CCTTGCGGCGGCGGTGCTCAACGGCCTCAACCTA...        3'   SEQ. ID No. 9
     ...GGAACGCCGCCGCCACGAGTTGCCGGAGTTGGAT...        5'   SEQ. ID No. 10
                      ← 3'Priming site →
``` expected to foster the displacement of all the PNA Quencher from the double stranded amplicon during the amplification reaction.

The PCR protocol involved a 20 second warm up to 95° C. (1st round only), followed by denaturing at 95° C. for 20 seconds, annealing at 55.0° C. for 30 seconds, and extension at 74° C. for 30 seconds denaturation-annealing-extension cycle was repeated for 35 cycles. An additional 5 minute extension step at 74° C. was done after cycle 35.

As was performed in Example 15, the fluorescence of each reaction was examined in a Wallac Multilabel counter. For each measurement, 10 μL of each sample was diluted with 90 μL of a solution containing 50 mM TRIS-HCl pH 8.3, 100 mM NaCl. When detecting fluorescein (green), the sample is excited with light passing through a 485 nm filter and the emission is obtained from light passing through a 535 nm filter (the Green Filter Set). When detecting rhodamine (red) the sample is excited with light passing through a 530 nm filter and the emission is obtained from light passing through a 590 nm filter (the Red Filter Set).

After PCR, 10 μL of each sample was mixed with 2.5 μL of 5× loading dye and the crude reaction product was then separated on a 10–20% gradient polyacrylamide gel. For this example, the gel was examined and photographed using a transilluminator both before and after ethidium bromide staining. The two negative images of photographs which comprise FIG. 16 are of the unstained gel (Image A) and the ethidium bromide stained gel (Image B).

Results

Figure 15:
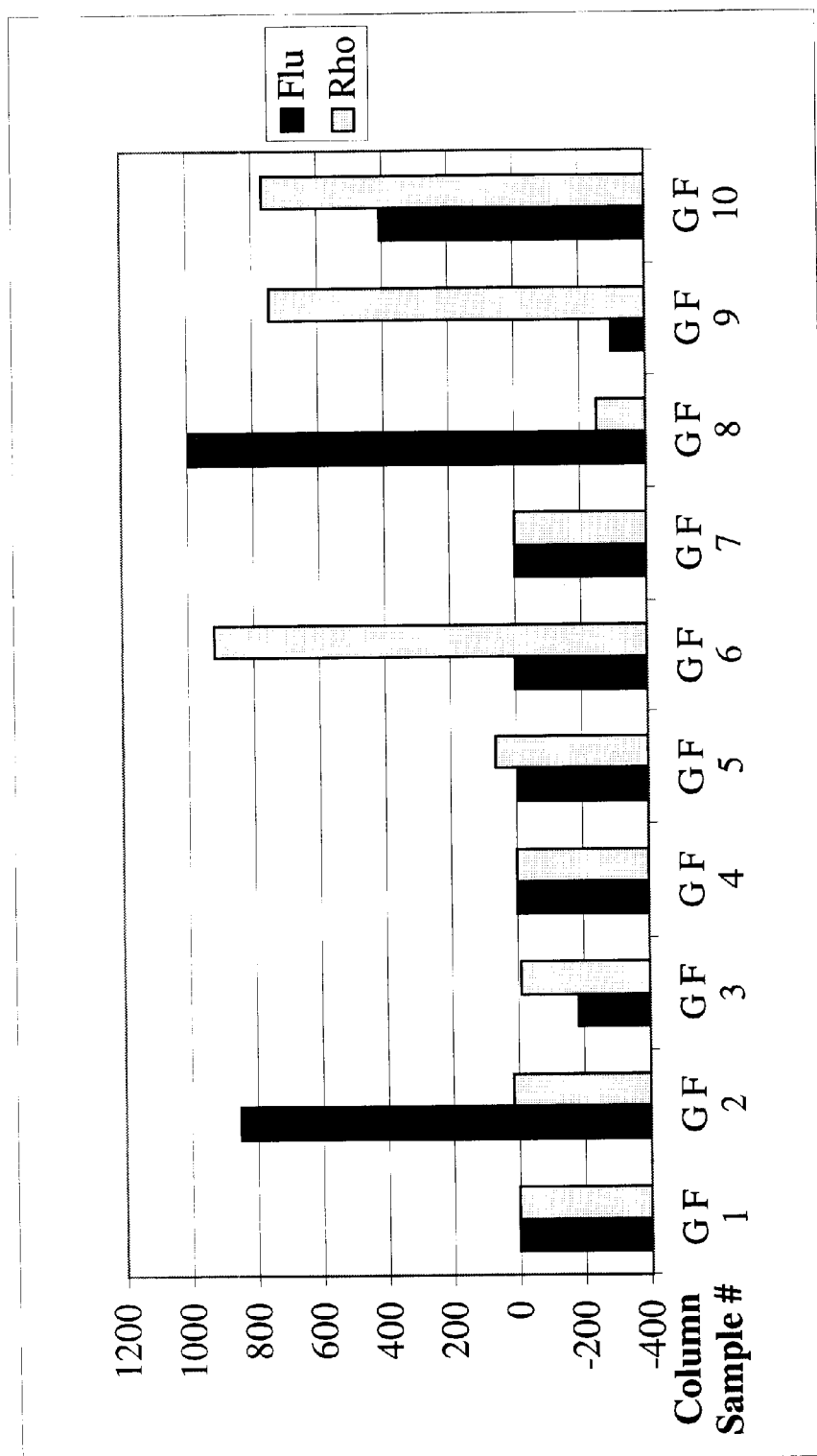
FIG. 15 is a graphic illustration of data generated for a multiplex PCR assay using independently detectable PCR Detection Complexes.
Figure 16:
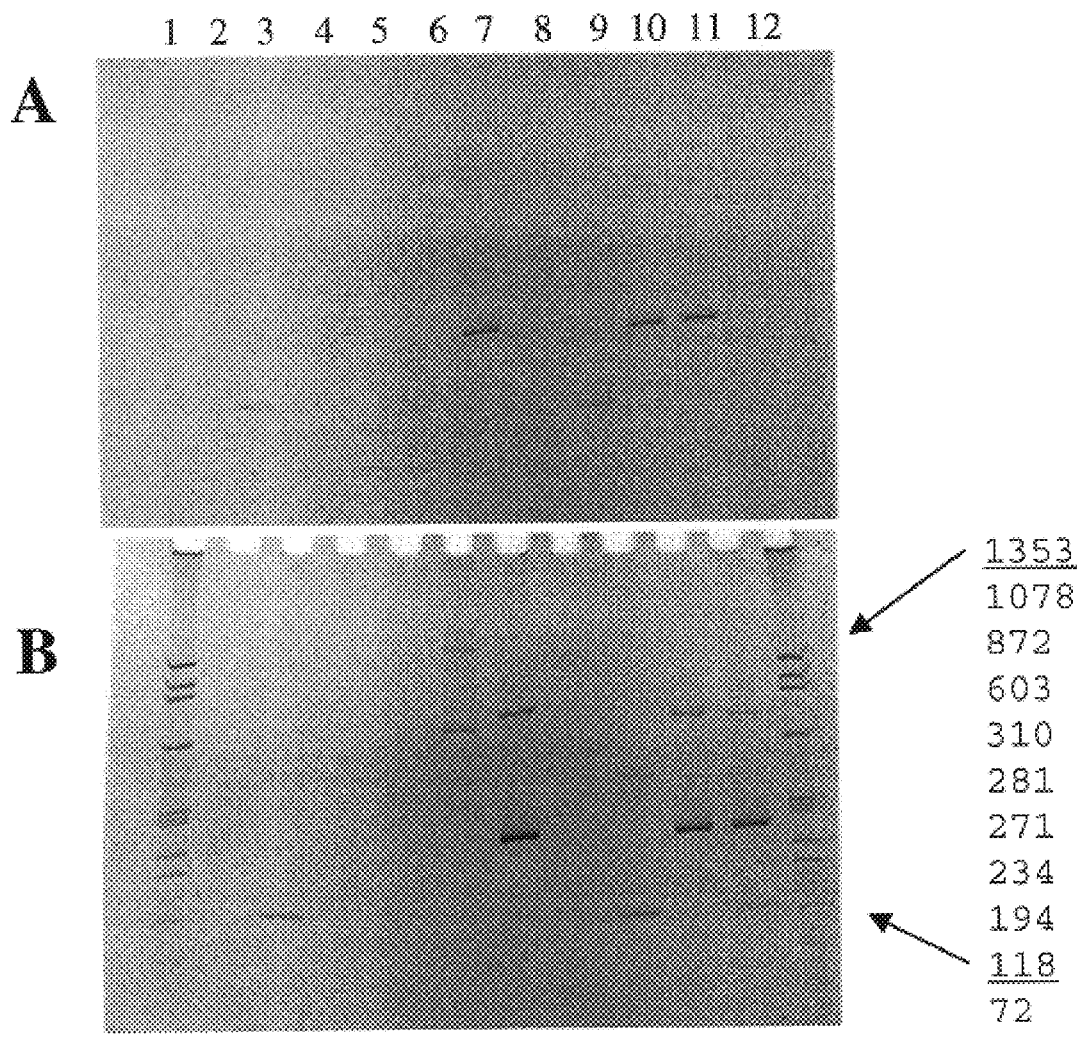
FIGS. 16A and 16B are electronic composite negative images of photographs taken of a polyacrylamide gel used to analyze PCR reaction products for fluorescence.

Data obtained for this Example 16 is presented in Table 4 and FIGS. 15 and 16. With reference to Table 4, data is summarized for both the variable assay components as well as processed data obtained from the Wallac multilabel counter. Specifically, the Sample No. is identified in column A; the nature of the Target present in the reaction is identified in column B; the Primer Set or Sets is identified in column C; the Rhodamine post-PCR fluorescence data for each sample is presented in column D; and the Fluorescein post-PCR fluorescence data for each sample is presented in column E.

1768−917=850 (row 2, column G)). All other values for columns F and G are similarly derived within each Primer Set.

With reference to Table 4, rows 1–3 and columns F and G, there was a clear correlation between the presence of the K-ras plasmid and an increase in signal from the fluorescein label when Primer Set A (the K-ras Primer Set—green fluorophore) was used. Specifically, negative values (row 3, columns F & G) were obtained when the BR322 plasmid was used but a strong value of 850 (row 2, column G) was obtained with the Green Filter Set when the K-ras plasmid was present. The slightly positive value in row 2, column F may be explained merely because the filter sets used in the multilabel counter are not entirely perfect in cut off and the value may actually represent signal from the fluorescein label which is measurable with the Red Filter Set. This interpretation is consistent with the lack of any amplified products as seen in the polyacrylamide gel analysis (See: discussion below). Nevertheless, the difference in the signal intensity between the data in rows 2 and 3, columns F and G is striking and clearly demonstrates that a strong positive result was obtained when the K-ras plasmid was present in the assay.

Similarly and with reference to Table 4, rows 4–6 and columns F and G, there was a clear correlation between the presence of the BR322 plasmid and an increase in signal from the rhodamine label when Primer Set B (the BR322 Primer Set—red fluorophore) was used. Specifically, small or negative values (row 5, columns F & G) were obtained when the K-ras plasmid was present but a strong value of 920 (row 6, column F) was obtained with the Red Filter Set when the BR322 plasmid was present. The slightly positive value in row 5, column F appears to be due to non-specific priming of the K-ras plasmid with this BR322 Primer Set. This interpretation is consistent with the generation of non-specific amplimer products as can be seen in the polyacrylamide gel analysis (See: discussion below). Nevertheless, the difference in signal intensity between the data in rows 5 and 6, columns F and G is striking and clearly demonstrates that a strong positive result was obtained for the BR322 plasmid. This positive result was clearly distinguishable over the false positive resulting from non-specific priming.

TABLE 4

| A<br>Sample<br>No. | B<br>Target | C<br>Primer<br>Set | D<br>Rhodamine<br>post-PCR | E<br>Fluorescein<br>post-PCR | F<br>Rhodamine<br>minus-NT | G<br>Fluorescein<br>minus-NT |
|---|---|---|---|---|---|---|
| 1 | 1 | No Target | A | 263 | 917 | 0 | 0 |
| 2 | 2 | pK-ras | A | 280 | 1768 | 17 | 850 |
| 3 | 3 | pBR322 | A | 253 | 734 | (−10) | (−183) |
| 4 | 4 | No Target | B | 537 | 118 | 0 | 0 |
| 5 | 5 | pK-ras | B | 600 | 115 | 63 | (−3) |
| 6 | 6 | pBR322 | B | 1457 | 118 | 920 | 0 |
| 7 | 7 | No Target | C | 733 | 716 | 0 | 0 |
| 8 | 8 | pK-ras | C | 480 | 1711 | (−252) | 994 |
| 9 | 9 | pBR322 | C | 1478 | 418 | 745 | (−298) |
| 10 | 10 | pK-ras and pBR322 | C | 1497 | 1122 | 764 | 406 |

To generate the processed data presented in columns F and G of Table 4, the No Target Control for each Primer Set was subtracted from the value for the "post-PCR" fluorescence value for either the rhodamine or fluorescein label. For Example, the values in columns F and G of row 1 are both zero since 263−263 is zero (row 1, column F) and 917−917 is zero (row 1, column G). The values for data in row 2 were similarly derived (280−263=17 (row 2, column F) and Similarly and with reference to Table 4, rows 7–10 and columns F and G, there was a clear correlation between the presence of the BR322 plasmid and an increase in signal from the rhodamine label as well as a clear correlation between the presence of the K-ras plasmid and an increase in signal from the fluorescein label in all amplification reactions wherein one or more targets were present. With reference to row 8, there was no signal detected for the rhodamine label and a very strong signal for the fluorescein label. This is consistent with the absence of the BR322 plasmid and the presence of the K-ras plasmid, respectively. Likewise, and with reference to row 9, there was no signal detected for the fluorescein label and a very strong signal for the rhodamine label. This is consistent with the absence of the K-ras plasmid and the presence of the BR322 plasmid, respectively. Finally, and with reference to row 10, a strong signal is detected for both the fluorescein and rhodamine labels. This is consistent with the presence of both the K-ras and BR322 plasmid targets.

Curiously, there was no observed mis-priming when both primer sets and the K-ras plasmid were present in the assay (Compare the data in columns F and G, row 5 with the data in columns F and G of rows 8 and 10). The absence of mis-priming in the multiplex assay suggests, for an unknown reason, that it may be beneficial to utilize two or more primer sets in a single PCR reaction to thereby reduce or eliminate mis-priming.

The tabular data presented in columns F and G of Table 4 is also represented in FIG. 15 in a bar graph format. The graphical illustration visually conveys the substantial difference in the relative intensity of fluorescent signals generated in the assay so that the differences between true positive and negative results are easier to identify.

As described above, the products of each amplification reaction were analyzed by polyacrylamide gel electrophoresis and two photographs were taken of the gel before and after ethidium bromide staining. FIG. 16 (A and B) is a digital composite of the negative of an image of each of the two photographs of the same polyacrylamide gel. The photographic images presented in FIG. 16 yield conclusive proof that, with the exception of sample 5, the increase in fluorescence observed in the PCR amplification reactions resulted from specific amplification of the intended plasmid to yield an amplicon of the anticipated size and having the expected inherent fluorescent properties. The photographic images are displayed with the sample wells at the top with each gel image comprising 12 lanes. Lanes 1 and 12 contain 1 µg of PhiX174 dsDNA digested with Hae III. Lanes 2 through 11 are PCR reaction Sample Numbers 1 through 10.

With reference to FIG. 16, Photograph A, native fluorescence of the gel was observed immediately after the gel was run by placing it on a transilluminator. Fluorescence bands of expected color, given the nature of the label in the PCR Detection Complex, were visible in lanes 3 (green), 7 (red), 9 (green), 10 (red) and 11 (green and red).

With reference to FIG. 16, image B, fluorescence was observed on the transilluminator after the gel was treated with ethidium bromide. The bands visible in Image B are those polymers or PCR products which are either inherently fluorescent or are stained with ethidium bromide. Again, bands are visible in lanes 3, 7, 9, 10 and 11 as well as in lanes 1 and 12 containing the size markers. The predominate band in lanes 3 and 9 of image B, which were also visible in image A, lie between the 118 bp and 194 bp bands of the size marker. This fluorescence and size data is consistent with the expected properties of the amplicon for the K-ras plasmid (124 bp). The predominate band in lanes 7 and 10 of image B, which were also visible in image A, lie between the 234 bp and 310 bp bands of the size marker. The fluorescence and size data is therefore consistent with the expected properties of the amplicon for the BR322 plasmid (287 bp). Similarly, bands having the expected properties for both the BR322 and K-ras amplicons were present in lane 11 of both images A and B.

With reference to lane 6 (Sample No. 5) of image B, weak bands are observed in the gel which do not appear to be the expected amplicon for either the K-ras or BR322 plasmid. With regard to sample number 5, the reaction contained the K-ras plasmid and the BR322 Primer Set. Consequently, no amplification was expected. Since multiple weak bands are present, the data suggests that mis-priming may have occurred to thereby generate the non-specific products. This data is consistent with the slight positive fluorescence signal recorded in Table 4, row 5, column F. Curiously, mis-priming does not seem to have occurred in samples 8 or 10 (Lanes 8 and 11) wherein both the K-ras plasmid and the pBR322 Primer Set was present.

With reference to lanes 3, 7, 9, 10 and 11, a faint higher running band is visible in the ethidium stained gel (Image B). This artifact appears to be associated with asymmetric PCR and is therefore believed to be the single stranded nucleic acid product which is over-expressed due to the asymmetric PCR reaction.

Note:

Sample Number 5 of this experiment demonstrates that false positive results may be obtained from non specific hybridization events such as primer dimer formation and target mis-priming. These are typical problems associated with any PCR reaction and therefore the Detection Complexes described herein may also exhibit these undesirable properties when the amplification reaction is performed under less than optimal PCR conditions. However, those of ordinary skill in the art will recognize that amplification conditions can be optimized to minimize or eliminate these problems using no more than routine experimentation. Generally the amplification conditions are optimized by either modifying the primers or varying the "Suitable Hybridization Conditions" under which the assay is performed (See: the Specification at page 22). Also see Example 18 which demonstrates the principle of "Internal Assay Monitoring" as a real-time or end-point method which can insure the accuracy of a closed tube assay.

Summary:

The data for the individual components of the multiplex assay were shown to generate a clear positive result which could be distinguished from signal resulting from non-specific amplification. When the components were combined into the multiplex assay, the results were similarly impressive. Taken as a whole, this example demonstrates the feasibility of performing a closed tube multiplex analysis of a single sample to simultaneously determine the presence, absence or quantity of two or more target sequences or target molecules.

Example 17

Point Mutation Detection Using PCR Detection Complexes In Combination With PCR Clamping Overview This Example 17 utilizes a modification of the K-ras system used in Example 15. Specifically, the primer sets have been modified to thereby demonstrate that point mutation discrimination can be achieved when combining PCR clamping with the PCR Detection Complexes described herein.

Materials and Methods
Probes, Primers and Templates:
PNA Quencher:

```
PNA Quencher (Table 1, No. 6)  C  Dabcyl(K)-AGTAAGCGTTAGT-OO-+-Ac  N
C = Carboxy terminus,
N = Amine terminus, "Ac", "K""+""Dabcyl" and "O" are previously
defined.
```

DNA Primers:

The 5' K-ras primers comprise a 15 nucleotide priming sequence which is complementary to the priming site on either the wild type (WT) or mutant (MU) target nucleic acid of interest as well as a common complex forming segment (CFS; shown in Bold text) to which the PNA Quencher hybridizes. The 5' K-ras primers for the mutant (K-rasMU) and wild type (K-ras) targets differ by one nucleotide in the middle of the priming section and are thus related as point mutations (Bold and underlined text). The 3' primer is not labeled.

dsDNA Template

K-ras: This plasmid was prepared as described in Example 15. K-rasMU: This plasmid contains a sub-cloned sequence from a cell line which has a G to T mutation at base 129 of the human K-ras gene. But for incorporation of the mutation, this plasmid was created in the same way, and at the same time as the wild type plasmid described in Example 15. Thus K-ras and K-rasMU are related as plasmids containing a point mutation of the K-ras gene. The M13–40 primer hybridizes to a region in the cloning vector, pCR2.1, used to generate both the K-ras and K-rasMU plasmids. In the absence of a clamping probe, use of the M13–40 primer

```
5' Primers:

5'K-rasWT       5' Flu-TCATTCGCAATCAACGCCACCAGCTCCA-OH   3'   SEQ, ID No. 11
Primer K-rasMU Primer  5' Flu-TCATTCGCAATCAACGCCACAAGCTCCA-OH   3'   SEQ. ID No. 12

3' Primer:

M13-40 Primer   5' HO-GTTTTCCCAGTCACGAC-OH              3'   SEQ. ID No. 13
```

The M13–40 primer is commercially available and was obtained from New England BioLabs as part #1212. PNA Clampling Probes and PNA Quencher were diluted in 50% aqueous DMF and stored at 4° C. DNA Primers and DNA templates were diluted in TE and stored at 4° C.

PNA Clamping Probes:

The two PNA Clamping Probes differ by one nucleobase (Bold and underlined text) present in the middle of the and either the K-rasWT primer or the K-rasMU primer will generate a 183 base pair amplicon regardless of whether the K-ras or K-rasMU plasmids are present in the amplification reaction.

dsDNA WT and MU Template (amplified region only; the point mutation is illustrated in bold underlined text).

```
                    ← 5'Priming Site →
        5'  ...ACGCCACCAGCTCCAACTACCACAAGTTTATATTCAGTCATTTCGAATTCTGCAGATATC...
        3'  ...TGCGGTGGTCGAGGTTGATGGTGTTCAAATATAAGTCAGTAAAGCTTAAGACGTCTATAG...

...CATCACACTGGCGGCCGCTCGAGCATGCATCTAGAGGGCCCAATTCGCCCTATAGTGAGT...
            ...GTAGTGTGACCGCCGGCGAGCTCGTACGTAGATCTCCCGGGTTAAGCGGGATATCACTCA...

...CGTATTACAATTCACTGGCCGTCGTTTTACAACGTCGTGACTGGGAAAAC...3' SEQ. ID No. 14
            ...GCATAATGTTAAGTGACCGGCAGCAAAATGTTGCAGCACTGACCCTTTTG...5 'SEQ. ID No. 15
                                                    ← 3'Priming Site →
``` oligomer. Thus, they are related as single nucleobase mismatches.

```
        PNA-WT    N    H-OO-ACGCCACCAGCTCCA-NH₂    C
        PNA-MU    N    H-OO-ACGCCACAAGCTCCA-NH₂    C
N = Amine terminus,
C = Carboxy terminus, "O" is previously defined.
```

Other reagents not specified are as described in Example 15.

PCR Assays:

PCR reactions were performed in the Perkin-Elmer 2400 thermocycler in individual mini-eppendorf tubes. Each 30 μL PCR reaction contained 2.25 mM $MgCl_2$, 200 μM ATP, 200 μM CTP, 200 μM GTP, 200 μM TIP, 166 nM M13–40 primer, 166 nM PNA Quencher, 1 unit AmpliTaq DNA polymerase, 50 mM KCl, and 10 mM TRIS, pH 8.3. Each reaction also contained one of either 83 nM K-rasWT or 83 nM K-rasMU primer as well as 1 μL of 10 nM K-ras plasmid, 1 μL or 10 nM K-rasMU plasmid, or 1 μL of water (the "No Target" control). In addition, reactions also contained one of either 1.25 μL of 20 μM PNA-WT, 1.25 μL of 20 µM PNA-MU, or 1.25 µL 50% aqueous DMF (the "No PNA Clamp" control). A summary of the variable reagents added to each PCR reaction are displayed in Table 5.

The PCR protocol involved a 20 second warm up to 95° C. (1st round only), followed by denaturing at 95° C. for 5 seconds, annealing for 30 seconds, and extension at 74° C. for 30 seconds. The denaturation-annealing-extension cycle was repeated for 25 cycles. The annealing temperature for the PCR protocols depended on which primer was used; 54° C. for K-rasMU primer (samples 6–10) and 56° C. for K-rasWT primer (samples 1–5).

After the PCR reactions were completed, the tubes were placed on a transilluminator, to thereby generate visible fluorescence in the tubes, and photographed. The composite digital negative image of the photograph is presented in FIG. 18.

Additionally, the fluorescence of each reaction was examined in a Wallac multilabel counter. For each measurement, a 5 µL sample was diluted with 45 µL of a solution containing 50 mM KCl, 3 mM MgCl and 10 mM Tris-HCl, pH 8.3. The fluorescence was examined using the Green Filter Set (See: Example 16). Raw fluorescence data was recorded and is reproduced in Table 5, column E.

Similarly, a 10 µL sample of each reaction was mixed with 2.5 µL of 5× loading dye and separated on a 10–20% gradient polyacrylamide gel. For this example, the gel was examined and photographed using a transilluminator both before and after ethidium bromide staining. The two negative images of photographs which comprise FIG. 17 are of the unstained gel (Image A) and the ethidium bromide stained gel (Image B).

Results

Figure 17:
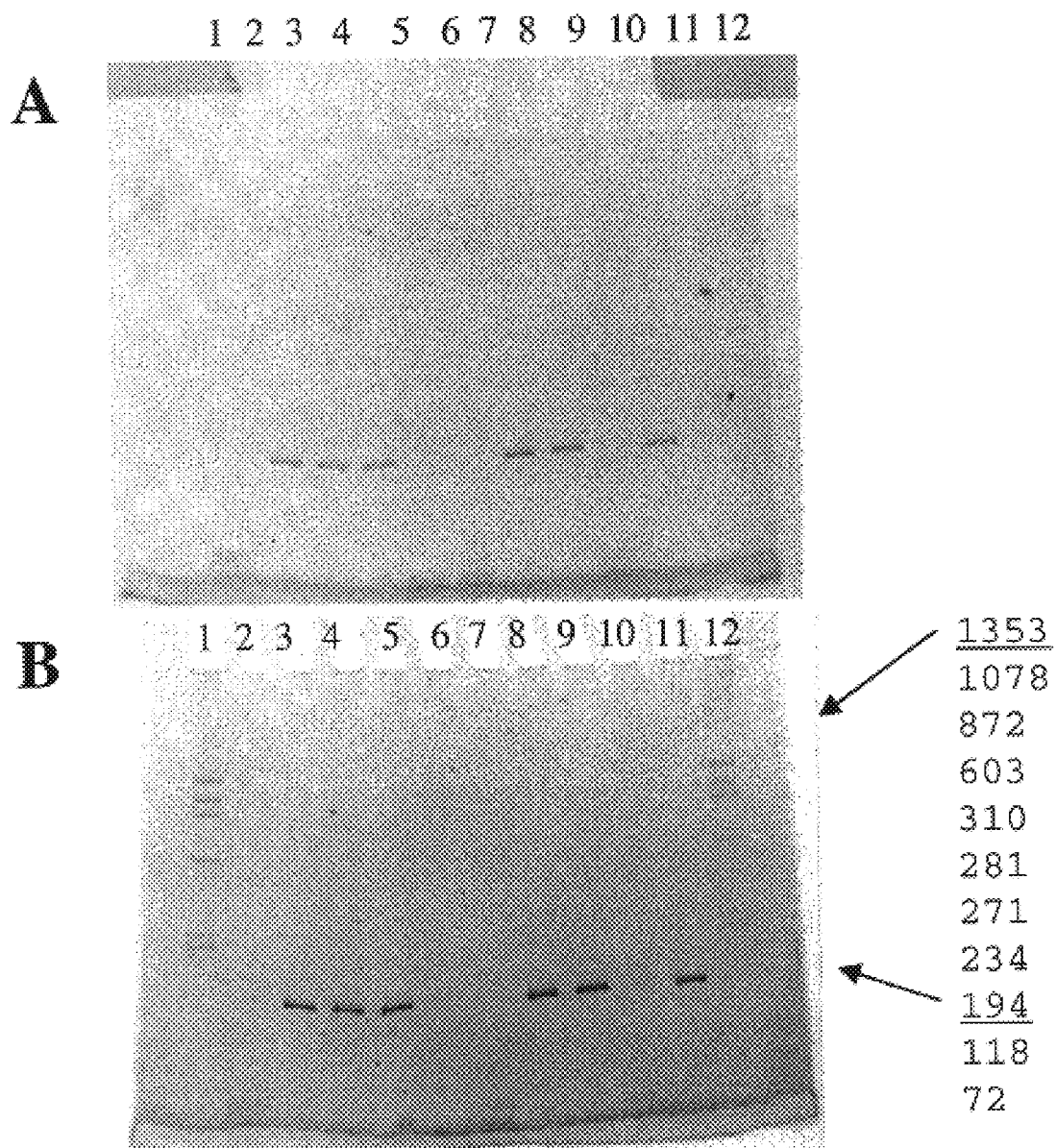
FIGS. 17A and 17B are electronic composite negative images of photographs taken of a polyacrylamide gel used to analyze PCR reaction products for fluorescence.
Figure 18:
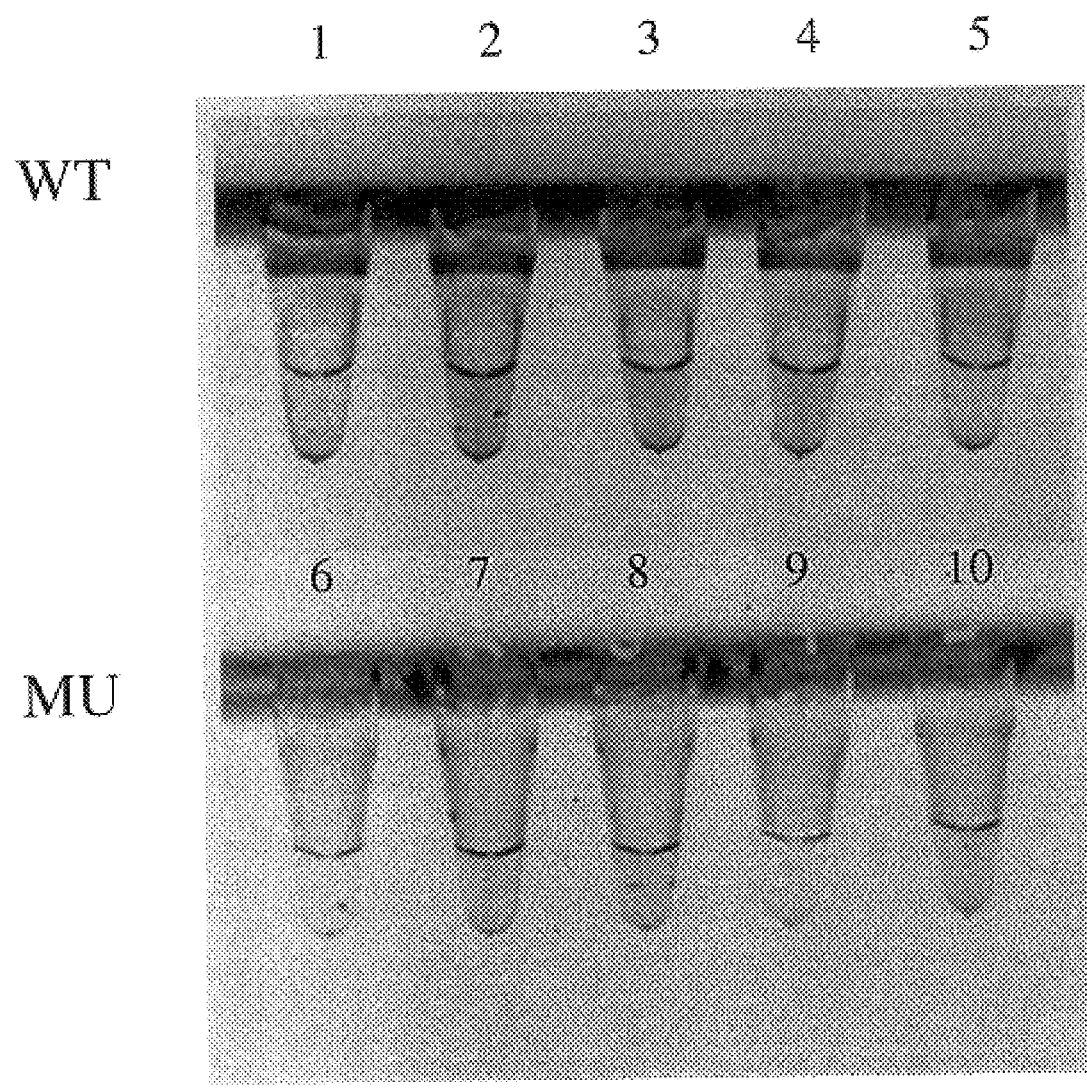
FIG. 18 is an electronic composite negative image of two photographs taken of unopened PCR reaction sample tubes lying on a transilluminator.

Data obtained for this Example 17 is presented in Table 5 and FIGS. 17 and 18. With reference to Table 5, the Sample Number is identified in column A; nature of the 5' Primer is identified in column B; the presence or identity of the target is identified in column C; the presence or identity of the PNA Clamping Probe is identified in column D and the raw post-PCR fluorescence data for the individual samples is recorded in column E.

Generally, the Table is divided into Samples 1–5 wherein the K-ras-WT 5'-Primer was present in the reaction and Samples 6–10 wherein the K-ras-MU 5'-Primer was present. Within each of these two groups, a No Target and No PNA Clamp control was performed (See rows 1 and 6). This negative control provides a baseline for comparison with all other reaction samples. Within each of these two groups, assays were also performed using one of the wild type (rows 2, 4, 7 and 9) or mutant (rows 3, 5 8 and 10) K-ras plasmids; with (rows 4, 5, 9 and 10) and without (rows 2, 3, 7 and 8) a suitable PNA Clamping Probe.

With reference to column E of Table 5, the fluorescence intensity of the No Target and No PNA Clamping probe controls (see column E, rows 1 and 6) are very low (Each data point is well below 1000 relative light units (RLU)). This data is consistent with the lack of any amplification occurring in the reaction. This number is representative of the background fluorescence of the system.

With reference to rows 2 and 3, the relative fluorescence for both samples, as measured by the multilabel counter, is clearly well above the fluorescence measured in the negative control (sample 1) and is essentially the same for both reactions (2774 and 2652, respectively). This data indicates that the 5'-Primer amplifies both the wild type and mutant plasmids with roughly equivalent efficiency, under the conditions of the assay and in the absence of the PNA Clamping Probe (See column D).

By comparison, and with reference to rows 4 and 5, the relative fluorescence for samples containing the mutant PNA Clamping Probe (PNA-MU) were substantially different as measured by the multilabel counter. When PNA-MU and the mutant plasmid template (K-rasMU) were present in the reaction, the fluorescent signal was roughly equivalent to that observed in the absence of any target (Compare row 1, column E and row 5, column E to row 3, column E). This data indicated that virtually no amplification occurred in this reaction. By comparison, the fluorescent intensity was roughly equivalent to that observed in the absence of any PNA Clamp when the wild type plasmid (K-ras) was present (Compare row 4, column E and row 2, column E to row 1, column E). This data demonstrated that PNA Clamping could be combined with the PCR Detection Complexes to thereby achieve a closed tube assay suitable for point mutation discrimination.

Similarly, and with reference to rows 7 and 8, the relative fluorescence for both samples, as measured by the multilabel counter, is clearly well above the fluorescence measured in the negative control (Sample 6) and is essentially the same for both reactions (2878 and 3030, respectively). This data indicates that the 5'-Primer amplifies both the wild type and mutant plasmids with roughly equivalent efficiency, under the conditions of the assay, in the absence of the PNA Clamp.

By comparison, and with reference to rows 9 and 10, the relative fluorescence for samples containing wild type PNA Clamping Probe (PNA-WT) were substantially different as measured by the multilabel counter. When PNA-WT and the wild type plasmid template (K-ras), were present in the reaction, fluorescent signal was roughly equivalent to that observed in the absence of any target (Compare row 9, column E and row 6, column E to row 7, column E). This data indicated that no amplification occurred in this reaction. By comparison, the fluorescent intensity was roughly equivalent to that observed in the absence of any PNA Clamping Probe when the mutant plasmid (K-rasMU) was present (Compare row 10, column E and row 8, column E to row 6, column E). Again, this data demonstrated that PNA Clamping could be combined with the PCR Detection Complexes of this invention to thereby achieve a closed tube assay suitable for point mutation discrimination.

TABLE 5

| A Sample # | B 5'-Primer | C Target | D PNA Clamp | E Raw Fluorescence Data |
|---|---|---|---|---|
| 1 | K-ras-WT | No Target | No PNA Clamp | 178 |
| 2 | K-ras-WT | K-ras | No PNA Clamp | 2774 |
| 3 | K-ras-WT | K-rasMU | No PNA Clamp | 2652 |
| 4 | K-ras-WT | K-ras | PNA-MU | 2452 |
| 5 | K-ras-WT | K-rasMU | PNA-MU | 296 |
| 6 | K-ras-MU | No Target | No PNA Clamp | 750 |
| 7 | K-ras-MU | K-ras | No PNA Clamp | 2878 |
| 8 | K-ras-MU | K-rasMU | No PNA Clamp | 3030 |
| 9 | K-ras-MU | K-ras | PNA-WT | 352 |
| 10 | K-ras-MU | K-rasMU | PNA-WT | 2632 |

As described above, the products of each amplification reaction were analyzed by polyacrylamide gel electrophoresis and two photographs were taken of the gel before and after ethidium bromide staining. FIG. 17 (A and B) is a digital composite of the negative of an image of each of the two photographs of the same polyacrylamide gel. The photographic images presented in FIG. 17 yield conclusive proof that the increase in fluorescence observed in the PCR amplification reactions resulted from specific amplification of the plasmid present in the reaction to thereby yield an amplicon of the anticipated size and having the expected inherent fluorescent properties.

The photographic images are displayed with the sample wells at the top with each gel comprising 12 lanes. Lanes 1 and 12 contain 1 μg of PhiX174 dsDNA digested with Hae III. Lanes 2 through 11 are PCR reaction Sample Numbers 1 through 10.

With reference to FIG. 17, Image A, a strong green fluorescent band was observed in lanes 3, 4, 5, 8, 9 and 11. This corresponds to samples 2, 3,4, 7, 8 and 10, respectively. The presence of the strong fluorescent band in the gel is consistent with the data presented in Table 5 which indicates that amplification occurred only in samples 2, 3, 4, 7, 8 and 10.

With reference to FIG. 17, Image B, fluorescence was observed on the transilluminator after the gel was treated with ethidium bromide. The bands visible in Image B are those polymers or PCR products which are either inherently fluorescent or are stained with ethidium bromide. Again the same strong fluorescent bands were visible in lanes 3, 4, 5, 8, 9 and 11 of the ethidium stained gel. Additionally, the size markers in lanes 1 and 12 were visible after ethidium bromide staining. The bands ran approximately between the 118 bp and 194 bp fragments of the size marker. This is consistent with a 183 bp amplicon. Consequently, the fluorescence and fragment size data is consistent with the properties expected for the amplicon given the template and primer combinations used herein.

With reference to FIG. 18, a digital composite of the negative image of a photograph of the post PCR reaction tubes sitting of the transilluminator is presented. Samples are identified as 1 through 10 in the Figure. Analysis of the image confirms that fluorescent signal was visible to the eye in tubes 2, 3, 4, 7, 8 and 10. This data is consistent with the data obtained with the multilabel counter as well as the polyacrylamide gel and therefore confirms that either an instrument or the human eye can be used to analyze the closed tube assays described herein.

Summary:

Taken as a whole the data demonstrates that the PCR Detection Complexes of this invention can be combined with PCR clamping to thereby generate closed tube assays suitable for both real-time and end point analysis of point mutations. Moreover, the methodology is so simple, the results can be interpreted by merely looking at the sample tubes under ultraviolet light.

Example 18

Simultaneous Use Of Detection Complexes and Unimolecular "Beacon" Probes In A Multiplex Assay Overview This Example was performed to demonstrate the feasibility of commingling independently detectable Detection Complexes with unimolecular "Beacon" probes (a Linear Beacon is used in this Example) in a single multiplex assay. Non-limiting examples of uses for this assay format include internal PCR assay monitoring and independent identification of a feature or features of an amplicon.

Materials and Methods

Probes, Primers and Templates:
PNA Oligomers:

```
PNA Fluor:

CY3-PNA      C   (Cy3)K-AGTAAGCGTTAGT-OO-+-Ac        N

Linear Beacon:

LBK.003      N   Flu-O-ACGCCACCAGCTCCA-K(DABCYL)    C
C = Carboxy terminus,
N = Amine terminus, "K", "Flu", "Ac", "+""Cy3" and
"O" are previously defined herein.
```

DNA Primers: The 3' DNA Primers comprise both a priming sequence which is complementary to the priming site on the target nucleic acid of interest and a common complex forming segment (CFS; shown in Bold text) to which the PNA Fluor hybridizes. By comparison to prior examples, the donor fluorophore and acceptor quencher have been inverted so that the fluorescent polymer of the Detection Complex is released into the solution by operation of the amplification reaction. This change also demonstrates that both configurations are operable. The 5' primers are not labeled.

```
5' Primer:

5' HO-ATGACTGAATATAAACTTGT-OH                              3'  SEQ. ID No. 6

3' Primer:

5' Dabcyl(Linker)-TCATTCGCAATCACTCTATTGTTGGATCATATT-OH    3'  SEQ. ID No. 16
```

The primer DNAs were prepared using commercially available reagents and instrumentation and purified using conditions known to those of skill in the art. The Linker is a commercially available aminohexyl linker. The amine of the primer was labeled with Dabcyl-NHS prior to being cleaved from the synthesis support using conditions similar to those used for fluorescein labeling support bound PNA with 5(6)-carboxyfluorescein-NHS (See: Example 10).

dsDNA plasmid Template:

K-ras: The preparation of this plasmid was described in Example 15 except that it was linearized for this example by digestion with the restriction endonuclease Spe I. SpeI cuts the plasmid once, 35 bases (5') from the region amplified in this experiment.

```
           <- 3'priming site ->
3'  ...GAGATAACAACCTAGTATAAGCAGGTGTTTTACTAAGACTTAATCGACTTAGCAGTTCC..
5'  ...CTCTATTGTTGGATCATATTCGTCCACAAAATGATTCTGAATTAGCTGTATCGTCAAGG..

<-LKB.003 Hyb. Site->
..GTGAGAACGGATGCGGTGGTCGAGGTTGATGGTGTTCAAATATAAGTCAGTA... 5' SEQ ID No. 4
..CACTCTTGCCTACGCCACCAGCTCCAACTACCACAAGTTTATATTCAGTCAT... 3' SEQ ID No. 5
                             <- 5'priming site ->
```

The PNA Fluor was diluted in 50% aqueous DMF and stored at 4° C. whereas DNA primers and DNA templates were diluted in TE and stored at 4° C. Other reagents not specified are as described in Example 15.

PCR Assays:

PCR reactions were performed in the Perkin-Elmer 2400 thermocycler in individual mini-eppendorf tubes. Each 25 µL PCR reaction contained 2.5 mM $MgCl_2$, 200 µM ATP, 200 µM CTP, 200 µM GTP, 200 µM TTP, 1.0 µM 5' primer, 0.2 µM 3' Primer, 0.1 µM Cy3-PNA, 2 units AmpliTaq DNA polymerase, 50 mM KCl, and 10 mM TRIS pH 8.3. Reactions also included 1 µL of 1 nM K-ras/SpeI (K-ras plasmid digested with SpeI), or water (the "No Target" control). In addition, reactions also contained 1.0 µL of 5 µM LKB.003, or water (the "No Linear Beacon" control). Each PCR reaction was run in duplicate. A summary of the variable reagents added to each PCR reaction are displayed in Table 6.

The PCR protocol involved a 20 second warm up to 95° C. (1st round only), followed by denaturing at 95° C. for 5 seconds, annealing at 55° C. for 30 seconds, and extension at 74° C. for 30 seconds. The denaturation-annealing-extension cycle was repeated for 25 cycles.

For the fluorescent analysis of each reaction, a 5 µL sample was taken for analysis both before and after performing the PCR reaction. Each sample was diluted with 95 µL 50 mM KCl, 3 mM $MgCl_2$ and 10 mM TRIS, pH 8.3. Each sample was then analyzed using a Wallac multilabel counter using the Green Filter Set and the Red Filter Set as described in Example 16. The data obtained in the multilabel counter is reproduced in Table 6 and a portion is graphically illustrated in FIG. 19A.

In addition to the post PCR fluorescence analysis, 10 µL of each sample was mixed with 2.5 µL of 5x loading dye and then separated on a 10–20% gradient polyacrylamide gel. A digital composite negative image of the photograph of the gel after staining with ethidium bromide is presented in FIG. 19B.

Results

Data obtained for this Example 18 is presented in Table 6 and FIGS. 19A and 19B. With reference to Table 6, the Sample Number is identified in column A; the nature of the plasmid template for amplification is identified in column B; the presence of absence of the Linear Beacon (unimolecular "beacon" probe) is identified in column C; the raw pre-PCR fluorescence using the Green Filter Set is presented in column D; the raw post-PCR fluorescence using the Green Filter Set is presented in column E and the raw pre-PCR fluorescence using the Red Filter Set in presented in column F and the raw post-PCR fluorescence using the Red Filter Set is presented in column G. The data for the No Linear Beacon control using the Green Filter Set is not shown in the Table since there is no fluorescein present in these reactions.

The data in columns H and I of Table 6 are generated by dividing the Post-PCR measurements for a fluorophore by the pre-PCR measurements. For example, the data in row 3, column I (1.1) is generated by dividing 460 (row 3, column E) by 406 (row 3, column D). Thus, the data in columns H and I represent multiples of the relative increase in fluorescence intensity of the fluorescein (Flu) and cyanine (Cy3) label occurring as a result of performing the PCR reaction. No data is provided in column H where there was no data provided in columns D and E.

With reference to Table 6, the composition of Samples 1 through 4 are duplicates of the composition of Samples 5 through 8. As the data for both Samples 1–4 and Samples 5–8 are very similar, only the data for Samples 1–4 will be discussed below. Nevertheless, the consistency of the data demonstrates its reproducibility.

The multiples of the relative increases in fluorescence intensity occurring as a result of the PCR reaction are indicative of the proper operation of the assay, analysis will focus on the data in columns H and I of Table 6. For visual inspection, the data is also presented in a bar graph format in FIG. 19A. With reference to column I, the data in rows 1 and 2 compare well with the data in columns 3 and 4, respectively. Since signal from the Cy3 label is indicative of the dissociation of the Detection Complex, the three fold increase in red fluorescence in the presence of the plasmid template (rows 2 and 4) as compared to the absence of the plasmid template (rows 1 and 3) suggests that the PCR reaction performed whether or not the Linear Beacon was present in the reaction.

With reference to column H, the two fold increase in green fluorescence in the presence of the plasmid template (row 4) as compared with the absence of the plasmid template (row 3) is indicative of the generation of the amplicon to which the Linear Beacon (LBK.003) hybridizes to thereby generate detectable signal. Thus, the data is consistent with the formation of the desired amplicon.

With reference to the image of the ethidium bromide stained gel in FIG. 19B, a strong band of appropriate size is present in the lanes marked for Samples 2 and 4, but no band is observed in lanes marked for Samples 1 and 3 which lacked plasmid template (negative controls). Thus, the gel conclusively demonstrates that amplification occurred in Samples 2 and 4 to produce the desired amplicon and that no amplification occurred in Samples 1 or 3. This data correlates well with the fluorescence data presented in Table 6 and FIG. 19A.

TABLE 6

| A Sample No | B Target | C Probe | D FLU Pre | E FLU Post | F Cy3 Pre | G Cy3 Post | H FLU X | I Cy3 X |
|---|---|---|---|---|---|---|---|---|
| 1 | 1 | No Target | No Linear Beacon | N/A | N/A | 258 | 302 | N/A | 1.2 |
| 2 | 2 | K-ras/SpeI | No Linear Beacon | N/A | N/A | 262 | 1004 | N/A | 3.8 |
| 3 | 3 | No Target | LBK.003 | 406 | 460 | 268 | 280 | 1.1 | 1.0 |
| 4 | 4 | K-ras/SpeI | LBK.003 | 378 | 794 | 234 | 830 | 2.1 | 3.5 |
| 5 | 5 | No Target | No Linear Beacon | N/A | N/A | 256 | 296 | N/A | 1.2 |
| 6 | 6 | K-ras/SpeI | No Linear Beacon | N/A | N/A | 268 | 978 | N/A | 3.6 |
| 7 | 7 | No Target | LBK.003 | 404 | 506 | 282 | 266 | 1.3 | 0.9 |
| 8 | 8 | K-ras/SpeI | LBK.003 | 358 | 744 | 258 | 860 | 2.1 | 3.3 |

Summary:

The data indicated that PCR amplification generated positive independently detectable signal from both the Detection Complex and the unimolecular Linear Beacon probe. Consequently, the data demonstrates that independently detectable Detection Complexes and unimolecular "Beacon" probes can be commingled in the same multiplex closed tube assay. Non-limiting examples of uses for this assay format include internal PCR assay monitoring and independent identification of features of an amplicon.

We claim:

1. A composition comprising;
   a) at least one component probing polymer wherein the probing polymer comprises: 1) a probing segment that is complementary or substantially complementary to a target sequence; and 2) one or more interacting groups suitable for the formation of a complex with at least one other component polymer that is not the target sequence wherein the probing polymer can perform as a primer in an extension reaction upon hybridization of the probing segment to the target sequence;
   b) at least one component annealing polymer that is not the target sequence and which, at a minimum, comprises one or more interacting groups wherein the interacting groups of the component polymers form and stabilize the complex; and
   c) at least one set of donor and acceptor moieties wherein to each of at least two of the component polymers, that are not the target sequence, is linked at least one moiety from the set such that formation of the complex facilitates transfer of energy between donor and acceptor moieties of the set;

provided however, that at least one of the component polymers of the composition is a non-nucleic acid polymer.

2. The composition of claim 1, wherein all the component polymers are non-nucleic acid polymers.

3. The composition of claim 1, wherein at least one of the component polymers is a PNA.

4. The composition of claim 1, wherein all of the component polymers are PNA.

5. The composition of claim 3, wherein PNA subunits of a component polymer have the formula:

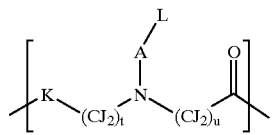

wherein,
each J is the same or different and is selected from the group consisting of: H, $R^1$, $OR^1$, $SR^1$, $NHR^1$, $NR^1_2$, F, Cl Br and I;
each K is the same or different and is selected from the group consisting of: O, S, NH and $NR^1$;
each $R^1$ is the same or different and is an alkyl group having one to five carbon atoms which may optionally contain a heteroatom or a substituted or unsubstituted aryl group;
each A is selected from the group consisting of a single bond, a group of the formula; —$(CJ_2)_s$— and a group of the formula; —$(CJ_2)_sC(O)$— wherein, J is defined above and each s is an integer from one to five;
each t is 1 or 2;
each u is 1 or 2; and
each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl.

6. The composition of claim 5, wherein each PNA subunit consists of a naturally occurring nucleobase attached to the aza nitrogen of the N-[2-(aminoethyl)]glycine backbone through a methylene carbonyl linkage.

7. The composition of claim 1, wherein the donor moiety is a fluorophore.

8. The composition of claim 7, wherein the fluorophore is selected from the group consisting of: 5(6)-carboxyfluorescein, 6-((7-amino-4-methylcoumarin-3-acetyl)amino)hexanoic acid, 5(and 6)-carboxy-X-rhodamine, Cyanine 2 Dye, Cyanine 3 Dye, Cyanine 3.5 Dye, Cyanine 5 Dye, Cyanine 5.5 Dye, Cyanine 7 Dye and Cyanine 9 Dye.

9. The composition of claim 1, wherein the acceptor moiety is a quencher moiety.

10. The composition of claim 9, wherein the quencher moiety is 4-((-4-(dimethylamino)phenyl)azo)benzoic acid (dabcyl).

11. The composition of claim 1, wherein a spacer moiety tethers one or more of the donor and acceptor moieties to the component polymer.

12. The composition of claim 1, wherein at least one linker is used to link together two segments of a component polymer.

13. The composition of claim 12, wherein the annealing polymer comprises two segments of interacting groups linked by one or more linkers.

14. The composition of claim 1, wherein at least one component polymer of the complex is immobilized or tethered to a surface.

15. The composition of claim 1, wherein the interacting groups are selected from the group consisting of hydrophobic moieties, ionic moieties and hydrogen bonding moieties.

16. The composition of claim 15, wherein the ionic moieties comprise salt pairs.

17. The composition of claim 15, wherein the hydrogen bonding moieties comprise complementary nucleobases linked to the subunits of the two or more component polymers.

18. The composition of claim 1, wherein the interacting groups are located at one termini of one or more of the component polymers.

19. The composition of claim 1, wherein the interacting groups are located at both termini of one or more of the component polymers.

20. The composition of claim 1, wherein the interacting groups are centered within one or more of the component polymers.

21. The composition of claim 1, wherein the complex comprises only one probing polymer and one annealing polymer.

22. The composition of claim 1, wherein the complex comprises at least three component polymers.

23. The composition of claim 1, wherein the complex comprises at least two Beacon Sets.

24. The composition of claim 23, wherein each Beacon Set comprises independently detectable moieties.

25. The composition of claim 24, wherein the independently detectable moieties of each Beacon Set are independently detectable donor fluorophores and the acceptor moieties of each Beacon Set are the same or different quencher moiety.

26. The composition of claim 25, wherein all acceptor moieties are the same quencher moiety.

27. The composition of claim 26, wherein the quencher moiety is dabcyl.

28. The composition of claim 1, wherein at least one of the component polymers is a PNA polymer labeled with a quencher moiety.

29. The composition of claim 28, wherein the PNA polymer is C-terminally labeled with dabcyl.

30. The composition of claim 1, wherein the probing polymer is selected from the group consisting of a nucleic acid and a PNA that has been modified to thereby facilitate polymerase extension.

31. The composition of claim 30, wherein:
(i.) the probing polymer comprises nucleobase containing interacting groups that do not sequence specifically interact with the target sequence; and wherein
(ii.) the annealing polymer comprises nucleobase containing interacting groups that are the exact complement to the interacting groups of the probing polymer.

32. The composition of claim 31, wherein the probing polymer is a nucleic acid bearing a 5'-fluorophore and the annealing polymer is a PNA polymer bearing a C-terminal quencher moiety.

33. The composition of claim 32, wherein at least one of the component polymers of the complex is immobilized or tethered to a surface.

34. An array of two or more different complexes wherein at least two complexes of the array each comprise;

a) at least one component probing polymer wherein the probing polymer comprises: 1) a probing segment that is complementary or substantially complementary to a unique target sequence; and 2) one or more interacting groups suitable for the formation of a complex with at least one other component polymer that is not the target sequence;

b) at least one component annealing polymer that is common to the at least two complexes of the array, that is not the target sequence and that, at a minimum, comprises one or more interacting groups wherein the interacting groups of the component polymers form and stabilize the complex; and c) at least one set of donor and acceptor moieties wherein to at least two of the component polymers is linked at least one moiety from the set such that formation of the complex facilitates transfer of energy between donor and acceptor moieties of the set;

provided however, that at least one of the component polymers of each different complex is immobilized or tethered to the surface of the array.

35. The array of claim 34, wherein all the component polymers are non-nucleic acid polymers.

36. The array of claim 34, wherein at least one of the component polymers is a PNA.

37. The array of claim 34, wherein all of the component polymers are PNA.

38. The array of any of claims 36 or 37, wherein PNA subunits of a component polymer or polymers have the formula:

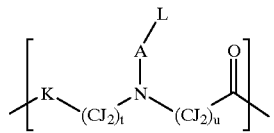

wherein,
each J is the same or different and is selected from the group consisting of: H, R$^1$, OR$^1$, SR$^1$, NHR$^1$, NR$^1{}_2$, F, Cl, Br and I;

each K is the same or different and is selected from the group consisting of: O, S, NH and NR$^1$;

each R$^1$ is the same or different and is an alkyl group having one to five carbon atoms which may optionally contain a heteroatom or a substituted or unsubstituted aryl group;

each A is selected from the group consisting of a single bond, a group of the formula; —(CJ$_2$)$_s$— and a group of the formula; —(CJ$_2$)$_s$C(O)— wherein, J is defined above and each s is an integer from one to five;

each t is 1 or 2;
each u is 1 or 2; and
each L is the same or different and is independently selected from the group consisting of J, adenine, cytosine, guanine, thymine, uridine, 5-methylcytosine, 2-aminopurine, 2-amino-6-chloropurine, 2,6-diaminopurine, hypoxanthine, pseudoisocytosine, 2-thiouracil, 2-thiothymidine, other naturally occurring nucleobase analogs, other non-naturally occurring nucleobases, substituted and unsubstituted aromatic moieties, biotin, fluorescein and dabcyl.

39. The array of claim 38, wherein each PNA subunit consists of a naturally occurring nucleobase attached to the aza nitrogen of a N-[2-(aminoethyl)]glycine backbone through a methylene carbonyl linkage.

40. The array of claim 34, wherein at least one complex of the array comprises at least three polymers.

41. The array of claim 34, wherein the common annealing polymer of the array is a PNA polymer comprising a quencher moiety.

42. An array of two or more different complexes wherein at least two complexes of the array each comprise;

a) at least one component probing polymer wherein the probing polymer comprises: 1) a probing segment that is complementary or substantially complementary to a unique target sequence; and 2) one or more interacting groups suitable for the formation of a complex with at least one other component polymer that is not the target sequence wherein the probing polymer of at least one complex can perform as a primer in an amplification reaction upon hybridization of the probing segment to a target sequence;

b) at least one component annealing polymer that is not the target sequence and which, at a minimum, comprises one or more interacting groups wherein the interacting groups of the component polymers form and stabilize the complex; and c) at least one set of donor and acceptor moieties wherein to at least two of the component polymers is linked at least one moiety from the set such that formation of the complex facilitates transfer of energy between donor and acceptor moieties of the set;

provided however that: (i) at least one of the component polymers of the complex is a non-nucleic acid polymer; and (ii) at least one of the component polymers of each different complex is immobilized or tethered to the surface of the array.

43. The array of claim 42, wherein the probing polymer is selected from the group consisting of a nucleic acid and a PNA that has been modified to thereby facilitate polymerase extension.

44. The array of claim 43, wherein:
(i) the probing polymer comprises nucleobase containing interacting groups that do not sequence specifically interact with the target sequence; and wherein
(ii) the annealing polymer comprises nucleobase containing interacting groups that are the exact complement to the interacting groups of the probing polymer.

45. The array of claim 44, wherein the probing polymer is a nucleic acid polymer bearing a 5'-fluorophore and the annealing polymer is a PNA polymer bearing a C-terminal quencher moiety.

46. A method for determining the presence, absence or quantity of a target molecule, comprising at least one target sequence, in a sample; said method comprising:

a) contacting the sample with at least one complex, said complex comprising:
(i) at least one component probing polymer wherein the probing polymer comprises: 1) a probing segment that hybridizes to said target sequence; and 2) one or more interacting groups suitable for the formation of a complex with at least one other component polymer that is not the target sequence;
(ii) at least one component annealing polymer that is not the target sequence and which, at a minimum, comprises one or more interacting groups wherein the interaction of the interacting groups of the component polymers form and stabilize the complex; and
(iii) at least one set of donor and acceptor moieties wherein to each of at least two component polymers is linked at least one moiety from the set such that formation of the complex facilitates transfer of energy between donor and acceptor moieties of the set in a manner that is detectably different as compared to when the component polymers are not complexed or when the probing segment is hybridized to the target sequence;

provided however, that at least one of the component polymers of the complex is a non-nucleic acid polymer; and b) detecting, identifying or quantitating changes in detectable signal attributable to the changes in the transfer of energy between the donor and acceptor moieties of a set upon dissociation of the complex or upon the hybridization of the probing segment to the target sequence and correlating the change in signal with the presence, absence or quantity of the target molecule in the sample wherein the detectable signal is produced as a result of hybridization of the probing segment of the probing polymer to the target sequence of the target molecule which thereby facilitates a secondary triggering event that causes indirect dissociation of the complex.

47. The method of claim 46, wherein all the component polymers are non-nucleic acid polymers.

48. The method of claim 46, wherein at least one of the component polymers is a PNA.

49. The method of claim 46, wherein all of the component polymers are PNA.

50. The method of claim 46, wherein the method is used to detect a nucleic acid target molecule of interest which may be present or produced in a closed tube assay.

51. The method of claim 50, wherein the target molecule to be determined by the method is produced by a process selected from the group consisting of Polymerase Chain Reaction (PCR), Ligase Chain Reaction (LCR), Strand Displacement Amplification (SDA), Transcription-Mediated Amplification (TMA), Q-beta replicase amplification (Q-beta) and Rolling Circle Amplification (RCA).

52. The method of claim 50, wherein the nucleic acid target molecule of interest is an amplicon that has been produced as a result of performing a nucleic acid amplification reaction.

53. The method of claim 46, wherein the target molecule is immobilized to a surface.

54. The method of claim 46, wherein at least one of the component probing polymers of the complex is immobilized or tethered to a surface with which the sample of interest is contacted.

55. The method of claim 54, wherein the complex dissociates to release the common annealing component polymer into solution.

56. The method of claim 46, wherein the detectable signal is produced as a result of hybridization of the probing segment of the probing polymer to the target sequence of the target molecule without direct or indirect dissociation of the complex.

57. The method of claim 46, wherein the detectable signal is produced as a result of hybridization of the probing segment of the probing polymer to the target sequence of the target molecule which thereby causes direct dissociation of the complex.

58. A method for detecting, identifying or quantitating a nucleic acid target molecule of interest in a sample wherein said target molecule comprises at least one priming site and said method comprises:

a) contacting the sample with:

I) at least one complex formed from two or more component polymers that are not the target sequence, the complex comprising:

(i) at least one component probing polymer that can perform as a primer in an primer extension reaction and wherein the probing polymer, at a minimum comprises:

1) a probing segment that hybridizes to a first priming site; and 2) one or more interacting groups suitable for the formation of a complex with at least one other component polymer;

(ii) at least one component annealing polymer which, at a minimum, comprises one or more interacting groups wherein the interacting groups of the component polymers form and stabilize the complex; and (iii) at least one set of donor and acceptor moieties wherein to each of at least two component polymers is linked at least one moiety from the set such that formation of the complex facilitates transfer of energy between donor and acceptor moieties of the set in a manner that is detectably different from when the component polymers exist independently or unassociated; and II) all other components necessary to perform a primer extension reaction; and b) performing a primer extension reaction which thereby causes the complex to dissociate in proportion to the quantity of nucleic acid produced by the primer extension reaction; and c) detecting, identifying or quantitating changes in detectable signal attributable to the transfer of energy between the donor and acceptor moieties of a set upon dissociation of the complex and correlating the changes in detectable signal with the presence, absence or quantity of the nucleic acid target molecule of interest in the sample.

59. The method of claim 58, wherein all component polymers of the complex are labeled nucleic acids.

60. The method of claim 58, wherein at least one component polymer of the complex is a non-nucleic acid polymer.

61. The method of claim 58, wherein at least one component polymer of the complex is a PNA.

62. The method of claim 58, wherein the primer extension reaction is part of a nucleic acid amplification process.

63. The method of claim 62, wherein the method is used to detect a nucleic acid target molecule of interest that is a template for PCR.

64. The method of claim 63, wherein complex dissociation occurs as a consequence of the activity of the amplification process and the signal produced by dissociation of the complex is monitored in a closed tube assay format that facilitates both end-point or real-time assay measurements.

65. The method of claim 64, wherein the amplification process is PCR.

66. The method of claim 65, wherein other assay components include buffers, inorganic salt, magnesium, nucleoside triphosphates, a polymerase enzyme, and a second primer wherein the second primer and the complex comprise the forward and reverse primers of the PCR reaction.

67. The method of claim 66, wherein the second primer is a second complex that hybridizes to a second primer site of the target molecule; said second complex comprising:

(a) at least one second component probing polymer which, at a minimum, comprises:

1) a probing segment, wherein said probing segment performs as the second primer in the PCR process; and 2) one or more interacting groups suitable for the formation of the second complex with at least one other component polymer that is not the target sequence;

(b) at least one second component annealing polymer that is not the target sequence and which, at a minimum, comprises one or more interacting groups wherein the interacting groups of the component polymers form and stabilize the second complex; and (c) at least one second set of donor and acceptor moieties wherein to each of at least two component polymers of the second complex is linked at least one moiety from the second set such that formation of the second complex facilitates transfer of energy between donor and acceptor moieties of the set in a manner that is detectably different from when the component polymers of the second complex exist independently or unassociated.

68. The method of claim 58, wherein the probing polymer is selected from the group consisting of a nucleic acid and a PNA that has been modified to thereby facilitate polymerase extension.

69. The method of claim 68, wherein:
(i) the probing polymer comprises nucleobase containing interacting groups that do not sequence specifically interact with the first primer site; and wherein
(ii) the annealing polymer comprises nucleobase containing interacting groups that are the exact complement to the interacting groups of the probing polymer.

70. The method of claim 58, wherein at least one of the component polymers of the complex is immobilized or tethered to a surface.

71. The method of claim 58, wherein the extension reaction is a component of a process selected from the group consisting of Polymerase Chain Reaction (PCR), Strand Displacement Amplification (SDA), Transcription-Mediated Amplification (TMA), Q-beta replicase amplification (Q-beta) and Rolling Circle Amplification (RCA).

72. The method of claim 67, wherein all component polymers of the second complex are appropriately labeled nucleic acids.

73. The method of claim 67, wherein at least one component polymer of the complex is a non-nucleic acid polymer.

74. The method of claim 67, wherein at least one component polymer of the complex is a PNA.

75. The method of claim 67, wherein the annealing polymer of the second complex is a PNA polymer bearing a quencher moiety.

76. The method of claim 67, wherein the same annealing polymer is common to both the first complex and the second complex.

77. The method of claim 76, wherein the common annealing polymer is a PNA bearing a quencher acceptor moiety.

78. The method of claim 67, wherein the first and second complexes comprise the same donor fluorophore and acceptor quencher.

79. The method of any of claims 58 or 67, wherein the sample is additionally contacted with one or more blocking probes to thereby suppress the binding of a probing segment of a probing polymer of one or more of the complexes to a priming site on the target molecule.

80. The method of any of claims 58 or 67, wherein PCR clamping is used to modify the assay so that it is suitable for performing a closed tube point mutation analysis that can be monitored in real-time or at the end-point.

81. The method of claim 80, wherein at least one independently detectable unimolecular "beacon" probe is also included in a PCR assay and hybridizes to a hybridization site within the amplicon to thereby generate an independently detectable signal that can be used to either monitor proper operation of the PCR amplification or be used to independently identify a feature of the amplicon generated in the assay.

82. The method of claim 81, wherein the specific feature to be determined by the assay is whether wild type, mutant or both wild type and mutant target molecules were present in the sample.

83. The method of claim 82, wherein the hybridization site of the wild type and mutant target molecules are related as a point mutation.

84. The method of claim 82, wherein the specific feature can be independently detected in a closed tube format in either real-time or at the end-point of the assay.

85. The method of claim 84, wherein signal from the one or more complexes and the one or more unimolecular "Beacon" probes present in the assay is independently detectable in a closed tube format in either real-time or at the end-point of the assay.

86. The method of any of claims 58 or 67, wherein at least two or more independently detectable complexes are present in a single multiplex assay that is used to simultaneously detect, identify or quantitate two or more target molecules of interest in the same sample and in the same assay.

87. The method of claim 86, wherein the independently detectable complexes are used in a closed tube format and the detectable change in signal from each independently detectable complex is monitored in either real-time or at the end-point of the assay.

88. A method for the formation of two or more different complexes each comprising a common annealing polymer, said method comprising mixing together two or more different component probing polymers with a common component annealing polymer under conditions that facilitate complex formation, wherein each complex comprises:

a) at least one component probing polymer wherein the probing polymer comprises: 1) a probing segment that is complementary or substantially complementary to a target sequence; and 2) one or more interacting groups suitable for the formation of a complex with at least one other component polymer that is not the target sequence;

b) at least one common component annealing polymer that is not the target sequence and which, at a minimum, comprises one or more interacting groups wherein the interaction of the interacting groups of the component polymers form and stabilize the different complexes; and c) at least one set of donor and acceptor moieties wherein to each of at least two component polymers of a particular complex is linked at least one moiety from the set such that formation of the complex facilitates transfer of energy between donor and acceptor moieties of the set in a manner that is detectably different as compared to when the component polymers are not complexed or when the probing segment is hybridized to the target sequence.

89. The method of claim 88, wherein all the component polymers are non-nucleic acid polymers.

90. The method of claim 88, wherein at least one of the component polymers is a PNA.

91. The method of claim 88, wherein at least one component polymer is support bound.

92. A kit comprising three or more different component polymers suitable for the formation of at least two different complexes, said kit comprising;

a) at least two different component probing polymers wherein the probing polymers each comprise: 1) a probing segment that is complementary or substantially complementary to a target sequence; and 2) one or more interacting groups suitable for the formation of a complex with at least one other component polymer that is not the target sequence;

b) at least one common component annealing polymer that is not the target sequence and which, at a minimum, comprises one or more interacting groups wherein the interacting groups of the component polymers form and stabilize the two or more different complexes; and c) at least one set of donor and acceptor moieties wherein to each of at least two component polymers of a particular complex is linked at least one moiety from the set such that formation of the complex facilitates transfer of energy between donor and acceptor moieties of the set in a manner that is detectably different as compared to when the component polymers are not complexed or when the probing segment is hybridized to the target sequence.

93. The kit of claim 92, wherein all the component polymers are non-nucleic acid polymers.

94. The kit of claim 92, wherein at least one of the component polymers is a PNA.

95. A composition comprising:

a) at least two component polymers that are not a target sequence to be detected in an assay and wherein the component polymers each comprise interacting groups that form and stabilize a complex; and;

b) at least one set of donor and acceptor moieties wherein to at least two component polymers is linked at least one moiety from the set such that formation of the composition facilitates transfer of energy between donor and acceptor moieties of the set in a manner that is detectably different as compared to when the component polymers are not complexed; and wherein the composition is further characterized in that the composition forms a substrate that causes the complex to dissociate when acted upon by an enzyme; and further provided that at least one of the component polymers is a non-nucleic acid polymer.

96. The composition of claim 95, wherein at least one of the non-nucleic acid polymers is a PNA.

97. A method for determining the presence, absence or quantity of a target molecule, comprising at least one target sequence, in a sample, said method comprising:

a) immobilizing an enzyme to the target sequence of the target molecule; and b) contacting the sample with at least one complex, said complex comprising:

(i) at least two component polymers wherein the component polymers each comprise interacting groups that form and stabilize the complex; and (ii) at least one set of donor and acceptor moieties wherein to at least two component polymers is linked at least one moiety from the set such that formation of the composition facilitates transfer of energy between donor and acceptor moieties of the set in a manner that is detectably different as compared to when the component polymers are not complexed; and wherein the complex is further characterized in that the complex forms a substrate that dissociates when acted upon by the enzyme; and c) detecting, identifying or quantitating changes in detectable signal attributable to the transfer of energy between the donor and acceptor moieties of a set upon dissociation of the complex and correlating the changes in detectable signal with the presence, absence or quantity of the target molecule of interest in the sample.

98. The method of claim 97 wherein at least one of the component polymers of the complex is non-nucleic acid polymer.

99. The method of claim 98, wherein at least one of the non-nucleic acid polymers of the complex is a PNA.

100. A method for determining the presence, absence or quantity of a target molecule, comprising at least one target sequence, in a sample using an array and then regenerating an array; said method comprising:

a) contacting the sample with an array containing at least one complex, said complex comprising:

(i) at least one component probing polymer wherein the probing polymer comprises: 1) a probing segment that hybridizes to said target sequence; and 2) one or more interacting groups suitable for the formation of a complex with at least one other component polymer that is not the target sequence;

(ii) at least one component annealing polymer that is not the target sequence and which, at a minimum, comprises one or more interacting groups wherein the interaction of the interacting groups of the component polymers form and stabilize the complex; and (iii) at least one set of donor and acceptor moieties wherein to each of at least two component polymers is linked at least one moiety from the set such that formation of the complex facilitates transfer of energy between donor and acceptor moieties of the set in a manner that is detectably different as compared to when the component polymers are not complexed or when the probing segment is hybridized to the target sequence;

provided however, that at least one of the component polymers of the complex is a non-nucleic acid polymer; and b) detecting, identifying or quantitating changes in detectable signal attributable to the changes in the transfer of energy between the donor and acceptor moieties of a set upon dissociation of the complex or upon the hybridization of the probing segment to the target sequence and correlating the change in signal with the presence, absence or quantity of the target molecule in the sample, wherein:

(i) at least one of the component polymers of the complex is one of at least two immobilized or tethered complexes on the array with which the sample of interest is contacted;

(ii) the complex dissociates to release at least one common labeled component polymer into solution;

(iii) the common labeled component polymer is released from two or more of the different immobilized or tethered complexes of an array; and (c) regenerating complexes on the surface by;

a) removing any hybridized target molecules from the surface; and b) contacting the surface with a quantity of the common labeled component polymer as is necessary to regenerate all the complexes of the array.

101. The method of claim 100, wherein the common labeled component polymer is a PNA polymer labeled with a quencher moiety.

102. The method of claim 100, wherein at least two of the immobilized or tethered component polymers are PNA polymers.

* * * * *